US011597729B2

(12) United States Patent
Wu et al.

(10) Patent No.: US 11,597,729 B2
(45) Date of Patent: Mar. 7, 2023

(54) TROPOMYOSIN RECEPTOR KINASE INHIBITOR, PREPARATION METHOD THEREFOR AND USE THEREOF

(71) Applicant: JIANGSU VCARE PHARMATECH CO., LTD., Jiangsu (CN)

(72) Inventors: Yong Wu, Jiangsu (CN); Wenbin Zhou, Jiangsu (CN); Yanchun Gong, Jiangsu (CN); Yaoxiang Yue, Jiangsu (CN); Jie Deng, Jiangsu (CN); Yongqiang Liu, Jiangsu (CN)

(73) Assignee: JIANGSU VCARE PHARMATECH CO., LTD., Jiangsu (CN)

( * ) Notice: Subject to any disclaimer, the term of this patent is extended or adjusted under 35 U.S.C. 154(b) by 132 days.

(21) Appl. No.: 17/044,791

(22) PCT Filed: Jun. 6, 2019

(86) PCT No.: PCT/CN2019/090226
§ 371 (c)(1),
(2) Date: Oct. 1, 2020

(87) PCT Pub. No.: WO2019/233461
PCT Pub. Date: Dec. 12, 2019

(65) Prior Publication Data
US 2021/0094953 A1    Apr. 1, 2021

(30) Foreign Application Priority Data

Jun. 8, 2018 (CN) .......................... 201810597223.9
May 31, 2019 (CN) .......................... 201910467671.1

(51) Int. Cl.
*C07D 471/22* (2006.01)
*A61P 35/00* (2006.01)
*C07D 487/22* (2006.01)

(52) U.S. Cl.
CPC ............ *C07D 471/22* (2013.01); *A61P 35/00* (2018.01); *C07D 487/22* (2013.01)

(58) Field of Classification Search
CPC .......................... C07D 471/22; C07D 487/22
See application file for complete search history.

(56) References Cited

FOREIGN PATENT DOCUMENTS

| CN | 102971322 A | 3/2013 |
|---|---|---|
| CN | 107207514 A | 9/2017 |
| CN | 107735399 A | 2/2018 |
| WO | 2011146336 A1 | 11/2011 |
| WO | 2012034095 A1 | 3/2012 |
| WO | 2017075107 A1 | 5/2017 |
| WO | 2018081417 A2 | 5/2018 |

OTHER PUBLICATIONS

Ultsch, Mark H. et al.; Crystal Structures of the Neurotrophin-binding Domain of TrkA, TrkB and TrkC; J. Mol. Biol. (1999) 290, 149-159; Article No. jmbi.1999.2816.
Lange, Allison M. et al.; Inhibiting TRK Proteins in Clinical Cancer Therapy; MDPI-Cancers; 2018, 10, 105; doi:10.3390/cancers10040105.
Woolf, C.J. et al.; Nerve Growth Factor Contributes to the Generation of Inflammatory Sensory Hypersensitivity; Neuroscience; vol. 62, No. 2, pp. 327-331, 1994.
Cho, Hee-Jung et al.; Expression of mRNA for brain-derived neurotrophic factor in the dorsal root ganglion following peripheral inflammation; Brain Research 749, (1997) 358-362.
Li, Changqi et al.; Brain derived neurotrophic factor (BDNF) contributes to the pain hypersensitivity following surgical incision in the rats; Molecular Pain 2008,4,27.
Wang, Tao et al.; Trk kinase inhibitors as new treatments for cancer and pain; Expert Opin.Ther.Patents 2009,19(3):305-319.
V. Freund-Michel et al.; The nerve growth factor and its receptors in airway inflammatory diseases; Pharmacology & Therapeutics 117 (2008) 52-76.
Hu, Vivian Y. et al.; Decrease in Bladder Overactivity With REN1820 in Rats With Cyclophosphamide Induced Cystitis; The Journal of Urology; vol. 173,1016-1021, Mar. 2005.
F F Di Mola et al.; Nerve growth factor and Trk high affinity receptor (TrkA) gene expression in inflammatory bowel disease; Gut, 2000; 46:670-678.
Dou, Ying-Chun et al.; Increased nerve growth factor and its receptors in atopic dermatitis: an immunohistochemical study; Archives of Dermatological Research 2006,298: 31-37; Apr. 4, 2006.
Raychaudhuri, Siba P.; et al.; K252a, a High-Affinity Nerve Growth Factor Receptor Blocker, Improves Psoriasis: An In Vivo Study Using the Severe Combined Immunodeficient Mouse-Human Skin Model; J.Investigative Dermatology 2004, 122: 812-819.

(Continued)

*Primary Examiner* — Alicia L Otton
(74) *Attorney, Agent, or Firm* — Novick, Kim & Lee, PLLC; Allen Xue

(57) ABSTRACT

Disclosed in the present invention are a pyrazolo [1,5-a] pyrimidine derivative having a structure of formula (I), a pharmaceutical composition comprising the compound of formula (I), and use of the compound in the preparation of a medicament for preventing or treating diseases associated with tropomyosin receptor kinases, in particular for preventing or treating cancers associated with tropomyosin receptor kinases. Each substituent in formula (I) has the same definition as that in the description.

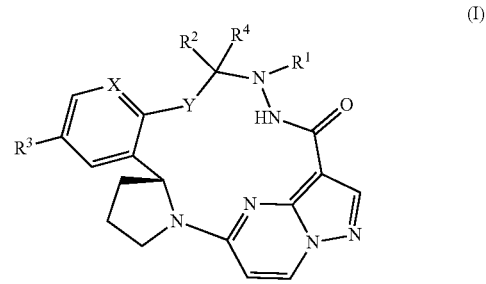

(I)

13 Claims, 13 Drawing Sheets

(56) References Cited

OTHER PUBLICATIONS

Nakagawara, Akira; Trk receptor tyrosine kinases: A bridge between cancer and neural development; Cancer Letters 169 (2001) 107-114.
Meyer, J. et al.; Remarkable leukemogenic potency and quality of a constitutively active neurotrophin receptor, TrkA; Leukemia (2007) 21, 2171-2180.
Pierotti, Marco A. et al.; Oncogenic rearrangements of the NTRK1/NGF receptor; Cancer Letters 232 (2006) 90-98.
Adriaenssens, Eric et al.; Nerve Growth Factor is a Potential Therapeutic Target in Breast Cancer; Cancer Res 2008; 68: (2); Jan. 15, 2008.

TROPOMYOSIN RECEPTOR KINASE INHIBITOR, PREPARATION METHOD THEREFOR AND USE THEREOF

RELATED APPLICATIONS

This application is a national stage application of PCT/CN2019/090226 (filed Jun. 6, 2019), which claims the priority of Chinese Patent Application Nos. CN201810597223.9 (filed Jun. 8, 2018) and CN201910467671.1 (filed May 31, 2019), contents of which having been incorporated herein in their entirety.

FIELD OF THE INVENTION

The present application relates to the field of medicine, and in particular relates to pyrazolo[1,5-a]pyrimidine derivatives and uses thereof for the treatment of diseases associated with pain, cancer and inflammation.

BACKGROUND OF THE INVENTION

Tropomyosin receptor kinases (Trks) are a family of receptor tyrosine kinases that can regulate synaptic strength and plasticity in the mammalian nervous system. The activation of Trk receptors affects neuronal survival and differentiation through various signaling pathways, and also has significant effects on the function of neurons. The common ligands for Trk receptors are neurotrophins, which play a key role in the nervous system, and the respective binding between these molecules is highly specific (J. Mol. Biol. 1999, 90, 149). Each type of neurotrophin has a corresponding Trk receptor with different affinity. Binding leads to activation of the Trk receptor by dimerization and phosphorylation, causing activation of downstream signals including RAS/MAPK/ERK, PLCγ and PI3K/Akt pathways etc., and thus regulation of survival and other functions of cells (Cancers 2018, 10, 105).

Inhibitors in the Trk/neurotrophin pathways have been proven effective in many preclinical animal models of pain. For example, the antibody RN-624 that antagonizes nerve growth factors NGF and TrkA has been shown effective in animal models of inflammatory pain and neuropathic pain (Neuroscience 1994, 62, 327; Eur. J. Neurosci. 1999, 11, 837). In addition, some literature indicates that after inflammation, the level of brain-derived neurotrophic factor (BDNF) and TrkB signaling in the dorsal root ganglion increase (Brain Research 1997, 749, 358). Multiple studies have shown that inhibition of the BDNF/TrkB pathway and reduction of signal transduction by antibodies can slow down neuroticism and associated pain (Molecular Pain 2008, 4, 27). At present, a variety of small molecule inhibitors of Trk kinases have been shown to be useful in the treatment of pain (Expert Opin. Ther. Patents 2009, 19, 305).

In addition, the use of anti-NGF antibodies or small molecule inhibitors of TrkA, B, and C to block the neurotrophic factor/Trk pathway has been shown to be effective in preclinical models of inflammatory diseases, such as inflammatory lung diseases, including asthma (Pharmacology & Therapeutics 2008, 117, 52), interstitial cystitis (The Journal of Urology 2005, 173, 1016), inflammatory bowel disease (including ulcerative colitis and Crohn's disease (Gut2000, 46, 670)), inflammatory skin disease and the like (Archives of Dermatological Research 2006, 298, 31), eczema and psoriasis (J. Investigative Dermatology 2004, 122, 812), etc.

Literature reports also show that over-expression, activation, amplification or mutation of Trk kinases is closely associated with many cancers, including neuroblastoma, ovarian cancer, glioblastoma, lung adenocarcinoma, juvenile sarcoma, colorectal cancer, fibrosarcoma, Spitzoid melanoma, thyroid cancer, intrahepatic cholangiocarcinoma, large cell neuroendocrine carcinoma, papillary thyroid cancer, pilocytic astrocytoma, head and neck squamous cell carcinoma, acute myeloid leukemia, congenital mesoblastic nephroma, ductal adenocarcinoma, gastrointestinal stromal tumor, mammary analogue secretory carcinoma (Cancers 2018, 10, 105), etc. In preclinical models of cancer, small molecule inhibitors of TrkA, B, and C effectively inhibit tumor growth and prevent tumor metastasis (Cancer Letters 2001, 169, 107; Leukemia 2007, 1-10; Cancer Letters 2006, 232, 90; Cancer Res 0.2008, 68, 346).

SUMMARY OF THE INVENTION

One object of the present invention is to provide a pyrazolo[1,5-a]pyrimidine Trk inhibitor.

Another object of the present invention is to provide the use of the Trk inhibitor in the preparation of a medicament for preventing or treating diseases associated with tropomyosin receptor kinases.

To achieve the objects of the present invention, the technical solutions of the present invention are as follows:

A compound represented by the following formula (I), stereoisomer thereof or pharmaceutically acceptable salt thereof according to the present invention:

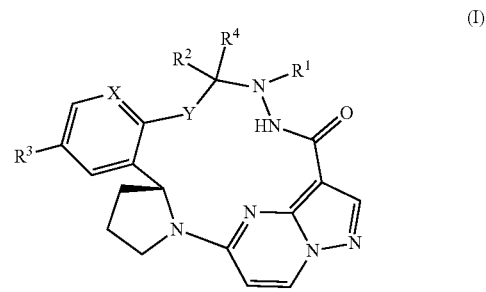

(I)

$R^1$ is selected from H, $C_1$-$C_8$ alkyl, $C_3$-$C_8$ cycloalkyl, $C_2$-$C_8$ alkenyl, $C_2$-$C_8$ alkynyl, —$COR^5$, —$SO_2R^5$ or —$SOR^5$, and optionally further substituted with one or more substituents selected from deuterium, halogen, hydroxyl, cyano, nitro, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxyl, or a 4-10 membered heterocyclic group;

$R^2$ and $R^4$ are each independently selected from H, $C_1$-$C_8$ alkyl, $C_3$-$C_8$ cycloalkyl, $C_2$-$C_8$ alkenyl or $C_2$-$C_8$ alkynyl, and optionally further substituted with one or more substituents selected from deuterium, halogen, hydroxyl, cyano, nitro, —$NR^9R^8$, —$NR^6COR^5$, —$COR^5$, —$SO_2R^5$, —$SOR^5$, $C_1$-$C_8$alkyl, $C_3$-$C_8$ cycloalkyl, $C_1$-$C_8$ alkoxyl, or a 4-10 membered heterocyclic group;

$R^5$ and $R^7$ are each independently selected from H, $C_1$-$C_8$alkyl, $C_3$-$C_8$ cycloalkyl, or —$NR^8$;

$R^6$ and $R^8$ are each independently selected from H, $C_1$-$C_8$ alkyl, or $C_3$-$C_8$ cycloalkyl;

Y is —$(CH_2)_n$— or —$O(CH_2)_n$—;

n is selected from 0, 1, 2 or 3;

alternatively, any two of $R^1$, $R^2$ and $R^4$ can independently form a $C_3$-$C_8$ cycloalkyl group or a 4-10 membered heterocyclic group;

$R^3$ is selected from H, deuterium, halogen, cyano, nitro, $C_1$-$C_8$ alkyl, $C_3$-$C_8$ cycloalkyl, or $C_1$-$C_8$alkoxy; and X is selected from CH or N.

An embodiment of the present invention is a compound of general formula (II), stereoisomer thereof or pharmaceutically acceptable salt thereof:

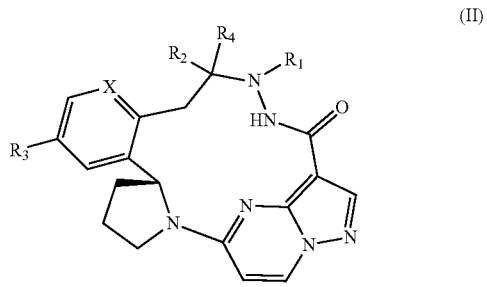

(II)

$R^1$ is selected from H, $C_1$-$C_8$ alkyl, $C_3$-$C_8$ cycloalkyl, $C_2$-$C_8$ alkenyl, $C_2$-$C_8$ alkynyl, —$COR^5$, —$SO_2R^5$ or —$SOR^5$, and optionally further substituted with one or more substituents selected from deuterium, halogen, hydroxyl, cyano, nitro, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxyl, or a 4-10 membered heterocyclic group;

$R^2$ and $R^4$ are each independently selected from H, $C_1$-$C_8$ alkyl, $C_3$-$C_8$ cycloalkyl, $C_2$-$C_8$ alkenyl or $C_2$-$C_8$ alkynyl, and optionally further substituted with one or more substituents selected from deuterium, halogen, hydroxyl, cyano, nitro, —$NR^6R^8$, —$NR^6COR^5$, —$COR^5$, —$SO_2R^5$, —$SOR^5$, $C_1$-$C_8$ alkyl, $C_3$-$C_8$ cycloalkyl, $C_1$-$C_8$ alkoxyl, or a 4-10 membered heterocyclic group;

$R^5$ and $R^7$ are each independently selected from H, $C_1$-$C_8$alkyl, $C_3$-$C_8$ cycloalkyl, or —$NR^8$;

$R^6$ and $R^8$ are each independently selected from H, $C_1$-$C_8$ alkyl, or $C_3$-$C_8$ cycloalkyl;

alternatively, any two of $R^1$, $R^2$ and $R^4$ can independently form a $C_3$-$C_8$ cycloalkyl group or a 4-10 membered heterocyclic group;

$R^3$ is selected from H, deuterium, halogen, cyano, nitro, $C_1$-$C_8$alkyl, $C_3$-$C_8$ cycloalkyl, or $C_1$-$C_8$ alkoxy; and X is selected from CH or N.

The embodiment of the present invention, wherein:

$R^1$ is selected from H, $C_1$-$C_8$ alkyl, $C_3$-$C_8$ cycloalkyl, $C_2$-$C_8$ alkenyl or $C_2$-$C_8$ alkynyl, and optionally further substituted with one or more substituents selected from deuterium, halogen, hydroxyl, cyano, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxy, or a 4-10 membered heterocyclic group;

$R^2$ and $R^4$ are each independently selected from H, $C_1$-$C_8$ alkyl, $C_3$-$C_8$ cycloalkyl, $C_2$-$C_8$ alkenyl or $C_2$-$C_8$ alkynyl, and optionally further substituted with one or more substituents selected from deuterium, halogen, hydroxyl, cyano, —$NR^6R^8$, —$NR^6COR^5$, —$COR^5$, —$SO_2R^5$, —$SOR^5$, $C_1$-$C_8$ alkyl, $C_3$-$C_8$ cycloalkyl, $C_1$-$C_8$ alkoxy, or a 4-10 membered heterocyclic group;

$R^5$ and $R^7$ are each independently selected from H, $C_1$-$C_8$ alkyl, $C_3$-$C_8$ cycloalkyl, or —$NR^8$;

$R^6$ and $R^8$ are each independently selected from H, $C_1$-$C_8$ alkyl, or $C_3$-$C_8$ cycloalkyl;

alternatively, any two of $R^1$, $R^2$ and $R^4$ can independently form a $C_3$-$C_8$ cycloalkyl group or a 4-10 membered heterocyclic group;

$R^3$ is halogen; and X is selected from CH or N.

The embodiment of the present invention, wherein:

$R^1$ is selected from H, $C_1$-$C_8$ alkyl or $C_3$-$C_8$ cycloalkyl, and optionally further substituted with one or more selected from deuterium, halogen, hydroxyl, cyano, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxy, or a 4-10 membered heterocyclic group;

$R^2$ and $R^4$ are each independently selected from H, $C_1$-$C_8$ alkyl or $C_3$-$C_8$ cycloalkyl, and optionally further substituted with one or more substituents selected from deuterium, halogen, hydroxyl, cyano, —$NR^6R^8$, —$NR^6COR^5$, —$COR^5$, —$SO_2R^5$, —$SOR^5$, $C_1$-$C_8$ alkyl, $C_3$-$C_8$ cycloalkyl, $C_1$-$C_8$ alkoxy, or a 4-10 membered heterocyclic group;

$R^5$ and $R^7$ are each independently selected from H, $C_1$-$C_8$ alkyl, $C_3$-$C_8$ cycloalkyl, or —$NR^8$;

$R^6$ and $R^8$ are each independently selected from H, $C_1$-$C_8$ alkyl or $C_3$-$C_8$ cycloalkyl;

alternatively, any two of $R^1$, $R^2$ and $R^4$ can independently form a $C_3$-$C_8$ cycloalkyl group or a 4-10 membered heterocyclic group;

$R^3$ is halogen; and

X is selected from CH or N.

The embodiment of the present invention, wherein:

$R^1$ is selected from H, $C_1$-$C_8$ alkyl or $C_3$-$C_8$ cycloalkyl, and optionally further substituted with one or more substituents selected from deuterium, halogen, hydroxyl, cyano, —$SO_2R^7$, $C_1$-$C_4$ alkyl, $C_3$-$C_6$ cycloalkyl or $C_1$-$C_4$ alkoxy;

$R^7$ is selected from H, $C_1$-$C_8$ alkyl, or $C_3$-$C_8$ cycloalkyl;

$R^2$ and $R^4$ are each independently selected from H, $C_1$-$C_8$ alkyl or $C_3$-$C_8$ cycloalkyl, and optionally further substituted with one or more substituents selected from deuterium, halogen, hydroxyl, cyano, $C_1$-$C_4$ alkyl, $C_3$-$C_6$ cycloalkyl, or $C_1$-$C_4$ alkoxy;

alternatively, any two of $R^1$, $R^2$ and $R^4$ can independently form a $C_3$-$C_8$ cycloalkyl group or a 4-10 membered heterocyclic group;

$R^3$ is halogen; and X is CH or N.

The embodiment of the present invention, wherein:

$R^1$ is selected from H, $C_1$-$C_8$ alkyl, or $C_3$-$C_8$ cycloalkyl, and optionally further substituted with one or more substituents selected from deuterium, hydroxyl, halogen, —$SO_2R^7$, or $C_1$-$C_4$ alkoxy;

$R^7$ is selected from H or $C_1$-$C_8$ alkyl; $R^2$ and $R^4$ are each independently selected from H, $C_1$-$C_8$ alkyl, or $C_3$-$C_8$ cycloalkyl;

alternatively, any two of $R^1$, $R^2$ and $R^4$ can independently form a 4-10 membered heterocyclic group;

$R^3$ is fluorine or chlorine; and X is selected from CH or N.

The embodiment of the present invention, wherein:

$R^1$ is selected from H, methyl, ethyl, n-propyl, isopropyl, n-butyl, isobutyl, tert-butyl, cyclopropyl, cyclobutyl, cyclopentyl, or cyclohexyl, and optionally further substituted with one or more substituents selected from deuterium, hydroxyl, F, Cl, —$SO_2CH_3$, or methoxy;

$R^2$ and $R^4$ are each independently selected from H, methyl, ethyl, n-propyl, isopropyl, n-butyl, isobutyl, tert-butyl, cyclopropyl, cyclobutyl, cyclopentyl, or cyclohexyl;

alternatively, any two of $R^1$, $R^2$ and $R^4$ can independently form a morpholinyl;

$R^3$ is fluorine or chlorine; and X is selected from CH or N.

In a preferred embodiment of the present invention, the compound, stereoisomer thereof or pharmaceutically acceptable salt thereof is selected from the following structures:

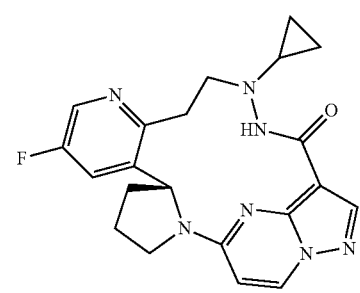
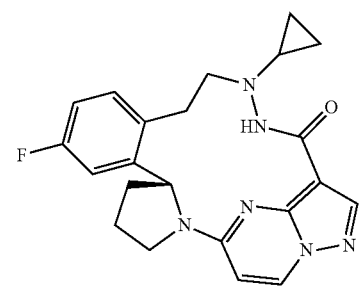
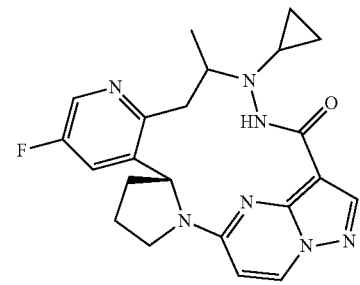
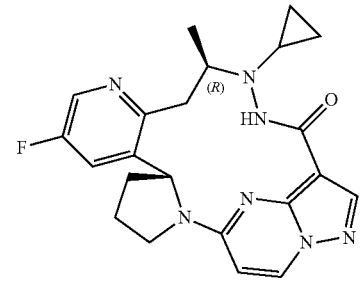
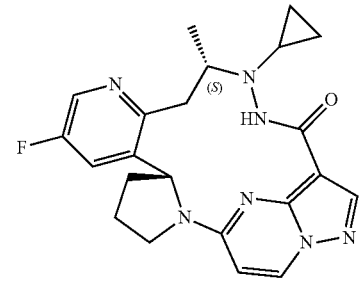
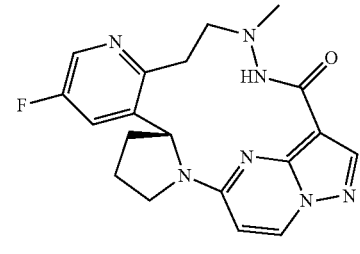
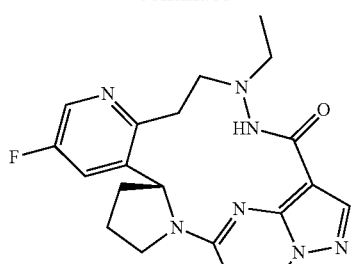
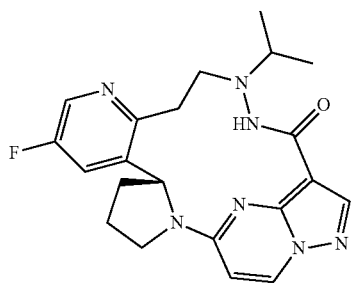
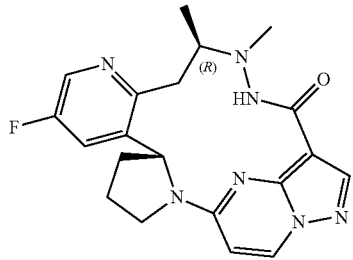
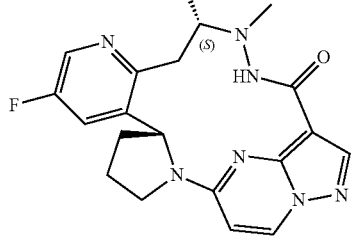
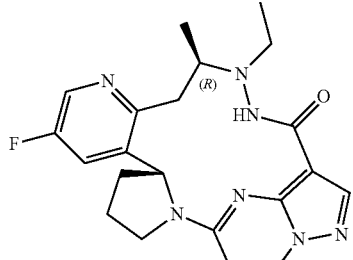
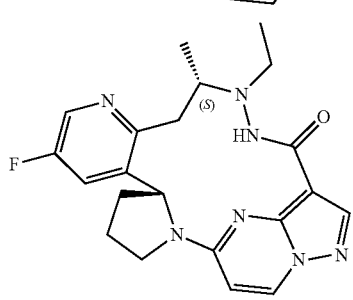

7
-continued
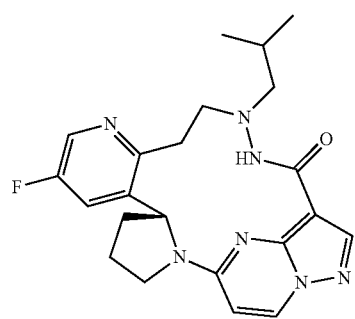
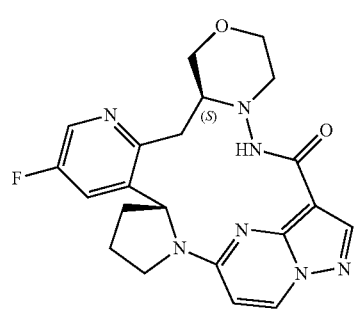
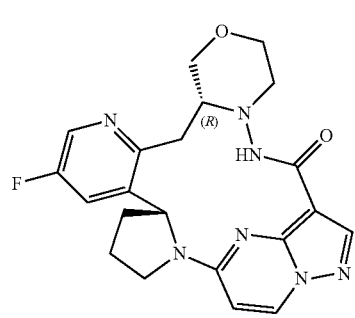
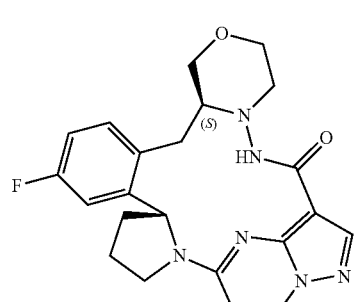
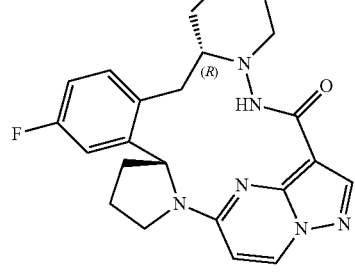
8
-continued
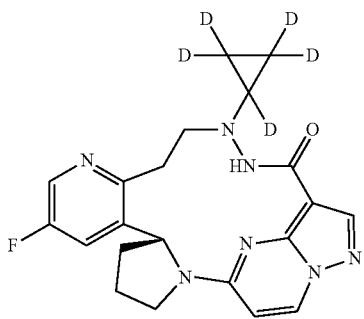
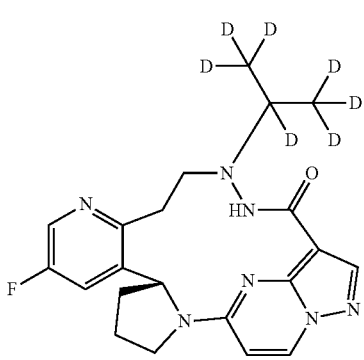
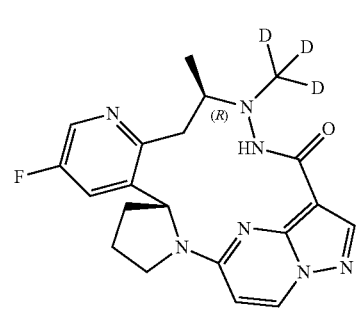
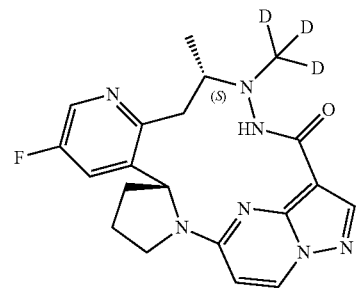
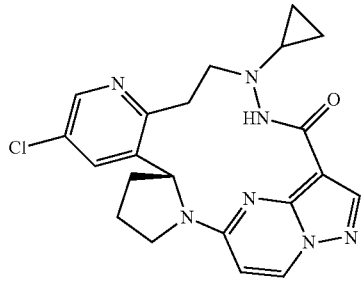

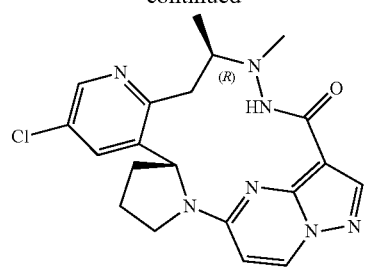
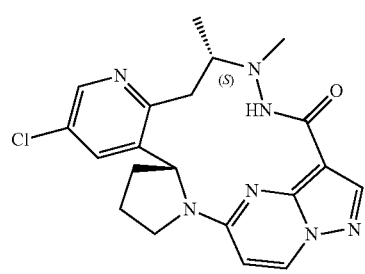
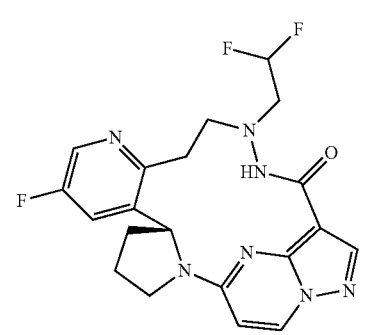
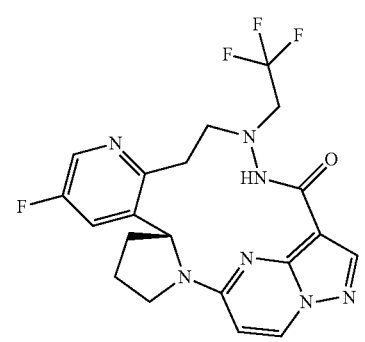
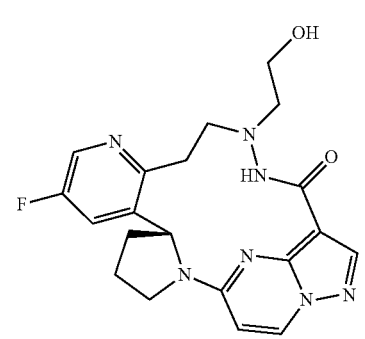
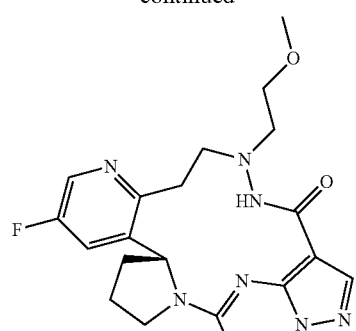
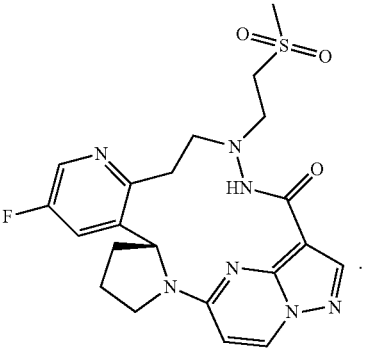
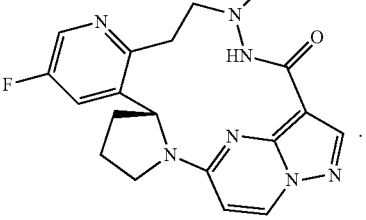
and more preferably, selected from the following structures:
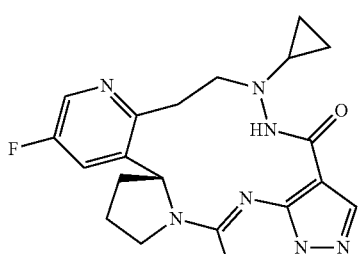
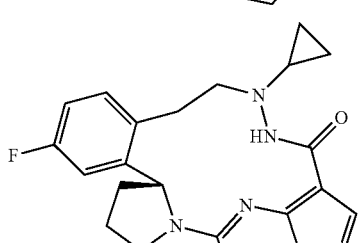
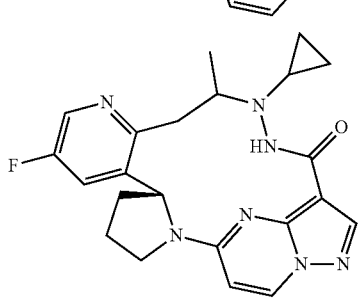

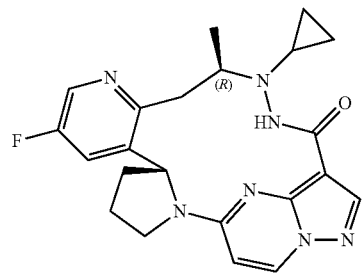

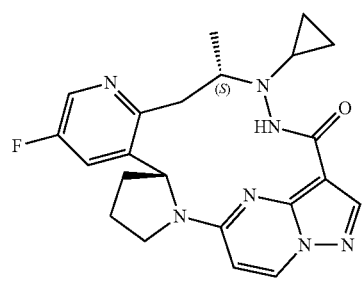

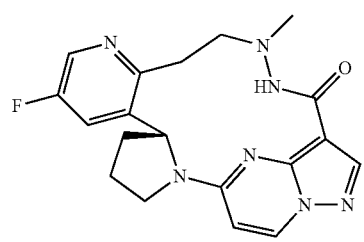

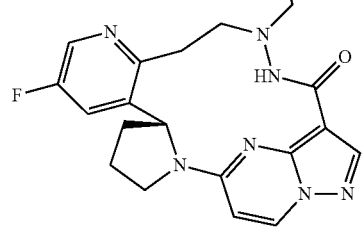

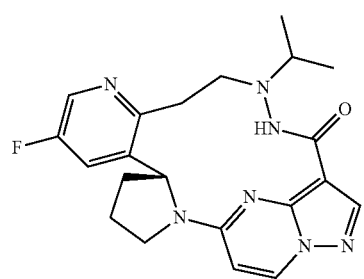

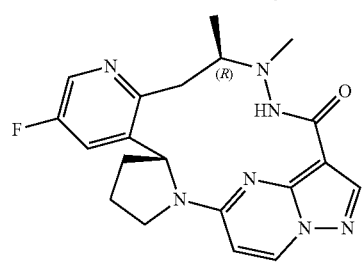

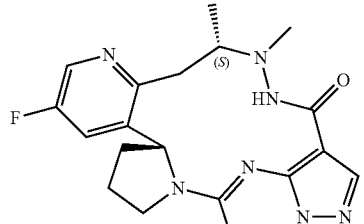

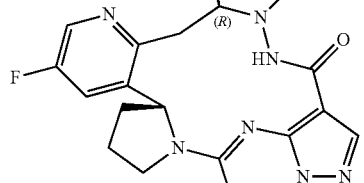

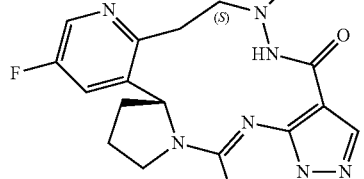

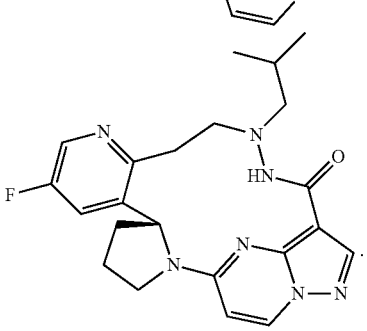

The compound of formula (I), stereoisomer thereof or pharmaceutically acceptable salt thereof according to the present invention is a novel Trk inhibitor, and thus can be used to prepare a medicament for preventing or treating diseases associated with tropomyosin receptor kinases, including but not limited to pain, cancer, and inflammation.

The present invention further provides the use of the compound of formula (I), stereoisomer thereof or pharmaceutically acceptable salt thereof for preventing or treating cancer.

As a further preferred solution, the cancer includes neuroblastoma, ovarian cancer, cervical cancer, colorectal cancer, breast cancer, pancreatic cancer, glioma, glioblastoma, melanoma, prostate cancer, leukemia, lymphoma, non-Hodgkin's lymphoma, gastric cancer, lung cancer, hepatocellular carcinoma, gastrointestinal stromal tumor, thyroid cancer, cholangiocarcinoma, endometrial cancer, renal cancer, anaplastic large cell lymphoma, acute myelocytic leukemia, multiple myeloma, melanoma or mesothelioma, juvenile sarcoma, fibrosarcoma, large cell neuroendocrine carcinoma, pilocytic astrocytoma, head and neck squamous cell carcinoma, congenital mesoblastic nephroma, ductal adenocarcinoma, mammary analogue secretory carcinoma, and appendix cancer.

Another aspect of the present invention provides a pharmaceutical composition comprising a therapeutically effective dose of the compound of formula (I), stereoisomer thereof or pharmaceutically acceptable salt thereof as described above, and a pharmaceutically acceptable carrier.

Another aspect of the present invention provides use of the pharmaceutical composition in the preparation of a medicament for preventing or treating cancer.

Detailed description: Unless stated to the contrary, the following terms used in the description and claims have the following meanings.

In the present invention, "$C_1$-$C_8$ alkyl" refers to a linear alkyl group and a branched alkyl group including 1 to 8 carbon atoms. The alkyl group refers to a saturated aliphatic hydrocarbon group, for example, methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, or various branched isomers thereof, etc.

In the present invention, "cycloalkyl" refers to a saturated monocyclic hydrocarbon substituent, and "$C_3$-$C_8$ cycloalkyl" refers to a monocyclic cycloalkyl including 3 to 8 carbon atoms, and for example, non-limiting examples of the monocyclic cycloalkyl include cyclopropyl, cyclobutyl, cyclopentyl, cyclohexyl, cycloheptyl, cyclooctyl, etc.; "$C_3$-$C_6$ cycloalkyl" refers to a monocyclic cycloalkyl group including 3 to 6 carbon atoms, and for example, non-limiting examples of the monocyclic cycloalkyl include cyclopropyl, cyclobutyl, cyclopentyl, cyclohexyl, etc.

In the present invention, "alkenyl" refers to an alkyl group as defined above consisting of at least two carbon atoms and at least one carbon-carbon double bond, and "$C_2$-$C_8$ alkenyl" refers to a linear or branched alkenyl containing 2-8 carbon atoms. For example, vinyl, 1-propenyl, 2-propenyl, 1-, 2- or 3-butenyl and the like.

In the present invention, "alkynyl" refers to an alkyl group as defined above consisting of at least two carbon atoms and at least one carbon-carbon triple bond, and "$C_2$-$C_8$ alkynyl" refers to a linear or branched alkynyl containing 2-8 carbon atoms. For example, ethynyl, 1-propynyl, 2-propynyl, 1-, 2- or 3-butynyl and the like.

In the present invention, a "heterocyclic group" refers to a saturated or partially unsaturated monocyclic or polycyclic cyclic hydrocarbon substituent, wherein one or more ring atoms are heteroatoms selected from nitrogen, oxygen, or $S(O)r$ (where r is an integer of 0, 1, or 2), excluding —OO—, —OS— or —SS— ring moiety, the remaining ring atoms being carbon atoms. A "4-10 membered heterocyclic group" refers to a cyclic group containing 4 to 10 ring atoms. Non-limiting examples of the monocyclic heterocyclic group include tetrahydropyranyl, dihydropyranyl, pyrrolidinyl, piperidinyl, piperazinyl, morpholinyl, thiomorpholinyl, homopiperazinyl and the like. A polycyclic heterocyclic group includes spiro, fused and bridged heterocyclic groups. In the present invention, "alkoxy" refers to —O-(alkyl), wherein the alkyl is as defined above. "$C_1$-$C_8$ alkoxy" refers to an alkoxy group containing 1-8 carbon atoms, and non-limiting examples thereof include methoxy, ethoxy, propoxy, butoxy and the like.

"Halogen" refers to fluorine, chlorine, bromine, or iodine.

A "pharmaceutical composition" means a mixture containing one or more compounds described herein or physiologically acceptable salts or prodrugs thereof with other chemical components, as well as other components such as physiologically acceptable carriers and excipients. The purpose of the pharmaceutical composition is to promote the administration to an organism and facilitate the absorption of an active ingredient to exert its biological activity.

In the preparation steps of the present invention, the abbreviations of the reagents used respectively indicate:
MTBE methyl tert-butyl ether
Sec-BuLi sec-butyl lithium
THF tetrahydrofuran
Pd2(dba)3 tris(dibenzylideneacetone)dipalladium
t-Bu3P—HBF4 tri-n-butylphosphonium tetrafluoroborate
Hexane n-hexane
EA ethyl acetate
DCM dichloromethane
DIEA N,N-diisopropylethylamine
DMF N,N-dimethylformamide
TEA triethylamine
(Ph3P)2PdCl2 bis(triphenylphosphine)palladium dichloride
HOBt 1-hydroxybenzotriazole
EDCI 1-(3-dimethylaminopropyl)-3-ethylcarbodiimide hydrochloride

BRIEF DESCRIPTION OF THE DRAWINGS

FIG. 3 is the 1H NMR spectrum of a compound of Example 3a;
FIG. 8 is the 1H NMR spectrum of a compound of Example 7a;
FIG. 10 is the 1H NMR spectrum of a compound of Example 8a.

DETAILED DESCRIPTION OF THE INVENTION

Figure 1:
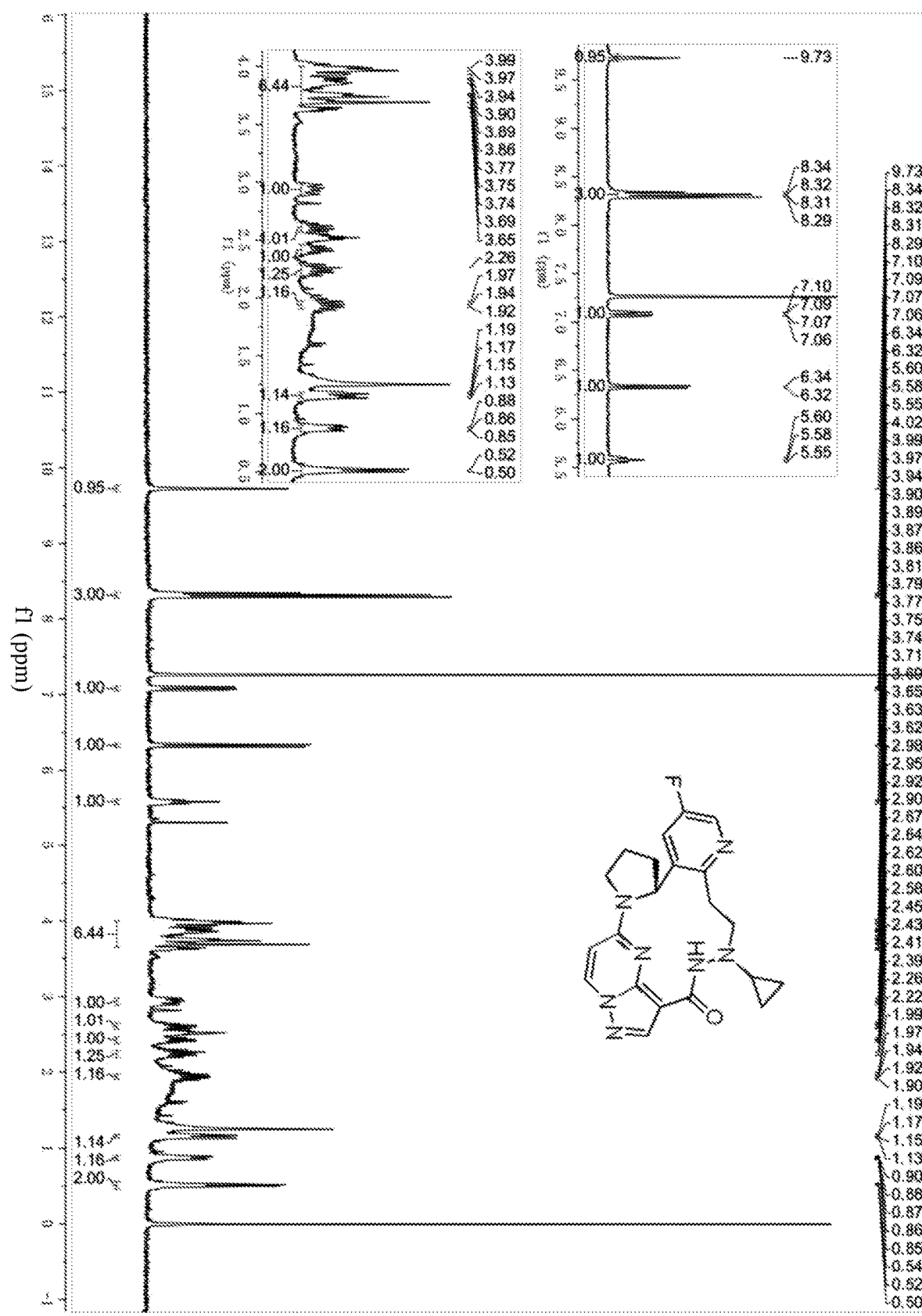
FIG. 1 is the 1H NMR spectrum of a compound of Example 1.
Figure 2:
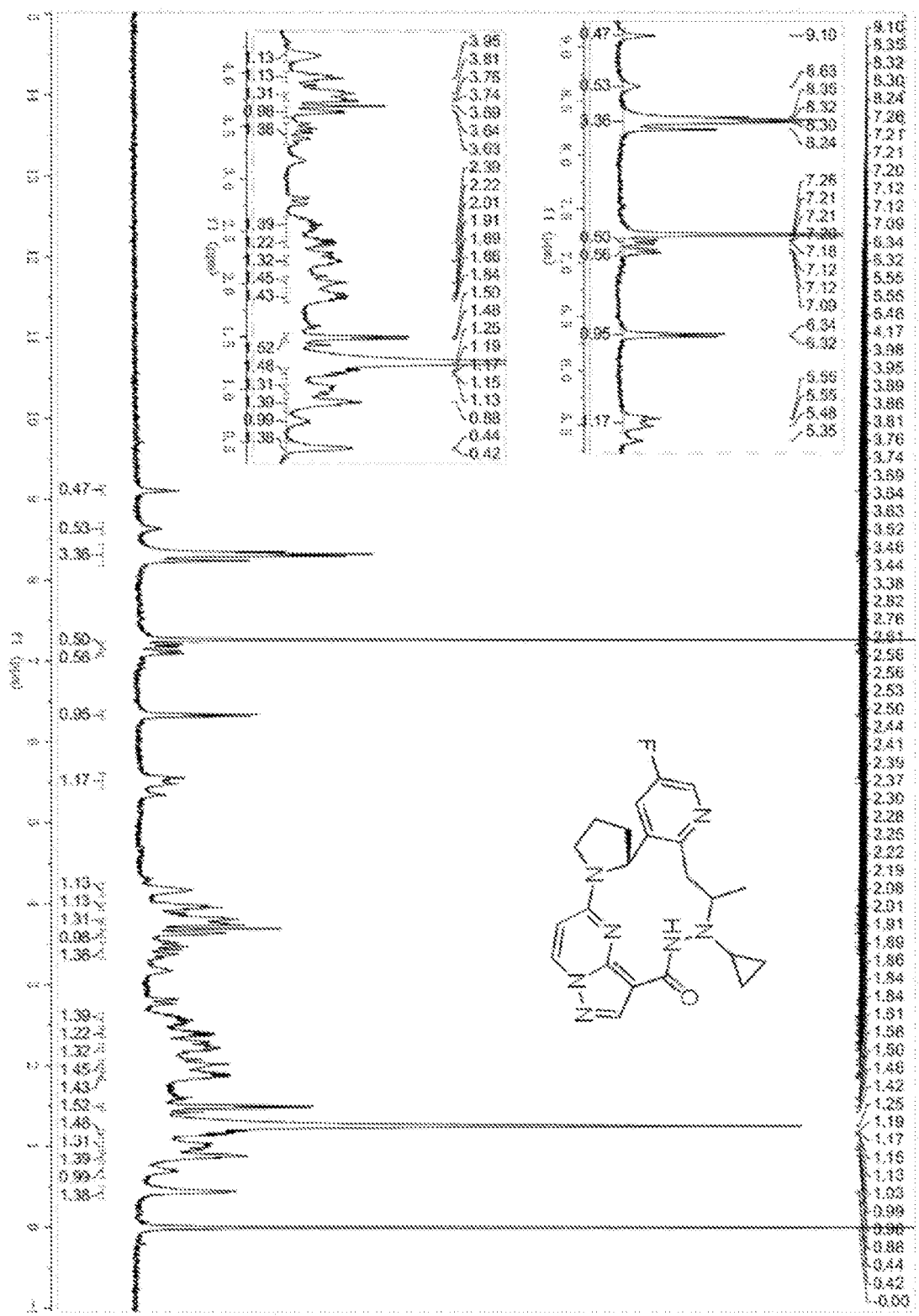
FIG. 2 is the 1H NMR spectrum of a compound of Example 2.
Figure 3:
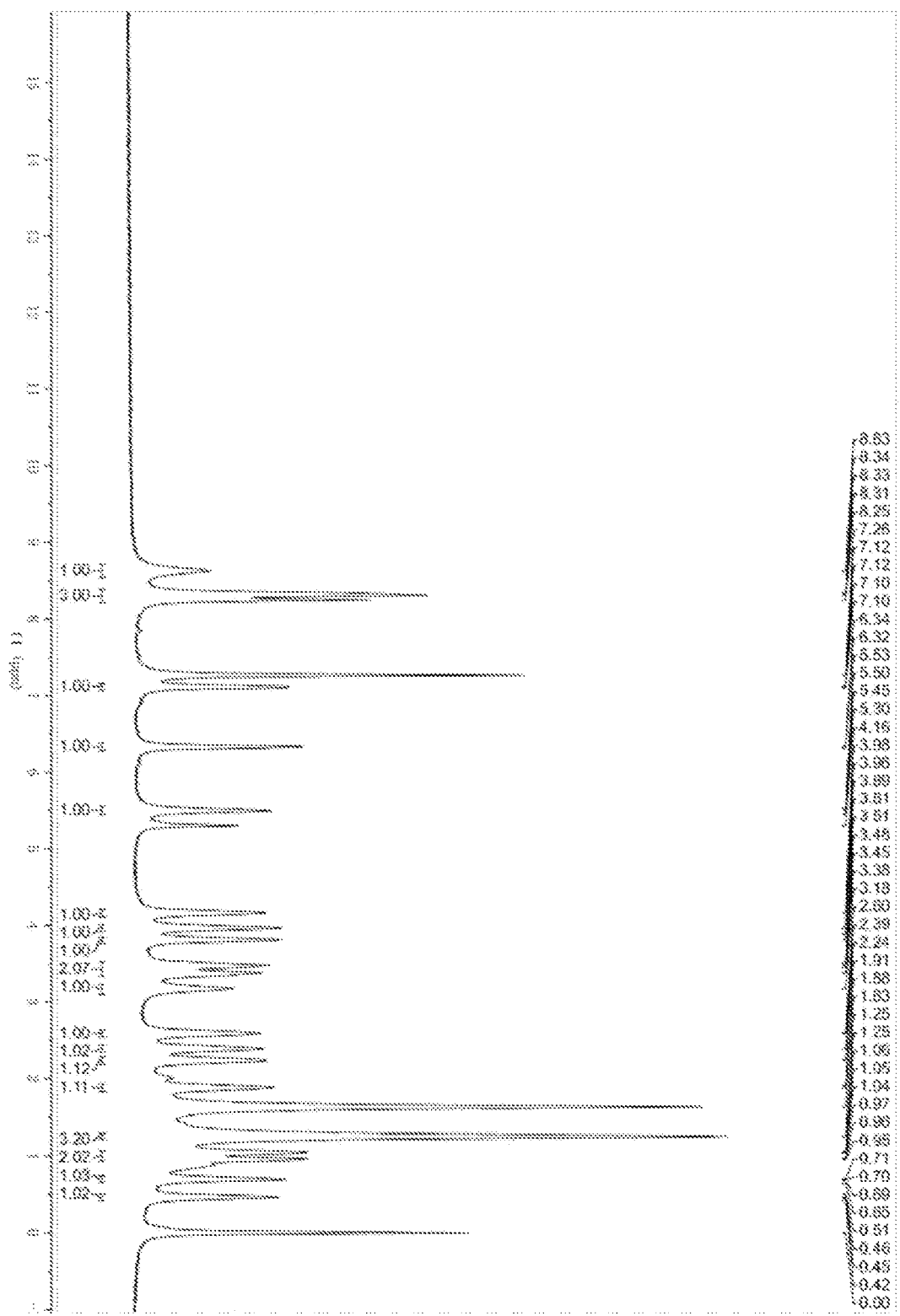
Figure 4:
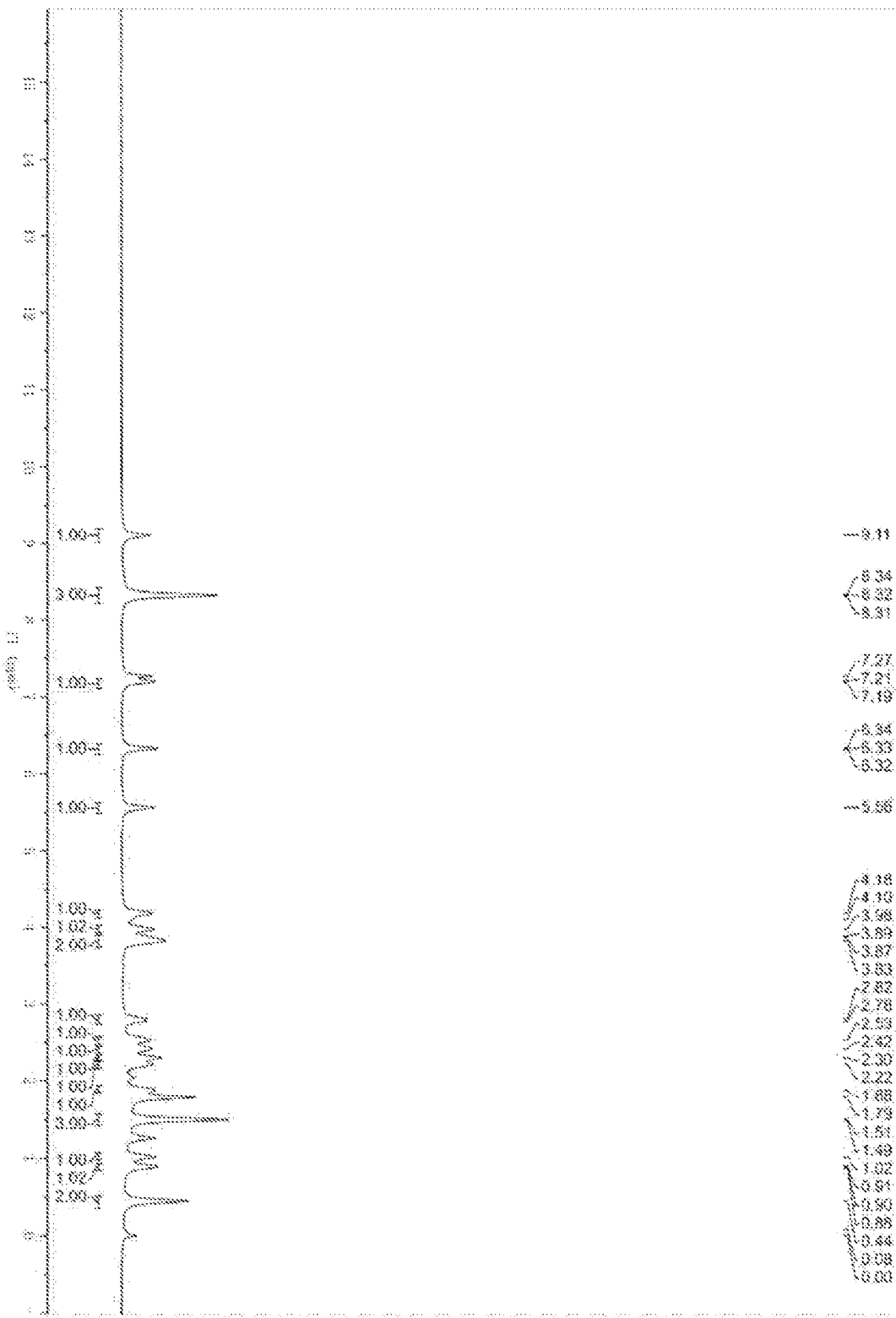
FIG. 4 is the 1H NMR spectrum of a compound of Example 3b.
Figure 5:
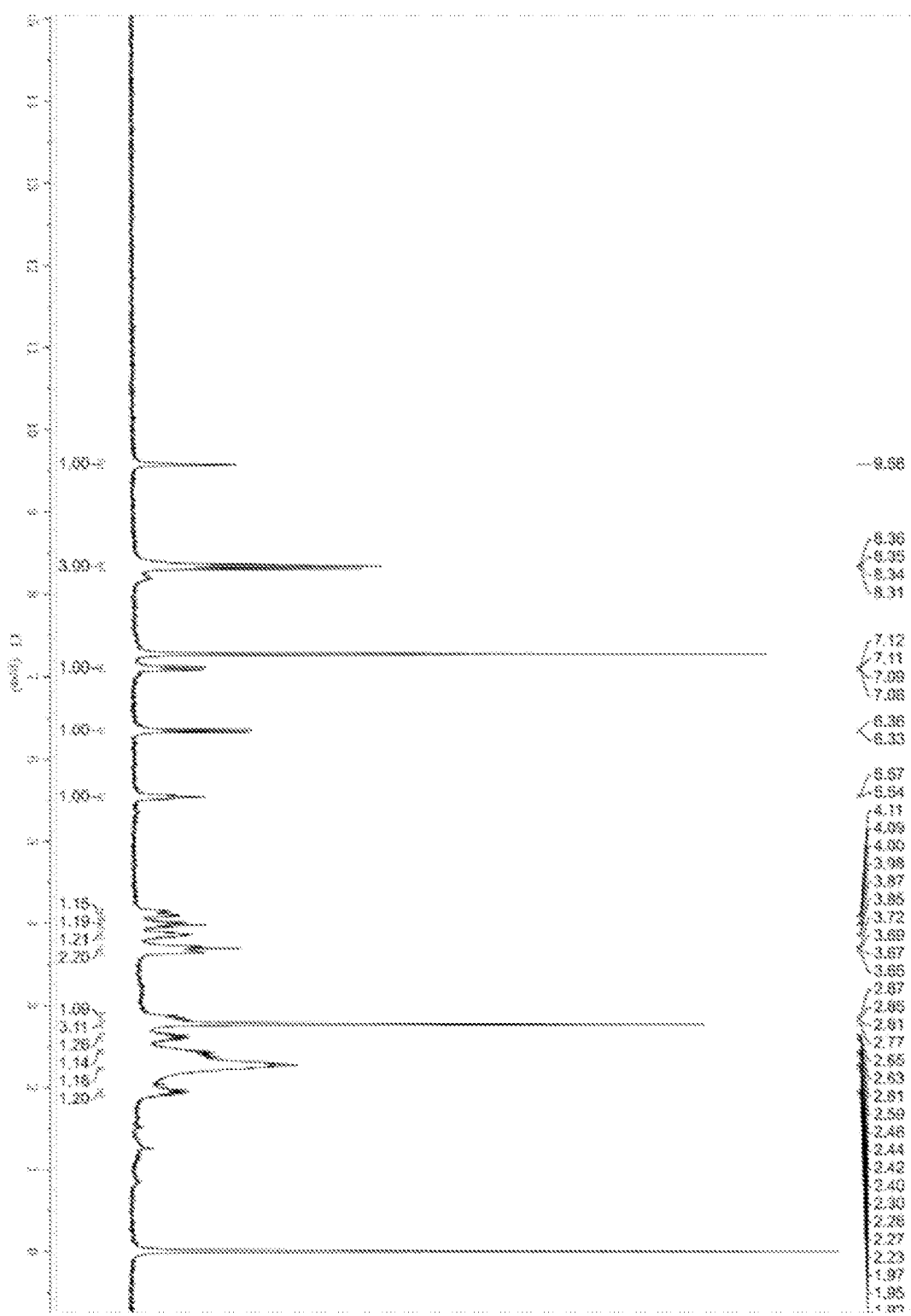
FIG. 5 is the 1H NMR spectrum of a compound of Example 4.
Figure 6:
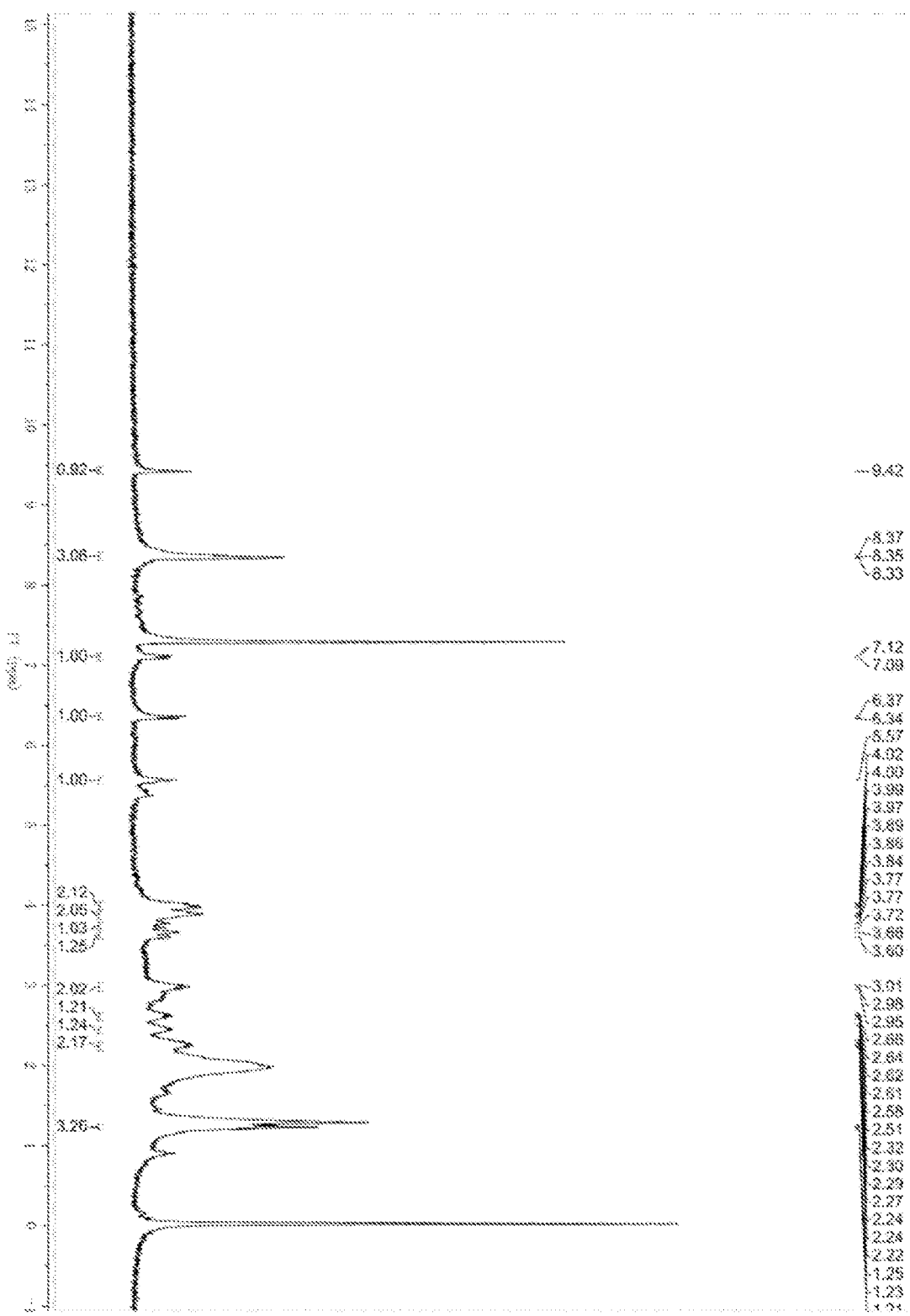
FIG. 6 is the 1H NMR spectrum of a compound of Example 5.
Figure 7:
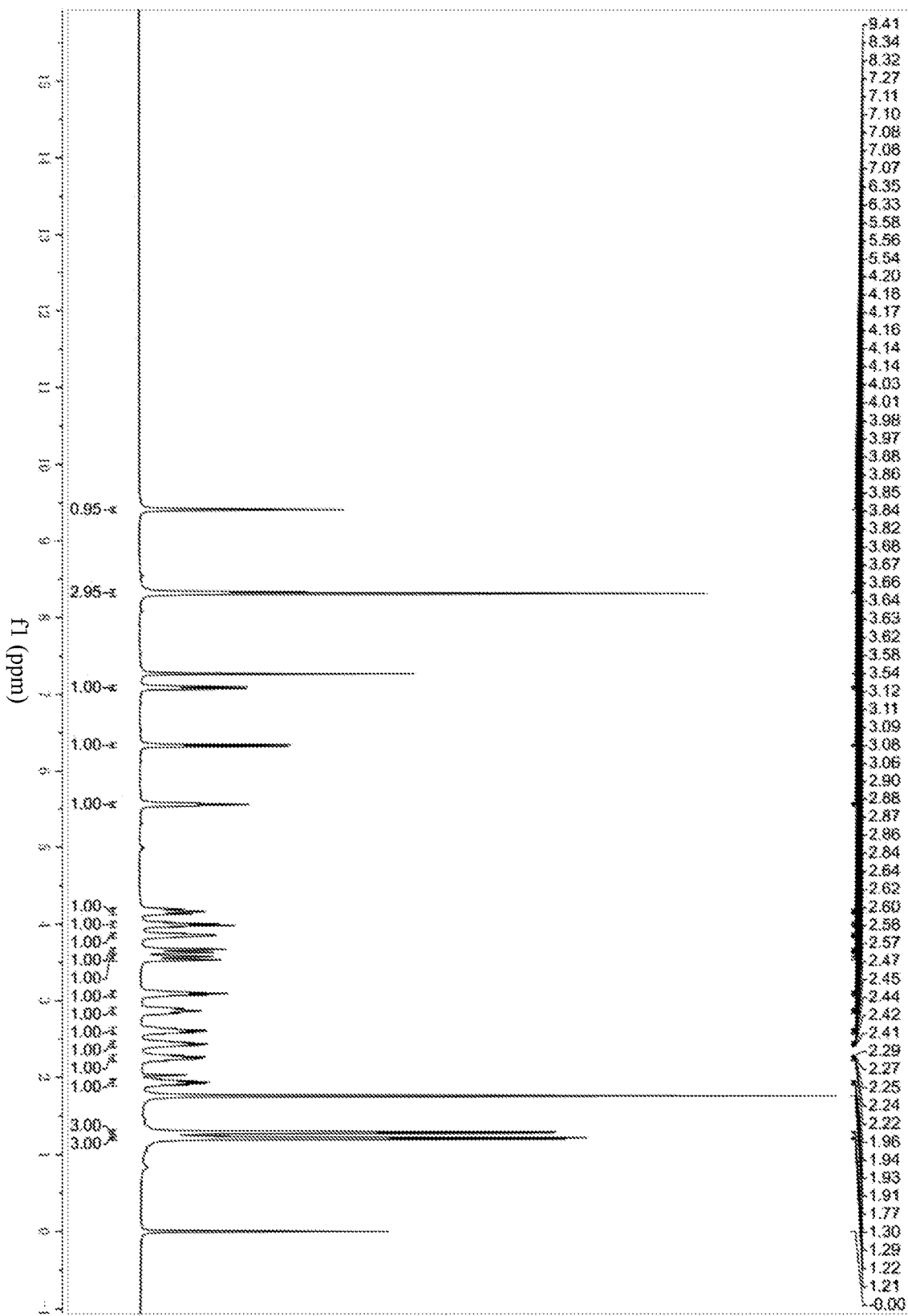
FIG. 7 is the 1H NMR spectrum of a compound of Example 6.
Figure 8:
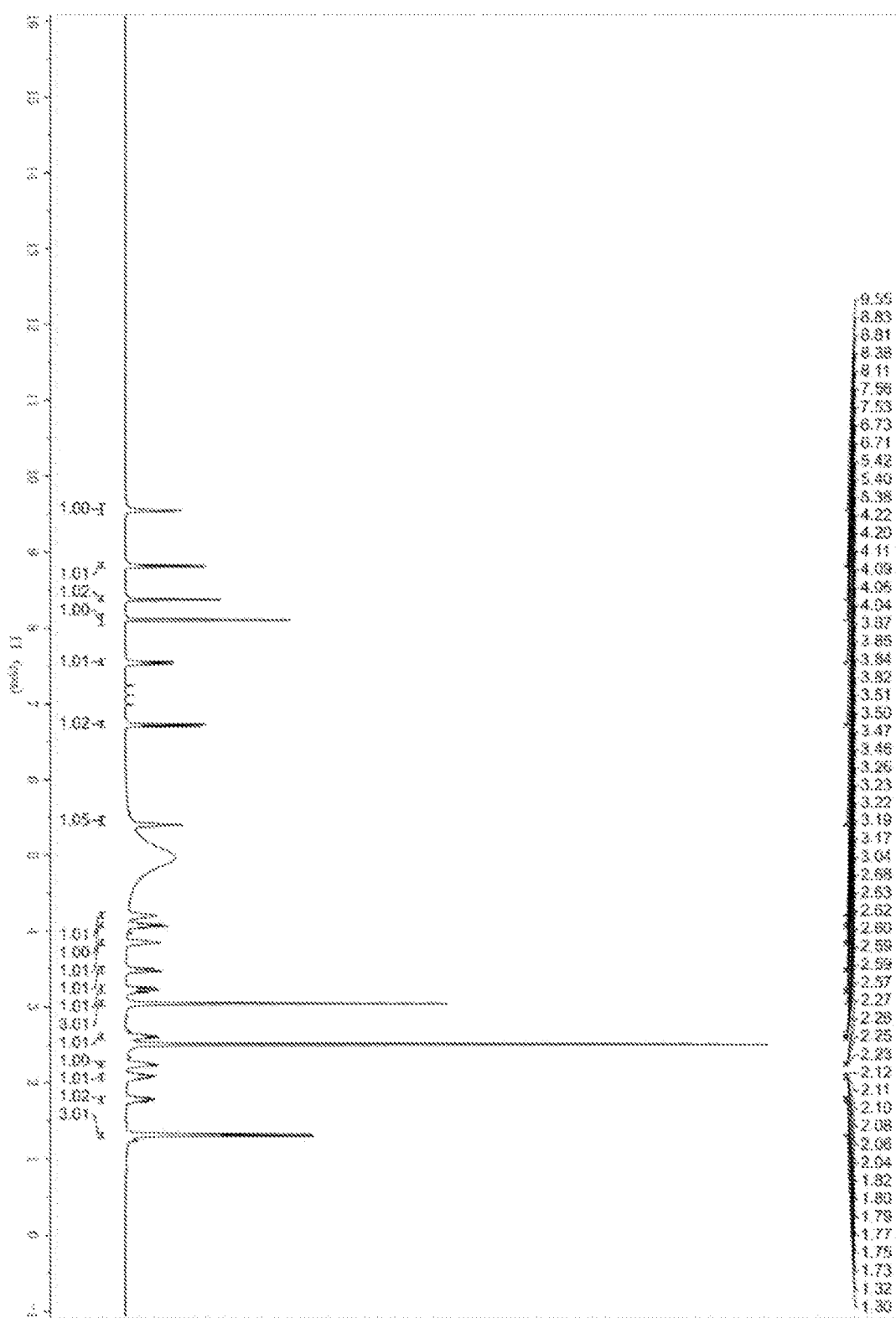
Figure 9:
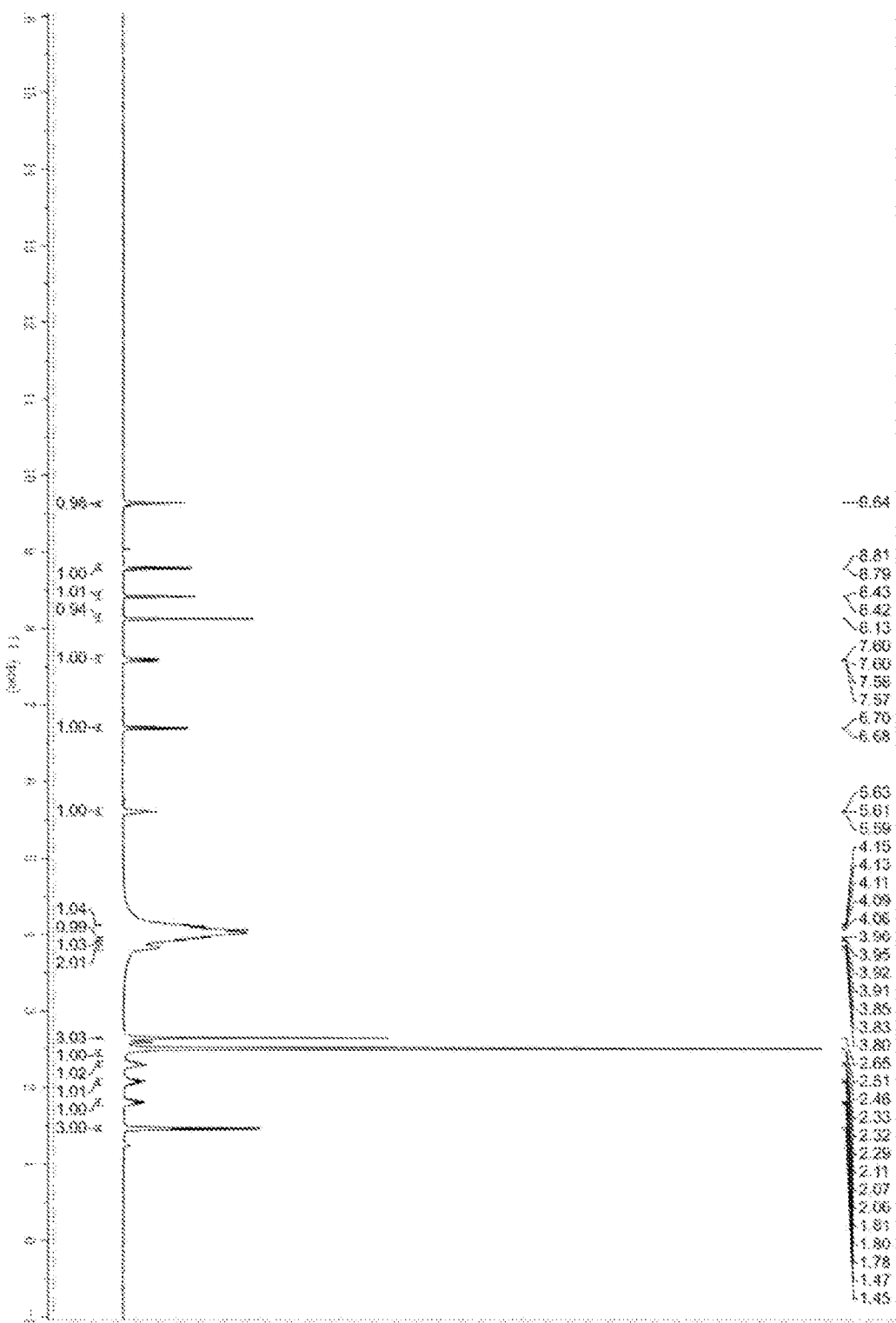
FIG. 9 is the 1H NMR spectrum of a compound of Example 7b.
Figure 10:
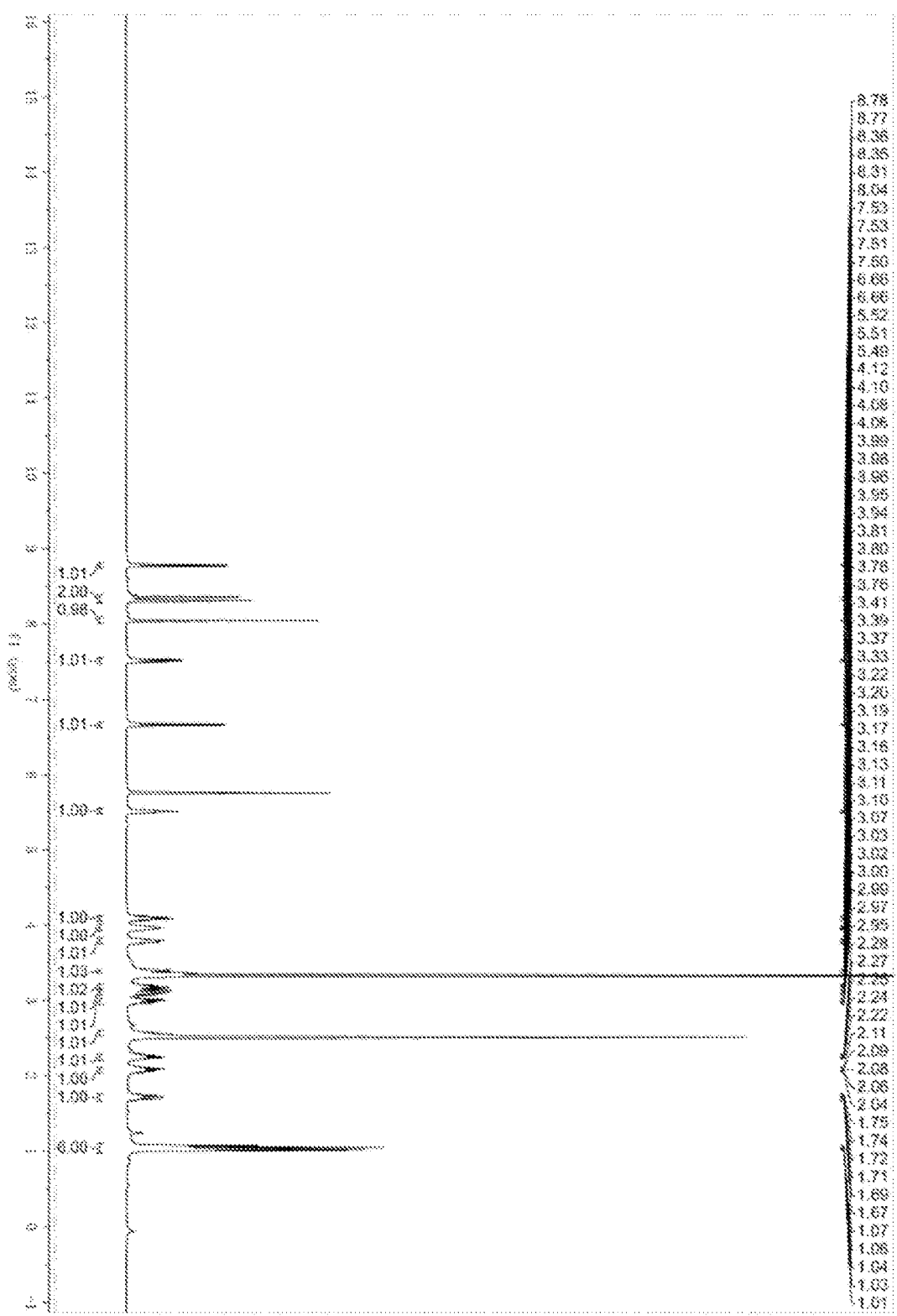
Figure 11:
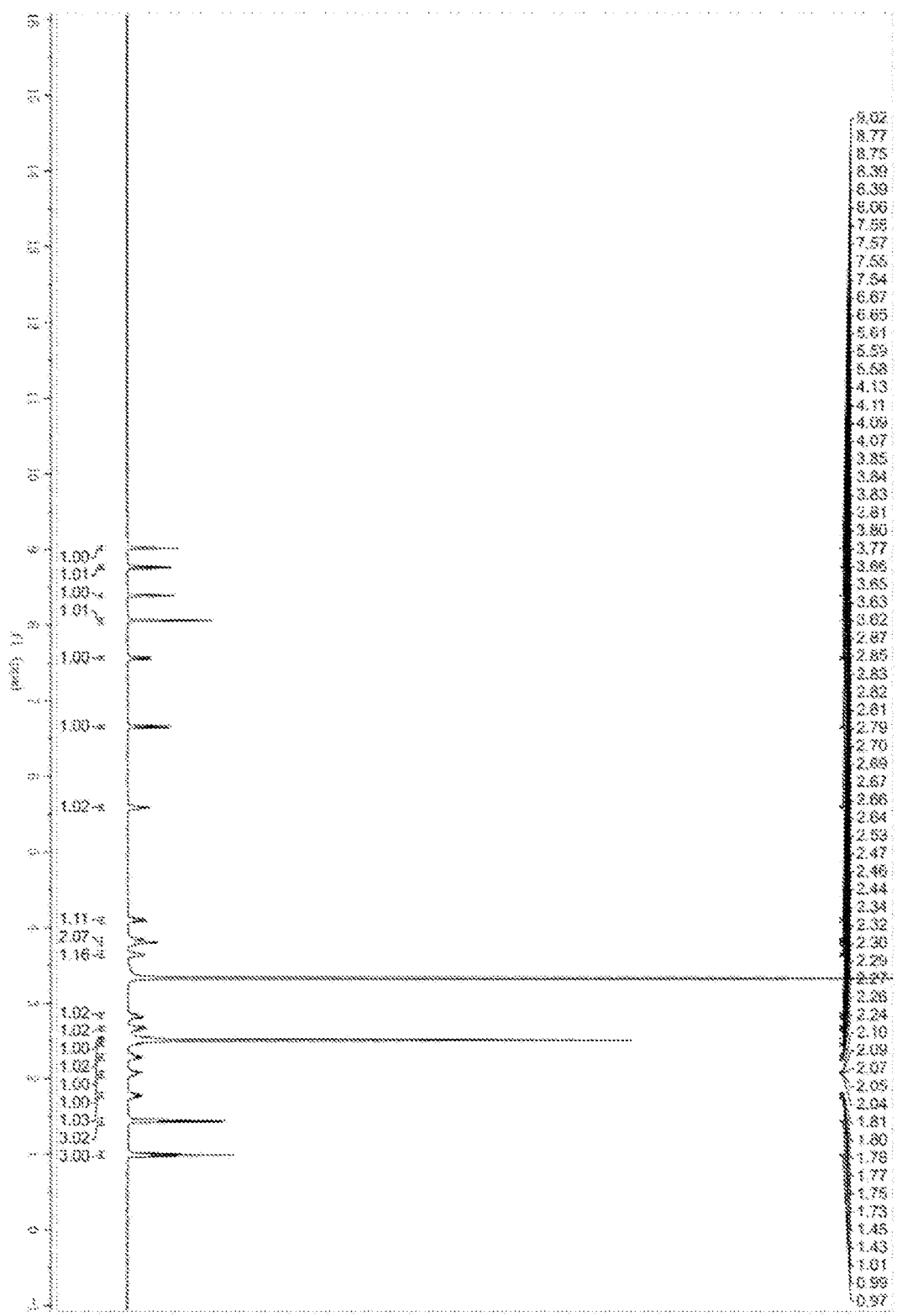
FIG. 11 is the 1H NMR spectrum of a compound of Example 8b.
Figure 12:
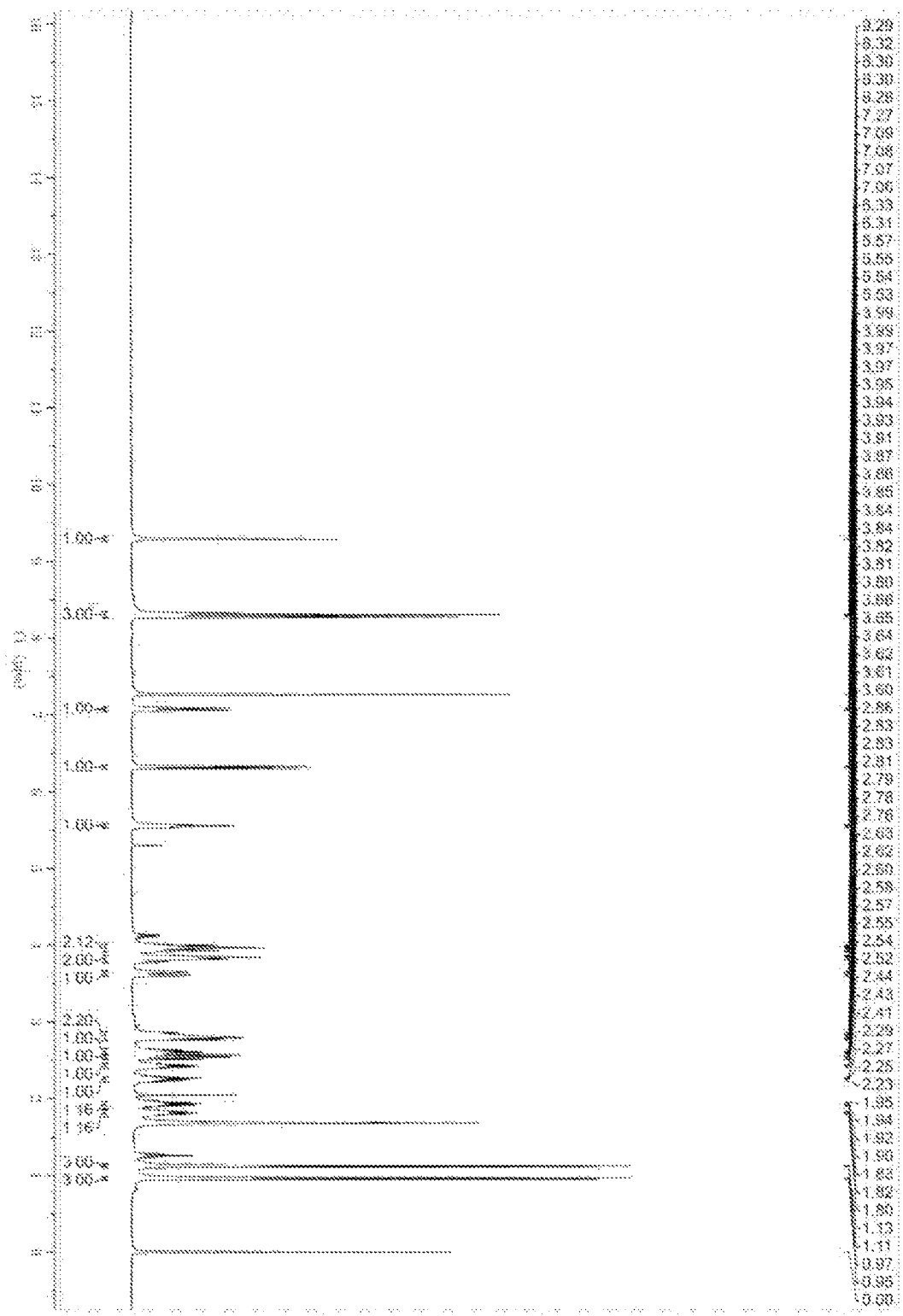
FIG. 12 is the 1H NMR spectrum of a compound of Example 9.
Figure 13:
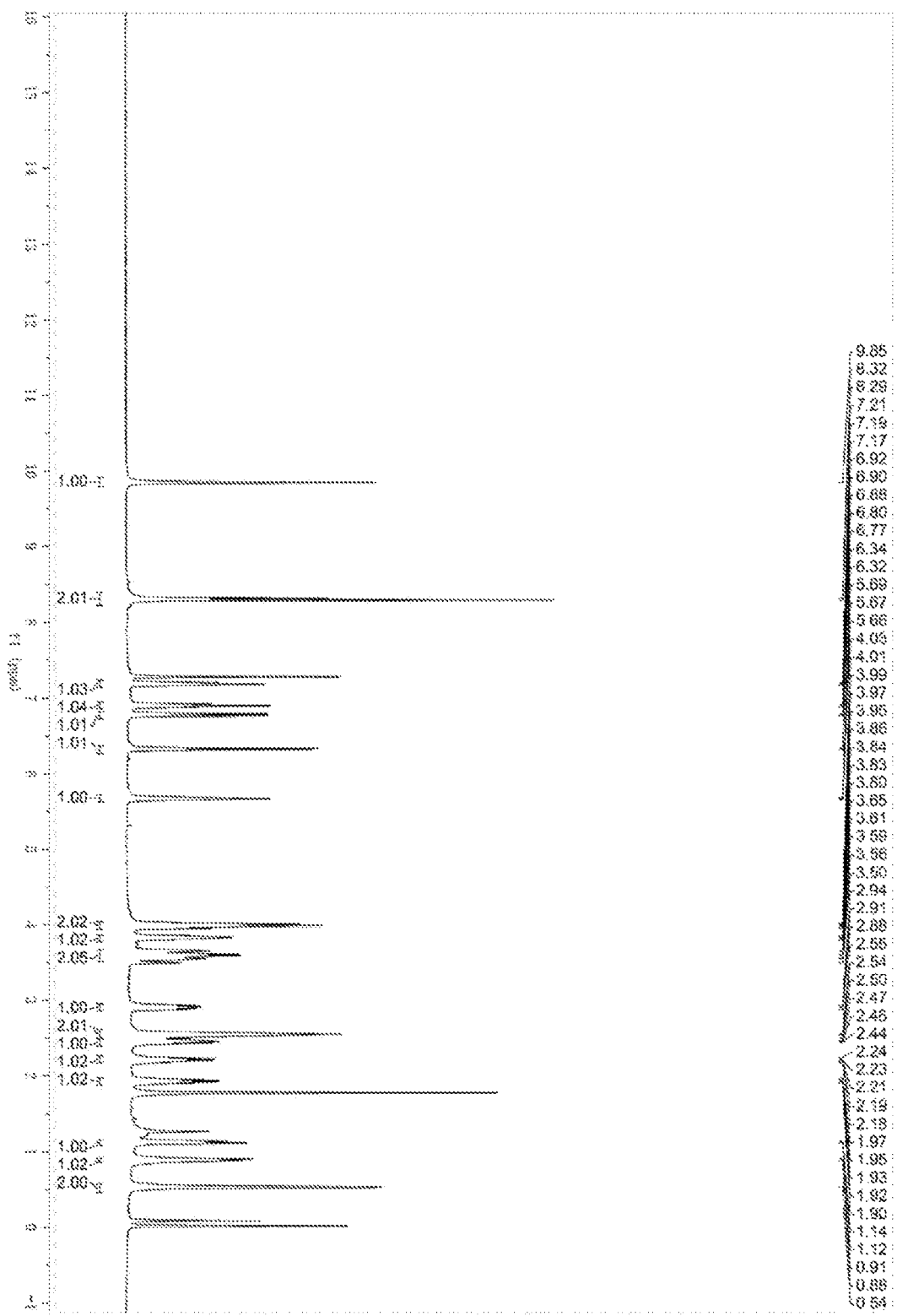
FIG. 13 is the 1H NMR spectrum of a compound of Example 10.

The present invention will be described below with reference to specific examples. Those skilled in the art can understand that these examples are only used for illustrating the present invention and are not intended to limit the scope of the present invention in any way.

The experimental methods in the examples below are conventional methods, unless otherwise specified. Medicinal raw materials and reagent materials used in the examples below are commercially available products, unless specifically stated.

Example 1

(R,I³E,I⁴E)-6-cyclopropyl-3⁵-fluoro-6,7-diazepine-1(5,3)-pyrazolo[1,5-a]pyrimidine-3(3,2)-pyridine-2(1,2)-pyrrolidine cyclooctane-8-one Step 1: Synthesis of (R)-tert-butyl 2-(5-fluoro-2-methoxypyridin-3-yl)pyrrolidine-1-carboxylate

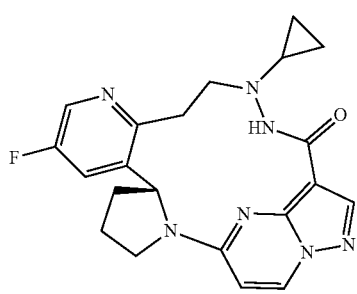 [SMILES: O=C1NN(C2CC2)CCc2ncc(F)cc2[C@H]2CCCN2c2ccn3ncc1c3n2]

At room temperature, tert-butyl pyrrolidine-1-carboxylate (2.86 mL, 16.03 mmol), (−)-Sparteine (4.50 g, 19.20 mmol) and MTBE (35.0 mL) were added into a 250 mL three-necked flask. The atmosphere in the flask was replaced with nitrogen for three times, and the temperature was lowered slowly to −78° C. Sec-BuLi (17.01 mL, 21.70 mmol, 1.3N in cyclohexane) was added dropwise after the temperature was stabilized, and stirred at −75° C. for 3 hours. ZnCl₂ (14.68 mL, 14.36 mmol, 1 N in THF) was slowly added dropwise at −65° C., and stirred for 20 minutes after the temperature was lowered to around −78° C. The temperature was increased to room temperature, and under the protection of nitrogen, 3-bromo-5-fluoro-2-methoxypyridine (3.44 g, 16.70 mmol), Pd(OAc)₂ (0.18 g, 0.84 mmol), and t-Bu₃P—HBF₄ (0.28 g, 1.00 mmol) were sequentially added. After the addition was completed, the reaction was carried out at room temperature for 16 hours. 1.50 mL ammonia water was added dropwise to the reaction system and stirred at room temperature for 1 hour. The reaction solution was filtered through celite, washed with MTBE (20 mL×3), and separated. The organic phase was concentrated and subjected to column chromatography (Hexane:EA=20:1). After concentration under reduced pressure, 2.60 g of a yellow oil was obtained, with a yield of 52.53%. ¹H NMR (400 MHz, Chloroform-d) δ 7.84 (d, J=7.2 Hz, 1H), 7.09 (dd, J=29.5, 6.1 Hz, 1H), 4.99 (dd, J=52.8, 8.0 Hz, 1H), 3.93 (s, 3H), 3.53 (m, 2H), 2.28 (m, 1H), 1.82 (m, 3H), 1.46 (s, 9H).

Step 2: Synthesis of (R)-5-fluoro-2-methoxy-3-(pyrrolidin-2-yl)pyridine

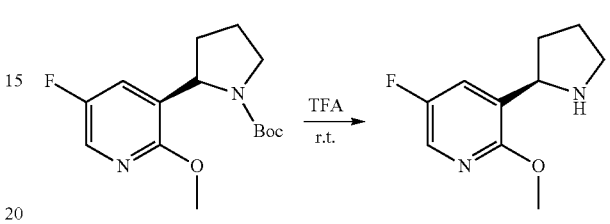

At room temperature, (R)-tert-butyl 2-(5-fluoro-2-methoxypyridin-3-yl)pyrrolidine-1-carboxylate (2.60 g, 8.77 mmol), trifluoroacetic acid (7.80 mL) and dichloromethane (7.80 mL) were sequentially added into a 100 mL single-necked flask, and stirred at room temperature for 1.5 hours. After the raw materials were completely reacted, the reaction was stopped. The reaction solution was evaporated to dryness under reduced pressure to obtain a yellow oil of 3.94 g, which was directly used in the next reaction step.

Step 3: Synthesis of (R)-ethyl 5-(2-(5-fluoro-2-methoxypyridin-3-yl)pyrrolidin-1-yl)pyrazolo[1,5-a]pyrimidine-3-carboxylate

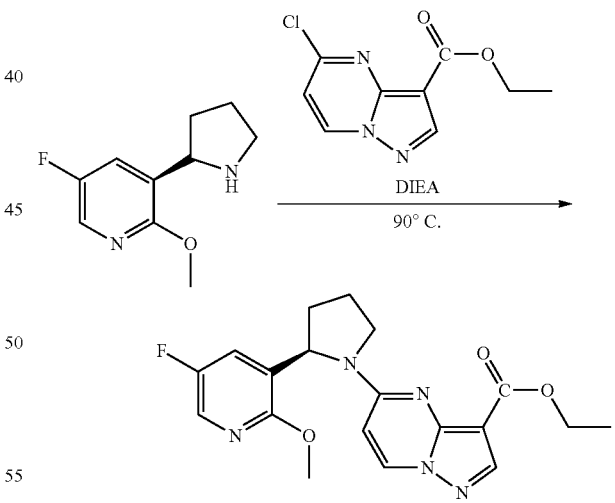

At room temperature, (R)-5-fluoro-2-methoxy-3-(pyrrolidin-2-yl)pyridine (1.72 g, 8.78 mmol), ethyl 5-chloropyrazolo[1,5-a]pyrimidine-3-carboxylate (2.38 g, 10.54 mmol), DIEA (5.25 g, 40.65 mmol), and DMF (19.30 mL) were added into a 30 mL microwave sealed tube, slowly warmed to 90° C., and reacted with stirring for 15.5 h. After the reaction was cooled, it was dissolved and dispersed by adding EA (100 mL), washed by adding water (100 mL), and separated. The organic phase was washed sequentially with saturated brine (100 mL) and a saturated aqueous solution of sodium bicarbonate (100 mL), dried over anhydrous sodium sulfate, and evaporated to dryness under reduced pressure. Column chromatography (PE:EA=1:1) was performed to obtain a yellow solid of 1.83 g. MS (ESI) m/z: 386[M+H]⁺. ¹H NMR (400 MHz, Chloroform-d) δ 8.28 (s, 1H), 8.15 (d, J=5.2 Hz, 1H), 7.91 (s, 1H), 7.04 (d, J=7.2 Hz, 1H), 5.84 (d, J=4.5 Hz, 1H), 5.09 (m, 1H), 4.37 (m, 2H), 4.18-4.11 (m, 1H), 4.02 (s, 3H), 3.96 (m, 1H), 2.47 (m, 1H), 2.04 (m, 2H), 1.95 (m, 1H), 1.42 (m, 3H).

Step 4: Synthesis of (R)-ethyl 5-(2-(5-fluoro-2-hydroxypyridin-3-yl)pyrrolidin-1-yl)pyrazolo [1,5-a] pyrimidine-3-carboxylate

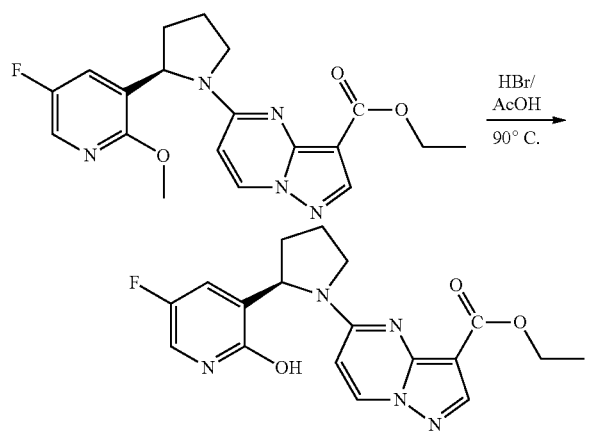

At room temperature, (R)-ethyl 5-(2-(5-fluoro-2-methoxypyridin-3-yl)pyrrolidin-1-yl)pyrazolo[1,5-a]pyrimidine-3-carboxylate (1.83 g, 4.75 mmol), HBr (18.30 mL, 33% in AcOH) were added into a 100 mL single-necked flask, slowly warmed to 90° C., and reacted with stirring for 4.5 hours. The reaction was dissolved and dispersed by adding EA (100 mL), washed by adding water (100 mL), and separated. The organic phase was washed sequentially with a saturated NaHCO₃ solution (100 mL) and saturated brine (100 mL), dried over anhydrous sodium sulfate, and evaporated to dryness under reduced pressure. Column chromatography (DCM:EtOH=20:1) was performed to obtain a yellow solid of 1.34 g. MS (ESI) m/z: 372[M+H]⁺. ¹H NMR (400 MHz, Chloroform-d) δ 12.92 (br, 1H), 8.29 (s, 1H), 8.21 (d, J=7.5 Hz, 1H), 7.30 (s, 1H), 7.17 (s, 1H), 6.93 (d, J=4.7 Hz, 1H), 5.13 (m, 1H), 4.37 (q, J=8.7 Hz, 2H), 4.16 (m, 1H), 3.95 (m, 1H), 2.49 (m, 1H), 2.13-2.07 (m, 2H), 1.95 (m, 1H), 1.42 (t, J=8.8 Hz, 3H).

Step 5: Synthesis of (R)-ethyl 5-(2-(5-fluoro-2-(trifluoromethyl-sulfonyloxy)pyridin-3-yl)pyrrolidin-1-yl)pyrazolo[1,5-a]pyrimidine-3-carboxylate

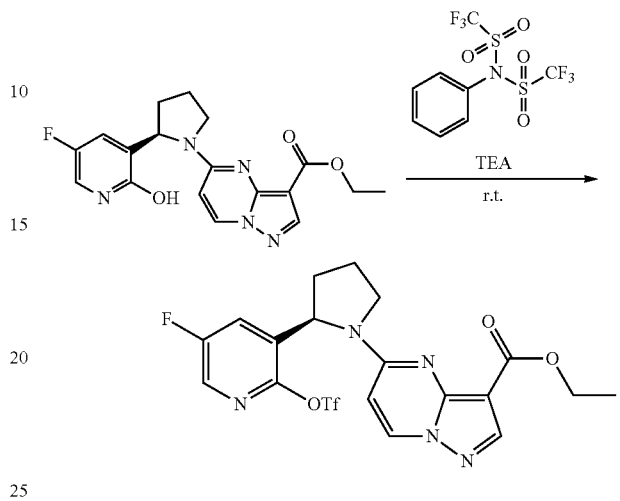

At room temperature, (R)-ethyl 5-(2-(5-fluoro-2-hydroxypyridin-3-yl)pyrrolidin-1-yl)pyrazolo[1,5-a]pyrimidine-3-carboxylate (1.34 g, 3.61 mmol) and DMF (13.0 mL) were added into a 100 mL single-necked flask, and ultrasonically dispersed to be completely dissolved. 1,1,1-trifluoro-N-phenyl-N-((trifluoromethyl)sulfonyl)methylsulfonamide (1.42 g, 3.97 mmol) and TEA (0.44 g, 4.33 mmol) were sequentially added to the reaction system and reacted with stirring at room temperature for 24 hours. EA (110 mL) was added to the reaction system. The reaction system was washed sequentially with a saturated NaHCO₃ solution (100 mL), water (100 mL) and saturated brine (100 mL), dried over anhydrous sodium sulfate, and evaporated to dryness under reduced pressure. Column chromatography (PE:EA=1:1) was performed to obtain a foamy white solid of 1.60 g. MS (ESI) m/z: 504.0[M+H]⁺. ¹H NMR (400 MHz, DMSO-d₆) δ 8.78 (d, J=7.8 Hz, 1H), 8.37 (s, 1H), 8.17 (s, 1H), 7.93 (d, J=8.8 Hz, 1H), 6.69 (d, J=7.8 Hz, 1H), 5.37 (m, 1H), 4.08 (m, 1H), 4.04 (q, J=7.2 Hz, 2H), 3.65 (m, 1H), 2.08 (m, 3H), 1.91 (m, 1H), 1.11 (t, J=7.2 Hz, 3H).

Step 6: Synthesis of ethyl (S)-5-(2-(5-fluoro-2-vinylpyridin-3-yl)pyrrolidin-1-yl)pyrazolo[1,5-a]pyrimidine-3-carboxylate

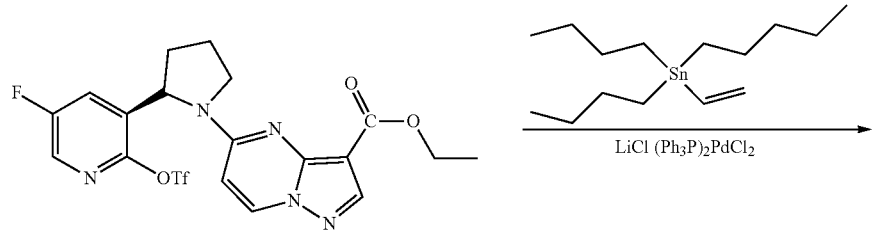

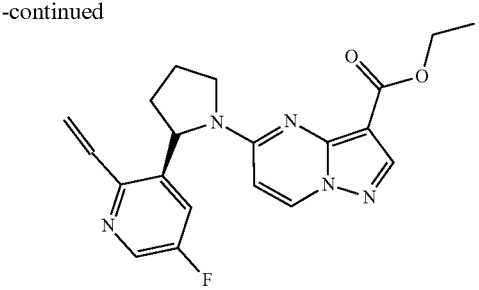

At room temperature, (R)-ethyl 5-(2-(5-fluoro-2-(trifluoromethyl-sulfonyloxy)pyridin-3-yl)pyrrolidin-1-yl)pyrazolo[1,5-a]pyrimidine-3-carboxylate (1.75 g, 3.47 mmol), tributyl(vinyl)tin (1.73 g, 5.21 mmol), lithium chloride (0.74 g, 17.38 mmol), (Ph₃P)₂PdCl₂ (0.24 g, 0.34 mmol), and DMF (35.0 mL) were sequentially added into a 100 mL single-necked flask, replaced with nitrogen for three times, slowly warmed to 80° C., and reacted with stirring for for 4 hours. The reaction solution was cooled to room temperature, sequentially washed with a saturated NaHCO₃ solution (100 mL), water (100 mL) and saturated brine (100 mL), dried over anhydrous sodium sulfate, and evaporated to dryness under reduced pressure. Column chromatography (PE:EA=1:1) was performed to obtain a white solid of 1.23 g. MS (ESI) m/z: 382.0[M+H]⁺. ¹H NMR (400 MHz, Chloroform-d) δ 8.36 (s, 1H), 8.29 (s, 1H), 8.16 (br, 1H), 7.05 (br, 2H), 6.42 (d, J=16.8 Hz, 1H), 5.81-5.53 (m, 2H), 5.20 (m, 1H), 4.36 (m, 2H), 4.11 (q, J=7.2 Hz, 2H), 2.58 (m, 1H), 2.07 (m, 3H), 1.26 (t, J=7.2 Hz, 3H).

Step 7: Synthesis of ethyl (S)-5-(2-(2-(2-(cyclopropylamino)ethyl)-5-fluoropyridin-3-yl)pyrrolidin-1-yl)pyrazolo[1,5-a]pyrimidine-3-carboxylate

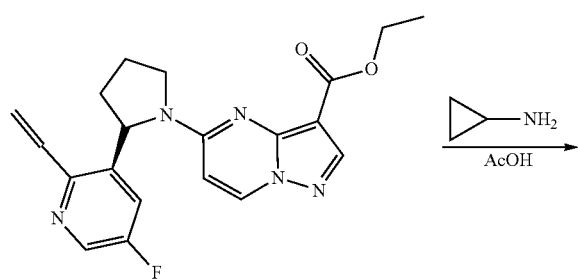

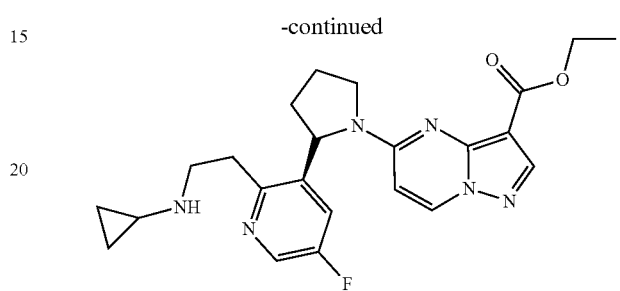

At room temperature, ethyl(S)-5-(2-(5-fluoro-2-vinylpyridin-3-yl)pyrrolidin-1-yl)pyrazolo[1,5-a]pyrimidine-3-carboxylate (1.23 g, 3.22 mmol), cyclopropylamine (5.52 g, 96.75 mmol), glacial acetic acid (5.81 g, 96.75 mmol), and ethanol (12.30 mL) were added into a 100 mL single-necked flask. Under the protection of nitrogen, the temperature was slowly increased to 75° C., and the reaction was carried out under reflux for 20.5 hours. The reaction solution was cooled to room temperature, adjusted to a neutral pH with a saturated aqueous solution of sodium carbonate, and extracted by adding EA (150 mL). The organic phase was dried over anhydrous sodium sulfate, and evaporated to dryness under reduced pressure. Column chromatography (DCM:EtOH=25:1) was performed to obtain a yellow solid of 378.2 mg, with 605.4 mg of the raw materials recovered. The above operations were carried out again on the recovered raw materials, and the products were combined to obtain a yellow solid of 507.2 mg. MS (ESI) m/z: 439.0 [M+H]⁺.

Step 8: Synthesis of ethyl (S)-5-(2-(2-(2-(2-(tert-butylcarbonyl)-1-cyclopropylhydrazino)ethyl)-5-fluoropyridin-3-yl)pyrrolidin-1-yl)pyrazolo[1,5-a]pyrimidine-3-carboxylate

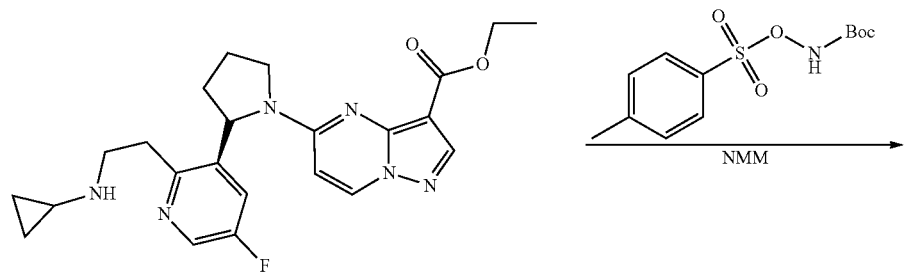

-continued

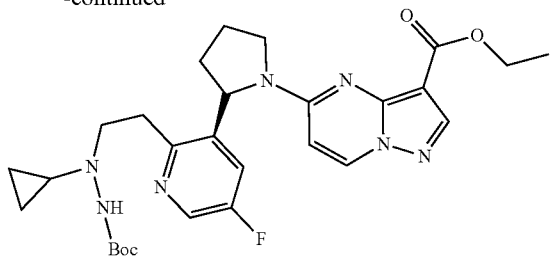

At room temperature, ethyl (S)-5-(2-(2-(2-(cyclopropylamino)ethyl)-5-fluoropyridin-3-yl)pyrrolidin-1-yl)pyrazolo[1,5-a]pyrimidine-3-carboxylate (0.20 g, 0.45 mmol) and tetrahydrofuran (4.0 mL) were added into a 10 mL single-necked flask, ultrasonically dissolved, and cooled to 0° C. N-Boc-O-p-toluenesulfonyl-hydroxylamine (131.0 mg, 0.45 mmol) and N-methylmorpholine (22.5 mg, 0.23 mmol) were added. The reaction solution was returned to room temperature and allowed to react with stirring overnight. The reaction solution was diluted with dichloromethane (40 mL), washed with a saturated aqueous solution of sodium bicarbonate (300 mL), and extracted with di chloromethane (40 mL×3). The organic phase was dried over anhydrous $Na_2SO_4$, and evaporated to dryness under reduced pressure. Column chromatography (PE:EA=1:1) was performed to obtain a yellow solid of 100.0 mg. MS (ESI) m/z: 554.0 [M+H]$^+$.

Step 9: Synthesis of(S)-5-(2-(2-(2-(2-(tert-butylcarbonyl)-1-cyclopropylhydrazino)ethyl)-5-fluoropyridin-3-yl)pyrrolidin-1-yl)pyrazolo[1,5-a]pyrimidine-3-carboxylic acid

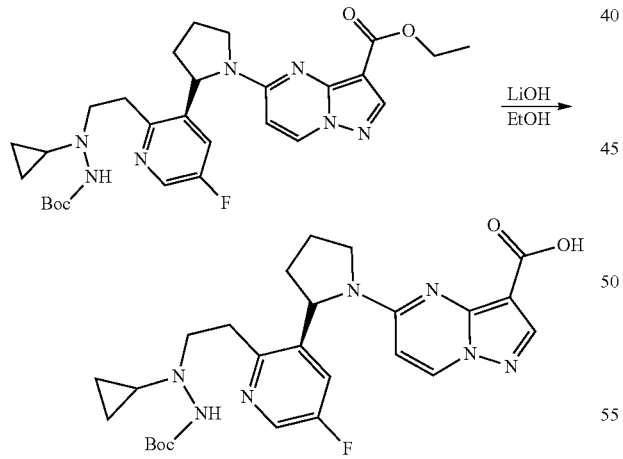

At room temperature, ethyl (S)-5-(2-(2-(2-(2-(tert-butyl-carbonyl)-1-cyclopropylhydrazino)ethyl)-5-fluoropyridin-3-yl)pyrrolidin-1-yl)pyrazolo[1,5-a]pyrimidine-3-carboxylate (85.0 mg, 0.15 mmol) and ethanol (3.0 mL) were added into a 10 mL single-necked flask, and stirred. After complete dissolution, lithium hydroxide monohydrate (38.6 mg, 0.92 mmol, dissolved in 0.5 mL water) was added, the temperature was slowly increased to 70° C., and the reaction was carried out with stirring for 15 hours. The reaction solvent was evaporated to dryness under reduced pressure at 40° C. to obtain a crude product as a yellow solid. MS(ESI) m/z: 526.0[M+H]$^+$.

Step 10: Synthesis of (R,1$^3$E,1$^4$E)-6-cyclopropyl-3$^5$-fluoro-6,7-diazepine-1(5,3)-pyrazolo[1,5-a]pyrimidine-3(3, 2)-pyridine-2(1,2)-pyrrolidine cyclooctane-8-one

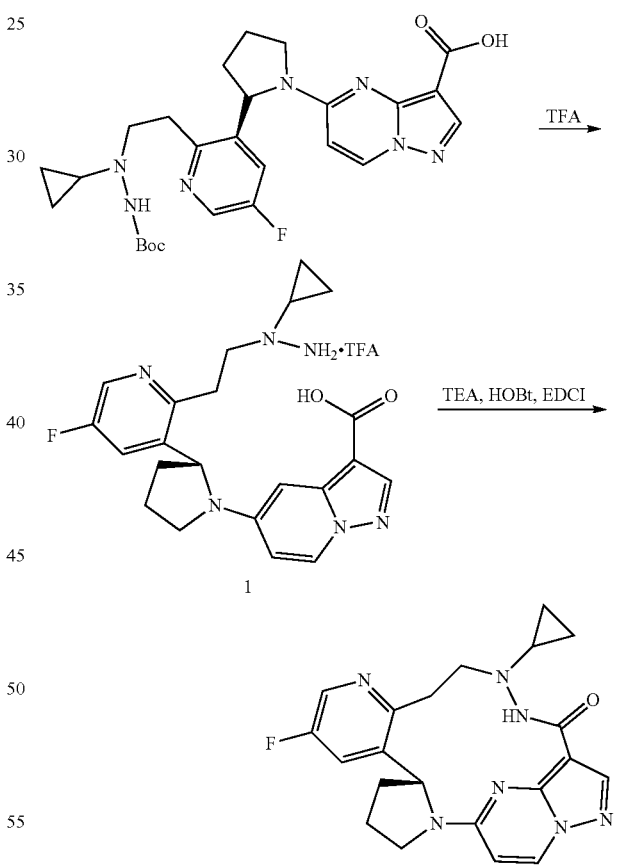

At room temperature, the crude product from the above step was added into a 10 mL single-necked flask, followed by addition of methylene chloride (1.0 mL) and trifluoroacetic acid (1.0 mL), ultrasonically dispersed, and reacted with stirring for 2 hours. The reaction solvent was evaporated to dryness under reduced pressure at 40° C. to obtain a yellow oil, which was further suctioned by an oil pump at room temperature for 4 hours to obtain a pale yellow crude product 1. MS(ESI) m/z: 426.0[M+H]$^+$.

At room temperature, the above crude product 1 was placed into a 10 mL single-necked flask, followed by addition of HOBt (103.7 mg, 0.77 mmol), EDCI (310.7 mg, 0.77 mmol) and DMF (4.0 mL), and ultrasonically dispersed. TEA (310.7 mg, 3.07 mmol) was added. Under the protection of nitrogen, the reaction was carried out overnight at room temperature. The reaction solution was evaporated to dryness under reduced pressure and the product was purified by reverse column chromatography (0.1% formic acid in water/acetonitrile, 95%~0) to obtain a white solid of 11.0 mg. MS (ESI) m/z: 408.0[M+H]$^+$. $^1$H NMR (300 MHz, Chloroform-d) δ 9.73 (br, 1H), 8.33 (d, J=7.7 Hz, 1H), 8.31 (d, J=2.5 Hz, 1H), 8.29 (s, 1H), 7.08 (dd, J=9.4, 2.8 Hz, 1H), 6.33 (d, J=7.7 Hz, 1H), 5.58 (t, J=7.4 Hz, 1H), 4.01-3.65 (m, 6H), 2.94 (dd, J=16.4, 8.6 Hz, 1H), 2.62 (dt, J=13.3, 6.7 Hz, 1H), 2.43 (dt, J=12.2, 6.0 Hz, 1H), 2.24 (dt, J=13.9, 7.5 Hz, 1H), 1.96 (dt, J=13.7, 6.7 Hz, 1H), 1.17 (dd, J=10.3, 5.6 Hz, 1H), 0.87 (dd, J=10.3, 4.0 Hz, 1H), 0.51 (d, J=6.3 Hz, 2H).

Example 2

(1$^3$E,1$^4$E,2$^2$R)-6-cyclopropylamino-3$^5$-fluoro-5-methyl-6,7-diazepine-1(5,3)-pyrazolo[1,5-a]pyrimidine-3(3,2)-azabenzene-2(1,2)-pyrrolidine cyclooctane-8-one

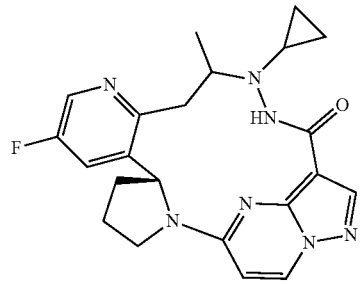 [SMILES: CC1Cc2ncc(F)cc2[C@H]2CCCN2c2ccn3ncc(c3n2)C(=O)NN1C1CC1]

The preparation method of (1$^3$E,1$^4$E,2$^2$R)-6-cyclopropylamino-3$^5$-fluoro-5-methyl-6,7-diazepine-1(5,3)-pyrazolo[1,5-a]pyrimidine-3(3,2)-azabenzene-2(1,2)-pyrrolidine cyclooctane-8-one was similar to that of Example 1.

$^1$H NMR (300 MHz, Chloroform-d) δ 8.33 (d, J=9.0 Hz, 1H), 8.31 (d, J=6.0 Hz 1H), 8.24 (s, 1H), 7.21 (dd, J=9.0, 3.0 Hz, 0.5H), 7.11 (dd, J J=9.0, 3.0 Hz, 0.5H), 6.33 (d, J=7.6 Hz, 1H), 5.55 (t, J=6.0 Hz, 0.5H), 5.48 (t, J=6.0 Hz, 0.5H), 4.17 (m, 1H), 3.97 (m, 1H), 3.78 (m, 1H), 3.64 (m, 1H), 3.41 (m, 1H), 2.57 (ddq, J=19.1, 9.9, 8.6 Hz, 1H), 2.40 (dd, J=13.1, 6.7 Hz, 1H), 2.23 (m, 1H), 2.01 (m, 1H), 1.88 (m, 6.3 Hz, 1H), 1.49 (d, J=6.9 Hz, 1.5H), 1.16 (m, 1.5H), 1.00 (m, 1H), 0.88 (m, 1H), 0.70 (m, 1H), 0.43 (m, 1H). MS (ESI) m/z: 422.2[M+H]$^+$.

Example 3

(1$^3$E,1$^4$E,2$^2$R,5R)-6-cyclopropyl-3$^5$-fluoro-5-methyl-6,7-diazepine-1(5,3)-pyrazolo[1,5-a]pyrimidine-3(3,2)-pyridine-2(1,2)-pyrrolidine cyclooctane-8-one & (1$^3$E,1$^4$E,2$^2$R,5S)-6-cyclopropyl-3$^5$-fluoro-5-methyl-6,7-diazepine-1(5,3)-pyrazolo[1,5-a]pyrimidine-3(3,2)-pyridine-2(1,2)-pyrrolidine cyclooctane-8-one

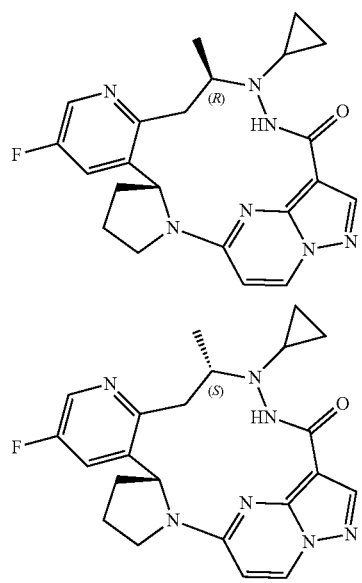

Step 1: Synthesis of (1$^3$E,1$^4$E,2$^2$R)-6-cyclopropylamino-3$^5$-fluoro-5-methyl-6,7-diazepine-1 (5,3)-pyrazolo[1,5-a]pyrimidine-3(3,2)-azabenzene-2(1,2)-pyrrolidine cyclooctane-8-one following the method of Example 2

Step 2: Preparation of (1$^3$E,1$^4$E,2$^2$R,5R)-6-cyclopropyl-3$^5$-fluoro-5-methyl-6,7-diazepine-1(5,3)-pyrazolo[1,5-a]pyrimidine-3(3,2)-pyridine-2(1,2)-pyrrolidine cyclooctane-8-one & (1$^3$E,1$^4$E,2$^2$R,5S)-6-cyclopropyl-3$^5$-fluor-5-methyl-6,7-diazepine-1(5,3)-pyrazolo[1,5-a]pyrimidine-3(3,2)-pyridine-2(1,2)-pyrrolidine cyclooctane-8-one

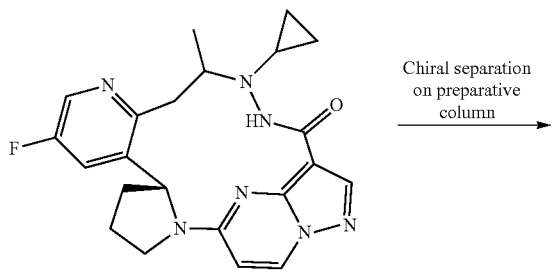

Chiral separation on preparative column

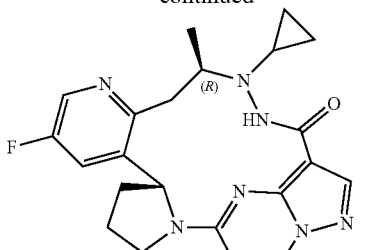

Example 3a (or 3b)

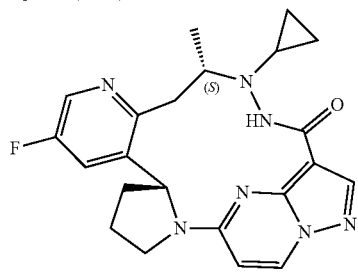

Example 3b (or 3a)

(1³E,1⁴E,2²R)-6-cyclopropylamino-3⁵-fluoro-5-methyl-6,7-diazepine-1(5,3)-pyrazolo[1,5-a]pyrimidine-3(3,2)-azabenzene-2(1,2)-pyrrolidine cyclooctane-8-one (200 mg, 0.47 mmol) was subjected to chiral separation on a preparative column to obtain Example 3a: (1³E,1⁴E,2²R,5R or S)-6-cyclopropyl-3⁵-fluoro-5-methyl-6,7-diazepine-1(5,3)-pyrazolo[1,54]pyrimidine-3(3,2)-pyridine-2(1,2)-pyrrolidine cyclooctane-8-one (28.3 mg, yield 28.3%) and Example 3b: (1³E,1⁴E,2²R,5R or S)-6-cyclopropyl-3⁵-fluoro-5-methyl-6,7-diazepine-1(5,3)-pyrazolo(1,5-a]pyrimidine-3(3,2)-pyridine-2(1,2)-pyrrolidine cyclooctane-8-one (35.6 mg, yield 35.6%).

Separation and Preparation Method:
Instrument: waters SFC200
Chromatographic column: ChiralPak OD, 250×30 mm I.D., 5 μm
Mobile phase: A: $CO_2$; B: MEOH (0.1% $NH_3H_2O$)
Wavelength: 254 nm
Column temperature: 38° C.
Flow rate: 60 g/min
Single injection volume: 5 mL
Single injection concentration: 10 mg/mL
Injection times: 4
Solvent: MeOH
Back pressure: 100 bar
Gradient condition: B 40%
Cycle time: 8 min
Collection condition: concentration under reduced pressure at 40° C.
Separation and Detection Method:
Instrument: waters UPCC
Chromatographic column: ChiralPak OD, 2.1×150 mm I.D., 3 μm
Mobile phase: A: $CO_2$; B: MEOH (0.1% DEA)
Wavelength: 254 nm
Column temperature: 40° C.
Flow rate: 1 mL/min
Injection volume: 2 μL
Injection concentration: 2 mg/mL
Solvent: MeOH
Back pressure: 1500 psi
Gradient condition: B 5%-40%
Runtime: 10 min
Retention time: 4.471 min, 4.788 min Example 3a: (1³E,1⁴E,2²R,5R or S)-6-cyclopropyl-3³-fluoro-5-methyl-6,7-diazepine-1(5,3)-pyrazolo(1,5-a]pyrimidine-3(3,2)-pyridine-2(1,2)-pyrrolidine cyclooctane-8-one, retention time 4.471 min. MS (ESI) m/z: 422.2 [M+H]⁺. ¹H NMR (400 MHz, CDCl3) δ 8.63 (br, 1H), 8.31 (dd, J=23.1, 15.6 Hz, 3H), 7.16-7.07 (m, 1H), 6.33 (d, J=0.6 Hz, 1H), 5.49 (t, J=17.1 Hz, 1H), 4.16 (t, J=8.0 Hz, 1H), 4.01-3.92 (m, 1H), 3.81 (m, 1H), 3.46 (dd, J=33.0, 21.6 Hz, 2H), 3.18 (m, 1H), 2.60 (m, 1H), 2.39 (m, 1H), 2.24 (m, 1H), 1.89 (d, J=11.6 Hz, 1H), 1.29-1.21 (d, J=7.6 Hz, 3H), 1.07-0.93 (m, 2H), 0.74-0.66 (m, 1H), 0.51-0.42 (m, 1H).

Example 3b: (1³E,1⁴E,2²R,5R or S)-6-cyclopropyl-3⁵-fluoro-5-methyl-6,7-diazepine-1(5,3)-pyrazolo(1,5-a]pyrimidine-3(3,2)-pyridine-2(1,2)-pyrrolidine cyclooctane-8-one, retention time 4.788 min. MS(ESI) m/z: 422.2 [M+H]⁺. ¹H NMR (400 MHz, $CDCl_3$) δ 9.11 (br, 1H), 8.42-8.22 (m, 3H), 7.20 (d, J=9.3 Hz, 1H), 6.39-6.25 (d, J=7.6 Hz, 1H), 5.56 (t, J=12 Hz, 1H), 4.18 (t, J=8.0 Hz, 1H), 3.98 (s, 1H), 3.86 (d, J=24.8 Hz, 2H), 2.80 (d, J=16.3 Hz, 1H), 2.53 (m, 1H), 2.42 (m, 1H), 2.30 (m, 1H), 2.22 (m, 1H), 1.88 (d, J=11.6 Hz, 1H), 1.57-1.42 (d, J=7.6 Hz, 3H), 1.02 (m, 1H), 0.93-0.85 (m, 1H), 0.44 (m, 2H).

Example 4

Synthesis of (R,1³E,1⁴E)-3⁵-fluoro-6-methyl-6,7-diazepine-1(5,3)-pyrazolo[1,5-a]pyrimidine-3(3,2)-azabenzene-2(1,2)-pyrrolidine cyclooctane-8-one

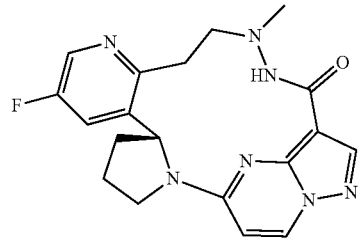 [SMILES: CN1CCc2ncc(F)cc2[C@H]2CCCN2c2ccn3ncc(c3n2)C(=O)N1]

Step 1: Synthesis of ethyl (S)-5-(2-(5-fluoro-2-(2-(methylamino)ethyl)pyridin-3-yl)pyrrolidin-1-yl) pyrazolo[1,5-a]pyrimidine-3-carboxylate

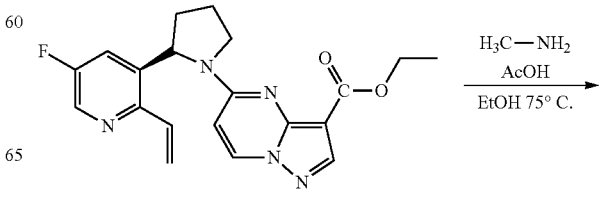

-continued

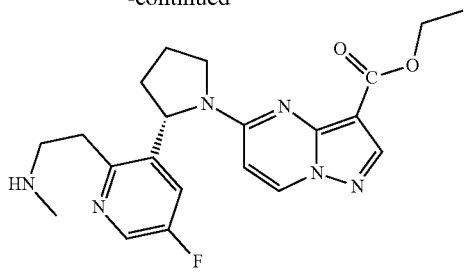

At room temperature, ethyl (S,E)-5-(2-(5-fluoro-2-(prop-1-en-1-yl)pyridin-3-yl)pyrrolidin-1-yl)pyrazolo[1,5-a]pyrimidine-3-carboxylate (1.00 g, 2.62 mmol), 30% methylamine in ethanol (30 mL), and glacial acetic acid (10 mL) were added into a 100 mL single-necked flask, evacuated, replaced with nitrogen, slowly warmed to 75° C., and reacted under reflux for 19 hours. The reaction was stopped. The reaction solution was cooled to room temperature, and EA was added. The reaction solution was washed with a saturated aqueous solution of sodium carbonate. The aqueous phase was back extracted with EA. The organic phases were combined, dried over anhydrous sodium sulfate, and evaporated to dryness under reduced pressure. Column chromatography (DCM/EtOH system) was performed to obtain a yellow solid of 544.3 g, with a yield of 45.74%. MS (ESI) m/z:413.3[M+H]$^+$.

Step 2: Synthesis of ethyl (S)-5-(2-(2-(2-(2-(tert-butylcarbonyl)-1-methylhydrazino)ethyl)-5-fluoropyridin-3-yl)pyrrolidin-1-yl)pyrazolo[1,5-a]pyrimidine-3-carboxylate At room temperature, ethyl (S)-5-(2-(5-fluoro-2-(2-(methylamino)ethyl)pyridin-3-yl)pyrrolidin-1-yl)pyrazolo[1,5-a]pyrimidine-3-carboxylate (439.0 mg, 1.04 mmol), tetrahydrofuran (9.00 mL) and N-methylmorpholine (158.0 mg, 1.56 mmol) were added into a 50 mL single-necked flask. The temperature was reduced to 0° C., and N-Boc-O p-toluenesulfonyl-hydroxylamine (898.3 mg, 3.12 mmol) was added in portions. After the addition was completed and the temperature was returned to room temperature, the reaction was carried out for 19 hours. The reaction was stopped, and EA was added. The reaction solution was washed with a saturated aqueous solution of sodium carbonate. The aqueous phase was extracted with EA. The organic phases were combined, dried over anhydrous Na$_2$SO$_4$, and evaporated to dryness under reduced pressure. Column chromatography (PE/EA system) was performed to obtain a product of 68.2 mg. MS (ESI) m/z: 528.3 [M+H]$^+$.

Step 3: Synthesis of (S)-5-(2-(2-(2-(2-(tert-butylcarbonyl)-1-methylhydrazino)ethyl)-5-fluoropyridin-3-yl)pyrrolidin-1-yl)pyrazolo[1,5-a]pyrimidine-3-carboxylic acid

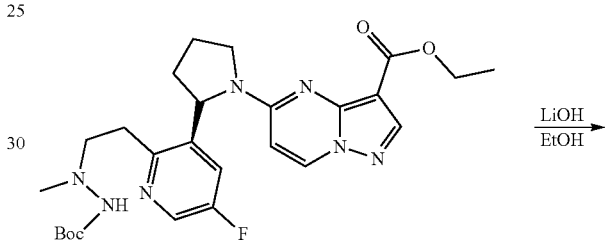

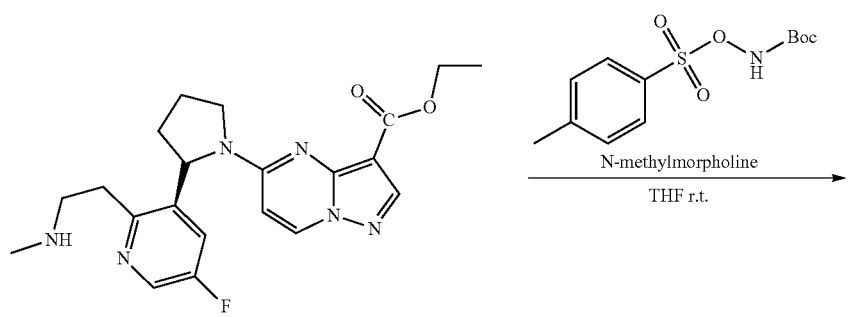

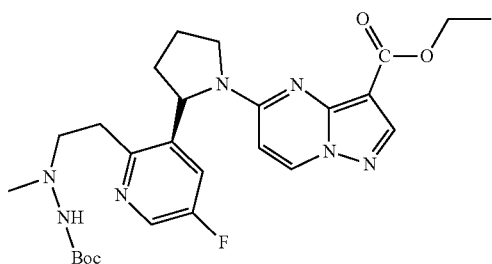

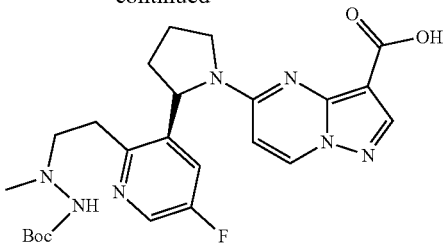

At room temperature, ethyl (S)-5-(2-(2-(2-(2-(tert-butyl-carbonyl)-1-methylhydrazino)ethyl)-5-fluoropyridin-3-yl)pyrrolidin-1-yl)pyrazolo[1,5-a]pyrimidine-3-carboxylate (62.8 mg, 0.13 mmol) and ethanol (2.00 mL) were added into a 25 mL single-necked flask. After complete dissolution, lithium hydroxide monohydrate (32.5 mg, 0.77 mmol) in water (0.5 mL) was added, the temperature was slowly increased to 70° C., and the reaction was carried out with stirring for 6 hours, at which the reaction was complete. The reaction solution was cooled to room temperature, and evaporated to dryness under reduced pressure to obtain a crude product 1 as a yellow solid. MS (ESI) m/z: 500.1[M+H]+.

Step 4: Synthesis of (R,1³E,1⁴E)-3⁵-fluoro-6-methyl-6,7-diazepine-1(5,3)-pyrazolo[1,5-a]pyrimidine-3(3,2)-azabenzene-2(1,2)-pyrrolidine cyclooctane-8-one

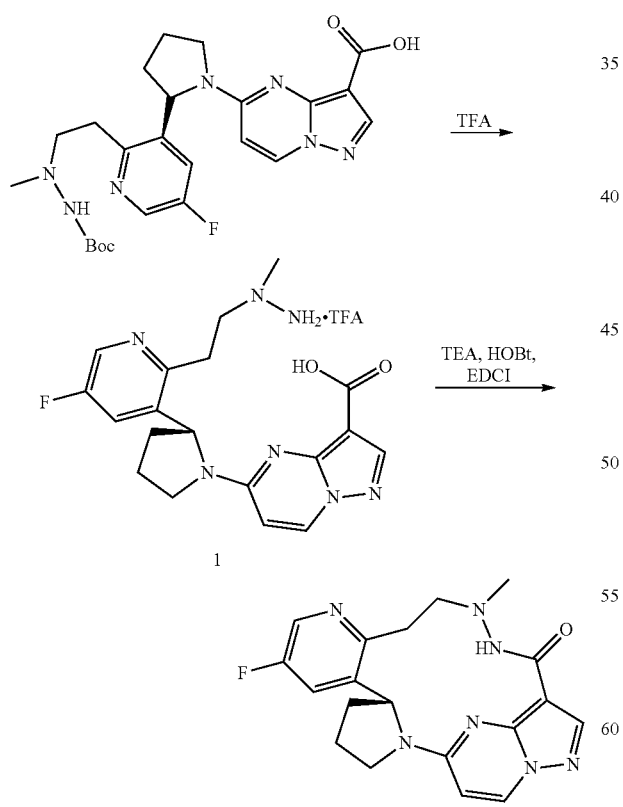

At room temperature, the above crude product 1 was added into a 25 mL single-necked flask, followed by addition of methylene chloride (2.00 mL) and trifluoroacetic acid (2.00 mL), ultrasonically dissolved, and stirred for 2 hours at room temperature, at which the reaction was complete. The reaction was stopped. The reaction system was evaporated to dryness under reduced pressure to obtain a pale yellow crude product 2. MS (ESI) m/z: 400.5[M+H]+.

At room temperature, the above crude product 2 was placed into a 25 single-necked flask, followed by addition of HOBt (87.3 mg, 0.64 mmol), EDCI (123.9 mg, 0.64 mmol), DMF (3.00 mL), and TEA (261.6 mg, 2.58 mmol), evacuated, replaced with nitrogen, and reacted at room temperature overnight, at which the reaction was complete. The reaction system was evaporated to dryness under reduced pressure, and subjected to column chromatography (0.1% formic acid in water/acetonitrile system) to obtain a product of 16.5 mg. MS (ESI) m/z: 382.4[M+H]+. ¹H NMR (300 MHz, Chloroform-d) δ 8.35 (d, J=9.4, 1H), 8.34 (d, 2.8, 1H), 8.31 (s, 1H), 7.10 (dd, J=9.4, 2.8 Hz, 1H), 6.34 (d, J=7.6 Hz, 1H), 5.54 (t, J=7.5 Hz, 1H), 4.12 (dd, J=15.0, 6.2 Hz, 1H), 3.99 (dd, J=7.9, 7.2 Hz, 1H), 3.86 (dd, J=8.7, 7.8 Hz, 1H), 3.72-3.69 (m, 1H), 3.67-3.65 (m, 1H), 2.87-2.79 (m, 1H), 2.77 (s, 3H), 2.66-2.56 (m, 1H), 2.47-2.41 (m, 1H), 2.30-2.23 (m, 1H), 1.97-1.90 (m, 1H).

Example 5

(R,1³E,1⁴E)-6-ethyl-3³-fluoro-6,7-diazepine-1(5,3)-pyrazolo[1,5-a]pyrimidine-3(3,2)-azabenzene-2(1,2)-pyrrolidine cyclooctane-8-one

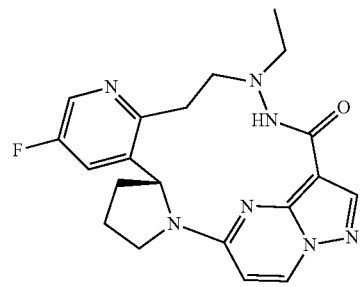 [SMILES: CCN1CCc2ncc(F)cc2[C@H]2CCCN2c2ccn3ncc(c3n2)C(=O)N1]

Step 1: Synthesis of ethyl (S)-5-(2-(2-(2-(ethyl-amino)ethyl)-5-fluoropyridin-3-yl)pyrrolidin-1-yl)pyrazolo[1,5-a]pyrimidine-3-carboxylate

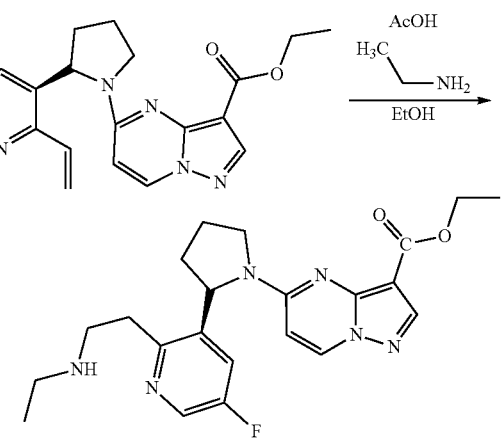

At room temperature, ethyl (S)-5-(2-(5-fluoro-2-vinylpyridin-3-yl)pyrrolidin-1-yl)pyrazolo[1,5-a]pyrimidine-3-carboxylate (1.52 g, 3.98 mmol), 30% ethylamine in ethanol (40.80 mL), and glacial acetic acid (13.60 mL) were added into a 100 mL single-necked flask, evacuated, replaced with nitrogen, slowly warmed to 75° C., and reacted under reflux. After stirring for 23.5 hours, the reaction was stopped. The reaction solution was cooled to room temperature, and EA was added. The reaction solution was washed with a saturated aqueous solution of sodium carbonate. The aqueous phase was back extracted with EA. The organic phases were combined, dried over anhydrous sodium sulfate, and evaporated to dryness under reduced pressure. Column chromatography (DC M/EtOH system) was performed to obtain a yellow solid of 610 mg, with a yield of 33.66%. MS (ESI) m/z: 427.5[M+H]$^+$.

Step 2: Synthesis of ethyl (S)-5-(2-(2-(2-(2-(tert-butylcarbonyl)-1-ethylhydrazino)ethyl)-5-fluoropyridin-3-yl)pyrrolidin-1-yl)pyrazolo[1,5-a]pyrimidine-3-carboxylate

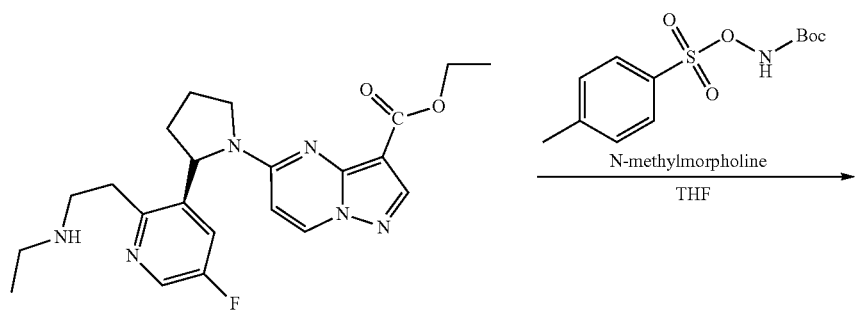

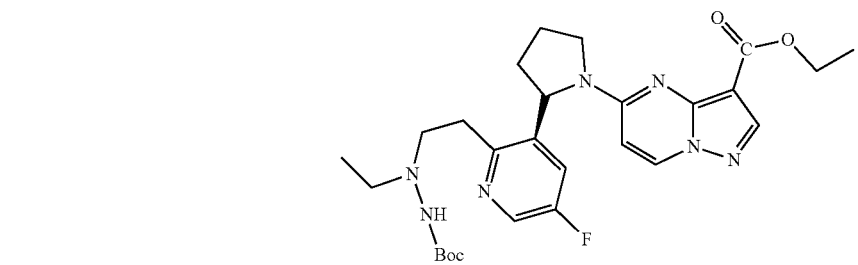

At room temperature, ethyl (S)-5-(2-(2-(2-(ethylamino)ethyl)-5-fluropyridin-3-yl)pyrrolidin-1-yl)pyrazolo[1,5-a]pyrimidine-3-carboxylate (753.7 mg, 1.77 mmol), tetrahydrofuran (15 mL) and N-methylmorpholine (178.8 mg, 1.77 mmol) were added into a 50 mL single-necked flask. The temperature was reduced to 0° C., and N-Boc-O p-toluenesulfonyl-hydroxylamine (2.54 g, 8.84 mmol) was added in portions. After the addition was completed and the temperature was returned to room temperature, the reaction was carried out for 17 hours. The reaction was stopped, and EA was added. The reaction solution was washed with a saturated aqueous solution of sodium carbonate. The aqueous phase was extracted with EA. The organic phases were combined, dried over an hydrous Na$_2$SO$_4$, and evaporated to dryness under reduced pressure. Column chromatography (PE/EA system) was performed to obtain a product of 101.6 mg. MS (ESI) m/z: 542.6[M+H]$^+$.

Step 3: Synthesis of (S)-5-(2-(2-(2-(2-(tert-butylcarbonyl)-1-ethylhydrazino)ethyl)-5-fluoropyridin-3-yl)pyrrolidin-1-yl)pyrazolo[1,5-a]pyrimidine-3-carboxylic acid

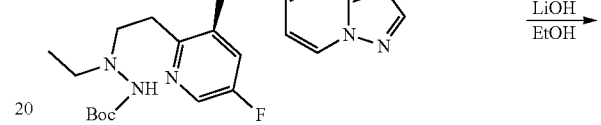

-continued

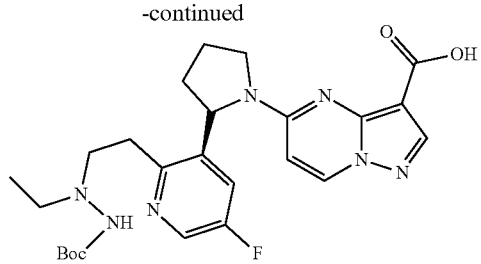

At room temperature, ethyl (S)-5-(2-(2-(2-(2-(tert-butylcarbonyl)-1-ethylhydrazino)ethyl)-5-fluoropyridin-3-yl) pyrrolidin-1-yl)pyrazolo[1,5-a]pyrimidine-3-carboxylate (101.6 mg, 0.19 mmol) and ethanol (4.00 mL) were added into a 25 mL single-necked flask. After complete dissolution, lithium hydroxide monohydrate (47.2 mg, 1.13 mmol) in water (0.8 mL) was added, and the temperature was slowly increased to 70° C. After stirring for 5 hours, the reaction was complete. The reaction system was cooled to room temperature, and evaporated to dryness under reduced pressure to obtain a crude product 1 as a yellow solid. MS (ESI) m/z: 514.5[M+H]+.

Step 4: Synthesis of (R,1³E,1⁴E)-3⁵-fluoro-6-ethyl-6,7-diazepine-1(5,3)-pyrazolo[1,5-a]pyrimidine-3(3,2)-azabenzene-2(1,2)-pyrrolidine cyclooctane-8-one

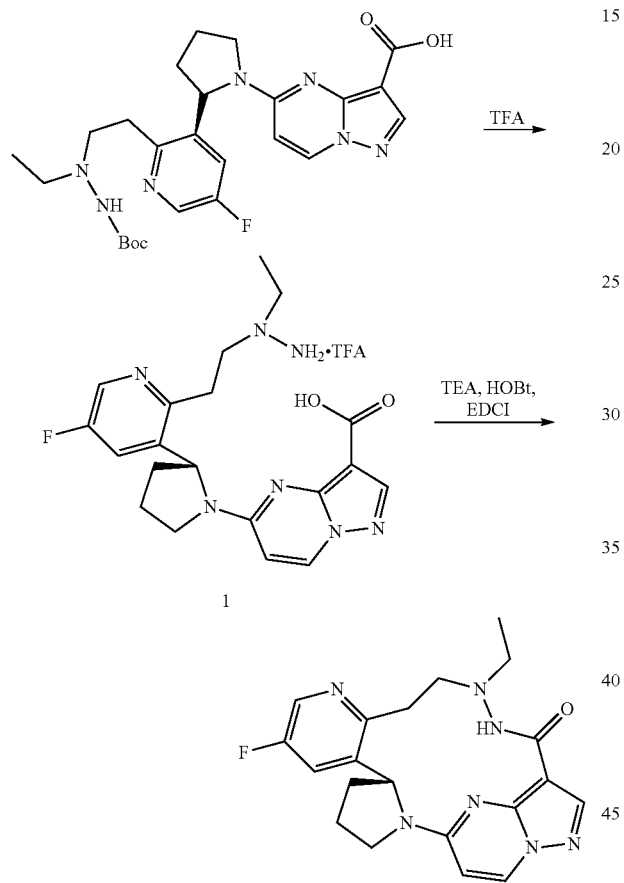

At room temperature, the above crude product 1 was added into a 25 mL single-necked flask, followed by addition of methylene chloride (3.00 mL) and trifluoroacetic acid (3.00 mL), ultrasonically dissolved, and stirred for 1.5 hours at room temperature, at which the reaction was complete. The reaction was stopped. The reaction system was evaporated to dryness under reduced pressure to obtain a pale yellow crude product 2. MS (ESI) m/z: 414.4[M+H]+.

At room temperature, the above crude product 2 was placed into a 25 mL single-necked flask, followed by addition of HOBt (126.7 mg, 0.94 mmol), EDCI (180.0 mg, 0.94 mmol), DMF (6.00 mL), and TEA (380.0 mg, 3.75 mmol), evacuated, replaced with nitrogen, and reacted at room temperature overnight, at which the reaction was complete. The reaction system was evaporated to dryness under reduced pressure, and subjected to column chromatography (0.1% formic acid in water/acetonitrile system) to obtain a product of 14.4 mg. MS (ESI) m/z: 396.4 [M+H]. HPLC: 97.87%. ¹H NMR (300 MHz, Chloroform-d) δ 9.42 (br, 1H), 8.41-8.31 (m, 3H), 7.10 (dd, J=8.4, 2.8 Hz, 1H), 6.36 (d, J=7.9 Hz, 1H), 5.57 (t, J=7.5 Hz, 1H), 4.04-3.95 (m, 2H), 3.92-3.83 (m, 2H), 3.78-3.70 (m, 1H), 3.63 (d, J=17.8 Hz, 1H), 2.98 (q, J=8.4 Hz, 2H), 2.66-2.57 (m, 1H), 2.29-2.18 (m, 2H), 1.26-1.20 (t, J=6.0 Hz, 3H).

Example 6

Synthesis of (R,1³E,1⁴E)-3⁵-fluoro-6-isopropyl-6,7-diazepine-1(5,3)-pyrazolo[1,5-a]pyrimidine-3(3,2)-pyridine-2(1,2)-pyrrolidine cyclooctane-8-one

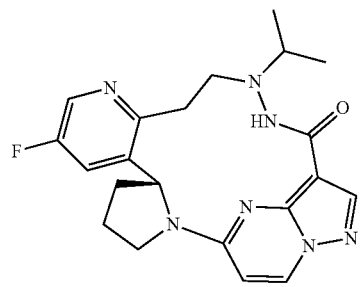 [SMILES: CC(C)N1CCc2ncc(F)cc2[C@H]2CCCN2c2ccn3ncc(c3n2)C(=O)N1]

The preparation method of (R,1³E,1⁴E)-3⁵-fluoro-6-isopropyl-6,7-diazepine-1(5,3)-pyrazolo [1,5-a]pyrimidine-3 (3,2)-pyridine-2(1,2)-pyrrolidine cyclooctane-8-one was similar to that of Example 1.

¹H NMR (400 MHz, CDCl₃) δ 9.41 (br, 1H), 8.33 (d, J=8.0 Hz, 1H), 8.32 (s, 2H), 7.09 (dd, J=9.4, 2.3 Hz, 1H), 6.34 (d, J=7.9 Hz, 1H), 5.56 (t, J=7.3 Hz, 1H), 4.20-4.14 (m, 1H), 4.00 (q, J=8.0 Hz, 1H), 3.88-3.82 (m, 1H), 3.65 (dd, J=15.4, 4.0 Hz, 1H), 3.56 (d, J=16.2 Hz, 1H), 3.09 (p, J=6.2 Hz, 1H), 2.86 (dd, J=15.1, 10.1 Hz, 1H), 2.61 (dd, J=13.4, 6.8 Hz, 1H), 2.44 (dt, J=12.7, 6.3 Hz, 1H), 2.25 (dt, J=13.7, 7.3 Hz, 1H), 1.94 (dd, J=13.5, 6.8 Hz, 1H), 1.29 (d, J=6.3 Hz, 3H), 1.22 (d, J=6.3 Hz, 3H). MS (ESI) m/z: 410.2[M+H]+.

Example 7

(1³E,1⁴E,2²R,5R)-3⁵-fluoro-5,6-dimethyl-6,7-diazepine-1(5,3)-pyrazolo[1,5-a]pyrimidine-3 (3,2)-pyridine-2(1,2)-pyrrolidine cyclooctane-8-one & (1³E, 1⁴E,2²R,5S)-3⁵-fluoro-5,6-dimethyl-6,7-diazepine-1(5,3)-pyrazolo[1,5-a]pyrimidine-3(3,2)-pyridine-2(1,2)-pyrrolidine cyclooctane-8-one

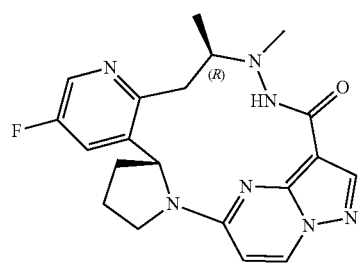

-continued

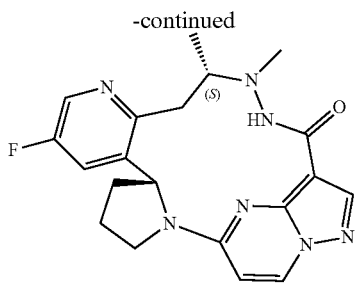

Step 1: Synthesis of (1³E,1⁴E,2²R)-5,6-dimethyl-3⁵-fluoro-6,7-diazepine-1(5,3)-pyrazolo[1,5-a]pyrimidine-3(3,2)-azabenzene-2(1,2)-pyrrolidine cyclooctane-8-one following the method of Example 2

Step 2: Preparation of (1³E,1⁴E,2²R,5R)-3⁵-fluoro-5,6-dimethyl-6,7-diazepine-1(5,3)-pyrazol o[1,5-a]pyrimidine-3(3,2)-pyridine-2(1,2)-pyrrolidine cyclooctane-8-one & (1³E,1⁴E,2²R,5S)-3⁵-fluoro-5, 6-dimethyl-6,7-diazepine-1(5,3)-pyrazolo[1,5-a]pyrimidine-3(3,2)-pyridine-2(1,2)-pyrrolidine cyclooctane-8-one

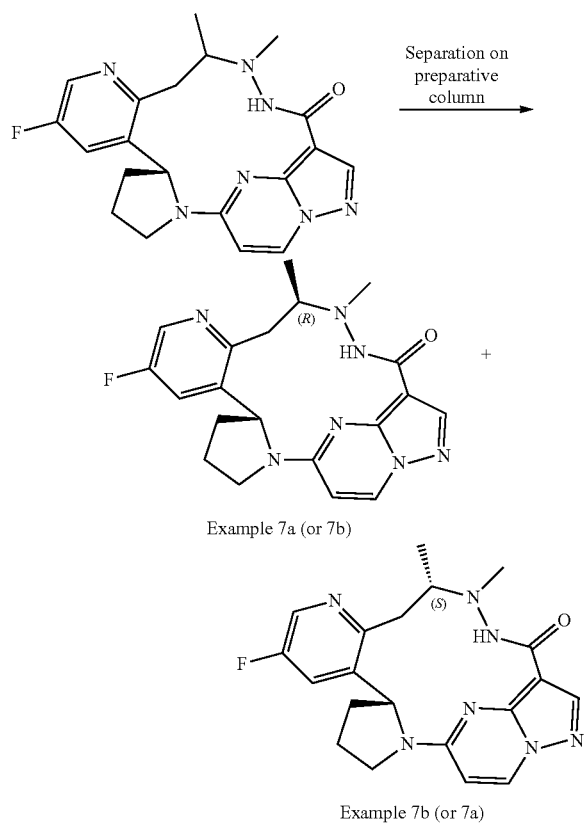

Example 7a (or 7b)

Example 7b (or 7a)

(1³E,1⁴E,2²R)-5,6-dimethyl-3⁵-fluoro-6,7-diazepine-1(5,3)-pyrazolo[1,5-a]pyrimidine-3(3,2)-azabenzene-2(1,2)-pyrrolidine cyclooctane-8-one (260 mg, 0.65 mmol) was subjected to separation on a preparative column to obtain Example 7a: (1³E,1⁴E,2²R,5R or S)-3⁵-fluoro-5,6-dimethyl-6,7-diazepine-1(5,3)-pyrazolo[1,5-a]pyrimidine-3(3,2)-pyridine-2(1,2)-pyrrolidine cyclooctane-8-one (23 mg, yield 17.7%) and Example 7b: (1³E,1⁴E,2²R,5R or S)-3⁵-fluoro-5,6-dimethyl-6,7-diazepine-1(5,3)-pyrazolo[1,5-a]pyrimidine-3(3,2)-pyridine-2(1,2)-pyrrolidine cyclooctane-8-one (56 mg, yield 43.1%).

Separation and Preparation Method:

Instrument: Qingbohua LC2000 High Performance Liquid Chromatograph

Chromatographic column: YMC Triart C18 250*20 mm 10 um

Mobile phase: A: acetonitrile; mobile phase B: 0.1% trifluoroacetic acid in water Wavelength: 230 nm Column temperature: 35° C.

Flow rate: 10 ml/min

Solvent: acetonitrile

Preparation conditions: 0 min A25B75 25 min A25B75 30 min A26B74 35 min A28B72

Collection condition: concentration under reduced pressure at 40° C.

Separation and Detection Method:

Instrument: Agilent 1260 Infinity II

Chromatographic column: Xtimate C18 4.6*50 mm 3 um

Mobile phase: A: acetonitrile; B: 0.1% trifluoroacetic acid in water

Wavelength: 230 nm

Column temperature: 35° C.

Flow rate: 1 mL/min

Injection volume: 20 μL

Retention time: 2.371 min, 2.844 min

Solvent: acetonitrile

Detection condition: B 10%-76%

Example 7a: (1³E,1⁴E,2²R,5R or S)-3⁵-fluoro-5,6-dimethyl-6,7-diazepine-1(5,3)-pyrazolo[1,5-a]pyrimidine-3(3,2)-pyridine-2(1,2)-pyrrolidine cyclooctane-8-one, retention time 2.371 min. MS (ESI) m/z: 396.2 [M+H]⁺. ¹H NMR (400 MHz, DMSO-d6) δ 9.55 (br, 1H), 8.82 (d, J=7.7 Hz, 1H), 8.37 (m, 1H), 8.11 (s, 1H), 7.54 (d, J=9.8 Hz, 1H), 6.72 (d, J=7.8 Hz, 1H), 5.40 (t, J=6.8 Hz, 1H), 4.20 (m, 1H), 4.08 (q, J=7.5 Hz, 1H), 3.84 (m, 1H), 3.53-3.42 (m, 1H), 3.23 (dd, J=14.5, 10.6 Hz, 1H), 3.04 (s, 3H), 2.62 (dt, J=12.6, 6.5 Hz, 1H), 2.24 (dt, J=11.7, 5.9 Hz, 1H), 2.08 (d q, J=12.9, 7.4 Hz, 1H), 1.83-1.72 (m, 1H), 1.31 (d, J=6.9 Hz, 3H).

Example 7b: (1³E,1⁴E,2²R,5R or S)-3⁵-fluoro-5,6-dimethyl-6,7-diazepine-1(5,3)-pyrazolo[1,5-a]pyrimidine-3(3,2)-pyridine-2(1,2)-pyrrolidine cyclooctane-8-one, retention time 2.844 min. MS (EST) m/z: 396.2 [M+H]⁺. ¹H NMR (400 MHz, DMSO-d6) δ 9.64 (br, 1H), 8.80 (d, J=7.7 Hz, 1H), 8.42 (d, J=2.6 Hz, 1H), 8.13 (s, 1H), 7.59 (d, J=12.6 Hz, 1H), 6.69 (d, J=7.8 Hz, 1H), 5.61 (t, J=7.1 Hz, 1H), 4.14 (d, J=7.2 Hz, 1H), 3.96 (s, 1H), 3.91 (d, J=5.0 Hz, 1H), 3.88-3.75 (m, 2H), 2.65 (s, 3H), 2.59 (s, 1H), 2.31 (dq, J=11.7, 5.7, 5.1 Hz, 1H), 2.14-1.99 (m, 1H), 1.80 (dq, J=13.5, 7.1 Hz, 1H), 1.46 (d, J=6.9 Hz, 3H).

Example 8

(1³E,1'E,2²R,5R)-3⁵-fluoro-6-ethyl-5-methyl-6,7-diazepine-1(5,3)-pyrazolo[1,5-a]pyrimidin e-3(3,2)-pyridine-2 (1,2)-pyrrolidine cyclooctan-8-one & (1³E,1⁴E,2²R,5S)-3⁵-fluoro-6-ethyl-5-methyl-6,7-diazepine-1(5,3)-pyrazolo[1,5-a]pyrimidine-3(3,2)-pyridine-2(1,2)-pyrrolidine cyclooctan-8-one Step 1: Synthesis of (1³E,1⁴E,2²R)-3⁵-fluoro-6-ethyl-5-methyl-6,7-diazepine-1(5,3)-pyrazolo [1,5-a]pyrimidine-3(3,2)-pyridine-2(1,2)-pyrrolidine cyclooctan-8-one following the method of Example 2

Step 2: Preparation of (1³E,1⁴E,2²R,5R)-3⁵-fluoro-6-ethyl-5-methyl-6,7-diazepine-1(5,3)-pyrazolo[1,5-a]pyrimidine-3(3,2)-pyridine-2(1,2)-pyrrolidine cyclooctan-8-one & (1³E,1⁴E,2²R,5S)-3⁵-fluoro-6-ethyl-5-methyl-6,7-diazepine-1(5,3)-pyrazolo[1,5-a]pyrimidine-3(3,2)-pyridine-2(1,2)-pyrrolidine cyclooctan-8-one Example 8a (or 8b)

Example 8b (or 8a)

(1³E,1⁴E,2²R)-3⁵-fluoro-6-ethyl-5-methyl-6,7-diazepine-1(5,3)-pyrazolo[1,5-a]pyrimidine-3 (3,2)-pyridine-2(1,2)-pyrrolidine cyclooctane-8-one (320 mg, 0.78 mmol) was subjected to separation on a preparative column to obtain Example 8a: (1³E,1⁴E,2²R,5R or S)-3⁵-fluoro-6-ethyl-5-methyl-6,7-diazepine-1(5,3)-pyrazolo[1,5-a]pyrimidine-3 (3,2)-pyridine-2(1,2)-pyrrolidine cyclooctane-8-one (26 mg, yield 16.2%) and Example 8b: (1³E,1⁴E,2²R,5R or S)-3⁵-fluoro-6-ethyl-5-methyl-6,7-diazepine-1(5,3-a]pyrimidine-3(3,2)-pyridine-2(1,2)-pyrrolidine cyclooctane-8-one (53 mg, yield 33.1%).

Separation and Preparation Method:
Instrument: Qingbohua LC2000 High Performance Liquid Chromatograph
Chromatographic column: YMC Triart C18 250*20 mm 10 um
Mobile phase: A: acetonitrile; mobile phase B: 0.05% trifluoroacetic acid in water
Wavelength: 230 nm
Column temperature: 35° C.
Flow rate: 10 ml/min
Solvent: acetonitrile
Preparation conditions: 0 min A33B67 25 min A33B67 30 min A35B65
Collection condition: concentration under reduced pressure at 40° C.
Separation and Detection Method:
Instrument: Agilent 1260 Infinity II
Chromatographic column: Xtimate C18 4.6*50 mm 3 um
Mobile phase: A: acetonitrile; B: 0.1% trifluoroacetic acid in water
Wavelength: 230 nm
Column temperature: 35° C.
Flow rate: 1 mL/min
Injection volume: 20 μL
Retention time: 1.898 min, 2.369 min
Solvent: acetonitrile
Detection condition: B10%-72%
Example 8a: (1³E,1⁴E,2²R,5R or S)-3⁵-fluoro-6-ethyl-5-methyl-6,7-diazepine-1(5,3)-pyrazolo[1,5-a]pyrimidine-3(3,2)-pyridine-2(1,2)-pyrrolidine cyclooctane-8-one, retention time 1.898 min. MS (ESI) m/z: 410.1 [M+H]⁺. ¹NMR (400 MHz, DMSO-d6) δ9.55 (br, 1H), 8.82 (d, J=7.7 Hz, 1H), 8.37 (m, 1H), 8.11 (s, 1H), 7.54 (d, J=9.8 Hz, 1H), 6.72 (d, J=7.8 Hz, 1H), 5.40 (t, J=6.8 Hz, 1H), 4.20 (m, 1H), 4.08 (q, J=7.5 Hz, 1H), 3.84 (m, 1H), 3.53-3.42 (m, 1H), 3.23 (dd, J=14.5, 10.6 Hz, 1H), 3.04 (s, 3H), 2.62 (dt, J=12.6, 6.5 Hz, 1H), 2.24 (dt, J=11.7, 5.9 Hz, 1H), 2.08 (d q, J=12.9, 7.4 Hz, 1H), 1.83-1.72 (m, 1H), 1.04 (m, 6H).
Example 8b: (1³E,1⁴E,2²R,5R or S)-3⁵-fluoro-6-ethyl-5-methyl-6,7-diazepine-1(5,3)-pyrazolo[1,5-a]pyrimidine-3 (3,2)-pyridine-2(1,2)-pyrrolidine cyclooctane-8-one, retention time 2.369 min. MS (ESI) m/z: 410.1 [M+H]+. 1H NMR (400 MHz, DMSO-d6) δ 9.02 (br, 1H), 8.76 (d, J=7.7 Hz, 1H), 8.39 (d, J=2.5 Hz, 1H), 8.06 (s, 1H), 7.56 (dd, J=10.1, 2.4 Hz, 1H), 6.66 (d, J=7.8 Hz, 1H), 5.59 (s, 1H), 4.22-3.94 (m, 1H), 3.90-3.73 (m, 2H), 3.68-3.59 (m, 1H), 2.90-2.74 (m, 1H), 2.67 (p, J=8.3, 7.5 Hz, 1H), 2.53 (m, 1H), 2.48-2.40 (m, 1H), 2.30 (dq, J=12.0, 6.6 Hz, 1H), 2.07 (dt, J=13.2, 7.2 Hz, 1H), 1.77 (td, J=12.9, 6.3 Hz, 1H), 1.44 (d, J=6.9 Hz, 3H), 0.98 (t, J=6.9 Hz, 3H).

Example 9

(R,1³E,1⁴E)-3⁵-fluoro-6-isobutyl-6,7-diazepine-1(5,3)-pyrazolo[1,5-a]pyrimidine-3(3,2)-pyridine-2(1,2)-pyrrolidine cyclooctane-8-one

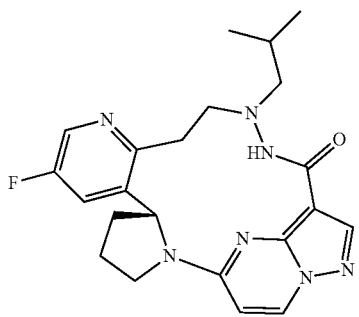 [SMILES: CC(C)CN1CCc2ncc(F)cc2[C@H]2CCCN2c2ccn3ncc(c3n2)C(=O)N1]

The preparation method of (R,1³E,1⁴E)-3⁵-fluoro-6-isobutyl-6,7-diazepine-1(5,3)-pyrazolo[1, 5-a]pyrimidine-3(3,2)-pyridine-2(1,2)-pyrrolidine cyclooctane-8-one was similar to that of Example 1.

1H NMR (400 MHz, CDCl3) δ 9.29 (br, 1H), 8.30 (dd, J=9.5, 7.2 Hz, 3H), 7.07 (dd, J=9.4, 2.8 Hz, 1H), 6.32 (d, J=7.7 Hz, 1H), 5.57-5.53 (t, J=7.3 Hz, 1H), 3.99-3.91 (m, 2H), 3.87-3.80 (m, 2H), 3.63 (dt, J=16.0, 3.5 Hz, 1H), 2.86-2.76 (m, 2H), 2.65 (dt, J=13.3, 6.8 Hz, 1H), 2.54 (dd, J=11.8, 8.4 Hz, 1H), 2.43 (dt, J=12.6, 6.2 Hz, 1H), 2.25 (dt, J=13.5, 7.5 Hz, 1H), 1.97-1.88 (dt, J=14.2, 7.2 Hz, 1H), 1.82 (dt, J=13.6, 6.6 Hz, 1H), 1.12 (d, J=6.5 Hz, 3H), 0.96 (d, J=6.7 Hz, 3H). MS (ESI) m/z: 424.2[M+H]+.

Example 10

Synthesis of (R,1³E,1⁴E)-6-cyclopropyl-3⁵-fluoro-6,7-diaza-1(5,3)-pyrazoline[1,5-a]pyrimidine-3(3,2)-pyridine-2(1,2)-pyrrolidine cyclotridecane-8-one

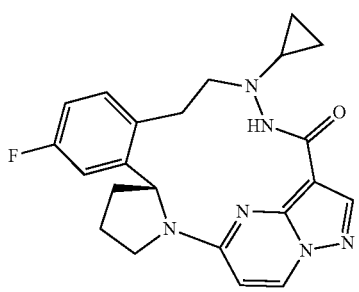 [SMILES: O=C1NN(C2CC2)CCc2ccc(F)cc2[C@H]2CCCN2c2ccn3ncc1c3n2]

Step 1: 2-(2-bromo-4-fluorophenyl)ethanol

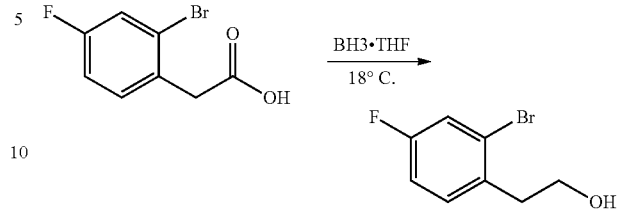

2-(2-bromo-4-fluorophenyl)acetic acid (46.63 g, 200.00 mmol) was dissolved in 500 mL of THF, and borane in tetrahydrofuran (1.0 M, 300 mL) was added at 0° C. The reaction was carried out for 16 h at 18° C. and stopped. The reaction solution was quenched with 1 N diluted hydrochloric acid, and extracted with EA. The organic phase was washed with saturated brine, dried over anhydrous Na2SO4, filtered and concentrated to obtain a yellow oil of 42.57 g, with a yield of 97%.

Step 2: 2-bromo-4-fluoro-1-(2-(4-methoxybenzyloxy)ethyl)benzene

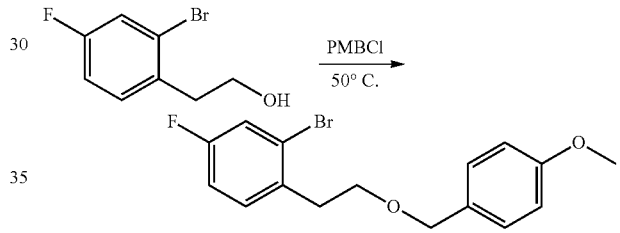

At room temperature, NaH (4.10 g, 102.00 mmol) and 200 mL of THF were added into a four-necked flask. 2-(2-bromo-4-fluorophenyl)ethanol (14.90 g, 102.00 mmol) was added at 0° C. The reaction was carried out at 0° C. for 0.5 h and tetrabutylammonium iodide (36.28 g, 96.00 mmol) and p-methoxybenzyl chloride (12.78 g, 82.00 mmol) were added. The reaction was carried out for 4 h at 50° C. and stopped. The reaction solution was quenched with 1 N diluted hydrochloric acid, and extracted with EA. The organic phase was washed with saturated brine, dried over anhydrous Na2SO4, filtered and concentrated to obtain a colorless oil of 15.37 g, with a yield of 67%.

Step 3: 5-fluoro-2-(2-(4-methoxybenzyloxy)ethyl)benzaldehyde

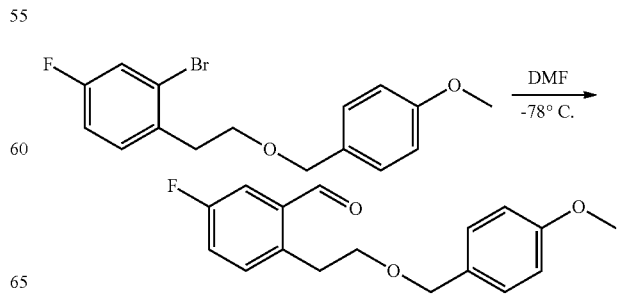

At room temperature, 2-bromo-4-fluoro-1-(2-(4-methoxybenzyloxy)ethyl)benzene (15.37 g, 45.50 mmol) was dissolved in THF (500 mL). Under the protection of N2, sec-butyllithium (70 mL) was added at −78° C. and stirred at −78° C. for 1 h. Then, DMF (18.17 g, 230.00 mmol) was added. The reaction was carried out for 0.5 h while controlling the temperature at −78° C., and stopped. The reaction solution was quenched with a saturated ammonium chloride solution. It was extracted with EA. The organic phase was washed with water, dried over anhydrous MgSO₄, filtered, concentrated, and purified by column chromatography (EA/PE system), to obtain a yellow oil of 8.01 g, with a yield of 62%.

Step 4: (R,E)-N-(5-fluoro-2-(4-methoxybenzyloxy) ethyl)benzylidene)-2-tert-butyl-2-sulfonimide

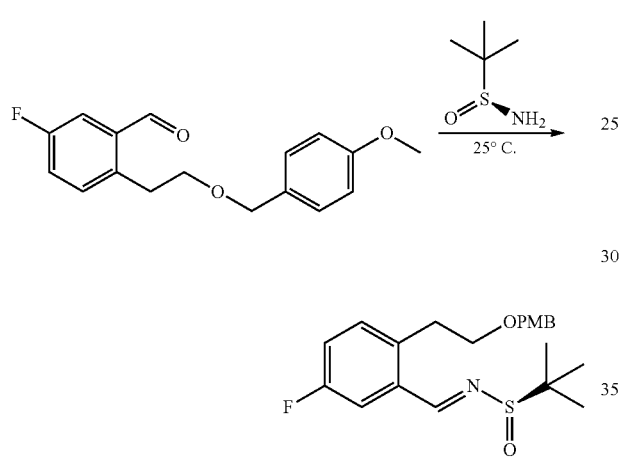

At room temperature, 5-fluoro-2-(2-(4-methoxybenzyloxy)ethyl)benzaldehyde (8.00 g, 28.00 mmol), R-tert-butylsulfinamide (3.56 g, 30.00 mmol), Cs₂CO₃ (6.33 g, 19.00 mmol), and 100 mL of DCM were sequentially added into a single-necked flask. The reaction was carried out under the protection of N₂ at 25° C. for 16 h, and stopped. The reaction solution was poured into water, and separated. The organic phase was washed with saturated brine, dried over anhydrous MgSO₄, filtered, and concentrated to obtain a yellow oil of 10.88 g, with a yield of 100%.

Step 5: N—((R)-3-((1,3-dioxan-2-yl)-1-(5-fluoro-2-(2-(4-methoxybenzyloxy)ethyl)phenyl)propyl)-2-tert-butyl-2-sulfonimide

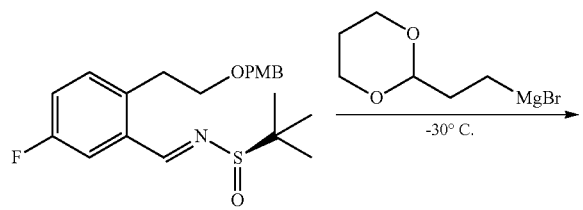

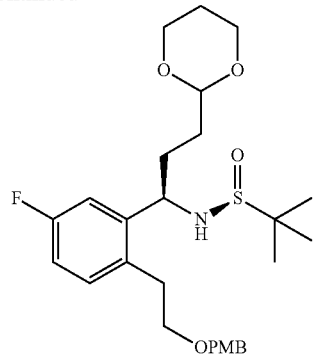

At room temperature, Mg powder (0.87 g, 36.00 mmol), 1-bromo-3,3-dimethoxypropane (7.10 g, 36.00 mmol) and THF (100 mL) were sequentially added into a four-necked flask, evacuated, and replaced with N₂. Under the protection of N₂, the reaction was initiated by heating, and the reaction was carried out at 25° C. for 2 h. (R,E)-N-(5-fluoro-2-(4-methoxybenzyloxy)ethyl)methylene)-2-tert-butyl-2-sulfonimide (10.88 g, 28.00 mmol) in THF (40 mL) was added dropwise in an ice bath. After the addition, the temperature was increased to 25° C., and the reaction was carried out for 2 h and stopped. A saturated NH₄Cl solution was added in an ice bath to quench the reaction. Layers were separated. The aqueous phase was extracted with EA. The organic phases were combined, dried over anhydrous MgSO₄, filtered and concentrated to obtain a white solid of 14.20 g, with a yield of 100%.

Step 6: (R)-2-(2-(3,4-dihydro-2H-pyrrol-2-yl)-4-fluoro)phenethyl alcohol

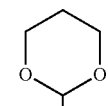

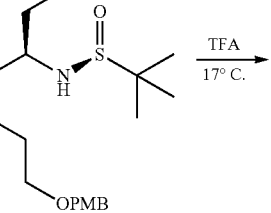

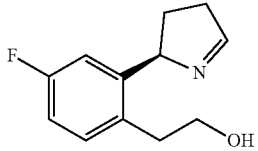

At room temperature, (S)—N—((R)-3-((1,3-dioxan-2-yl)-1-(5-fluoro-2-(2-(4-methoxybenzyloxy)ethyl)phenyl) propyl)-2-tert-butyl-2-sulfonimide (14.20 g, 28.00 mmol) and H₂O (25 mL) were sequentially added into a single-necked flask. TFA (100 mL) was added dropwise in an ice bath. After the addition, the reaction was carried out with stirring for 20 min. The temperature was raised to 25° C., and the reaction was carried out for 22 h and stopped. The reaction solution was directly used in the next step.

Step 7: (R)-2-(4-fluoro-2-(pyrrolidin-2-yl)phenethyl alcohol

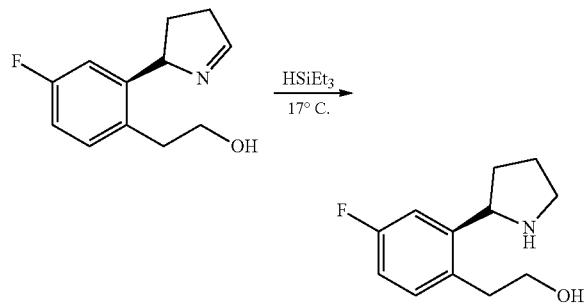

At room temperature, (R)-2-(2-(3,4-dihydro-2H-pyrrol-2-yl)-4-fluoro)phenethyl alcohol (the reaction solution from the previous step) was added into a single-necked flask. Triethylsilane (9.77 g, 84.00 mmol) was added in portions in an ice salt bath. After the addition, the temperature was raised to 17° C. and the reaction was carried out for 1 h. A 2N HCl aqueous solution was added to quench the reaction and adjust the system to a pH of 2-3. The system was washed with EA, adjusted to a pH of 9-10 with a 1N NaOH aqueous solution, and extracted with DCM. The organic phase was dried over anhydrous $Na_2SO_4$, filtered, and concentrated to obtain a pale yellow oil of 3.80 g, with a total yield over two steps of 65%.

Step 8: ethyl (R)-5-(2-(5-fluoro-2-(2-hydroxyethyl)phenyl)pyrrol-1-yl)pyrazoline[1,5-a]pyrimidine-3-carboxylate

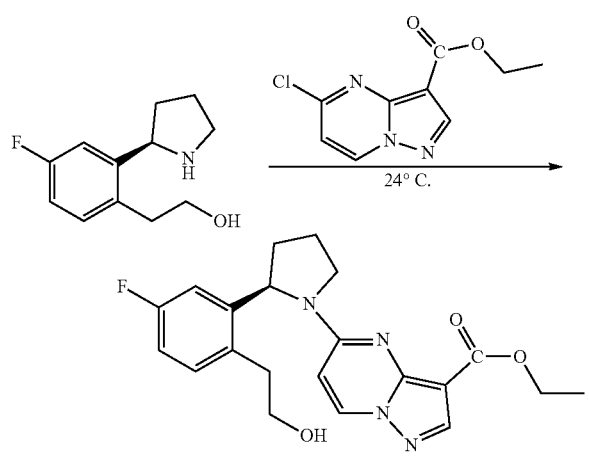

At room temperature, (R)-2-(4-fluoro-2-(pyrrolidin-2-yl)phenethyl alcohol (3.80 g, 18.00 mmol), ethyl 5-chloropyrazolo[1,5-A]pyrimidine-3-carboxylate (4.10 g, 18.00 mmol), TEA (3.64 g, 36.00 mmol), and EtOH (50 mL) were sequentially added into a single-necked flask, evacuated, and replaced with $N_2$. Under the protection of $N_2$, the reaction was carried out for 16 h at 24° C. and stopped. Ethanol was removed by rotary evaporation, and DCM and water were added. The reaction solution was stirred and separated. The aqueous phase was removed. The organic phase was washed with saturated brine and a saturated aqueous $NaHCO_3$ solution, dried over anhydrous $Na_2SO_4$, filtered, concentrated, and purified by column chromatography (EA/PE system) to obtain a yellow foamy solid of 3.56 g, with a yield of 50%.

Step 9: ethyl(R)-5-(2-(5-fluoro-2-(2-methylsulfonyl)ethyl)phenyl)pyrrol-1-yl)pyrazoline[1,5-a]pyrimidine-3-carboxylate

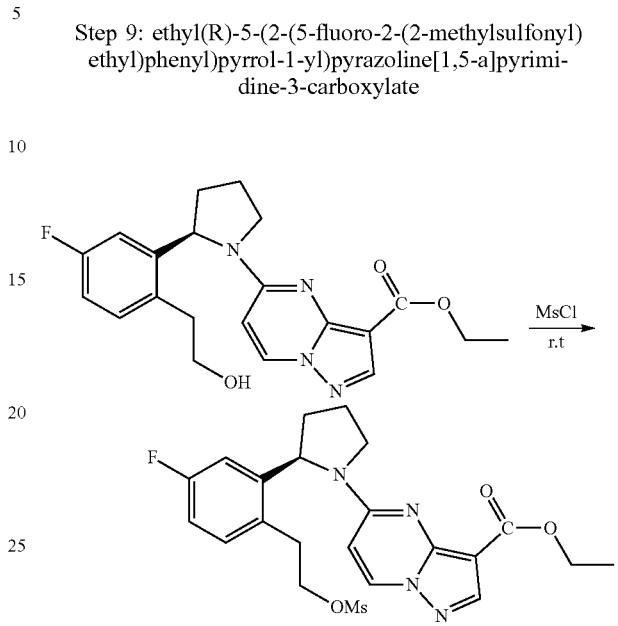

At room temperature, ethyl (R)-5-(2-(5-fluoro-2-(2-hydroxyethyl)phenyl)pyrrol-1-yl)pyrazoline[1,5-a]pyrimidine-3-carboxylate (2.00 g, 5.02 mmol), TEA (1.52 g, 15.06 mmol) and 50 mL of DCM were sequentially added into a single-necked flask, and methanesulfonyl chloride (1.16 g, 10.04 mmol) was added in an ice bath. The temperature was naturally increased to 26° C., and the reaction was carried out for 2 h and stopped. The reaction solution was poured into water, stirred, extracted, and separated. The organic phase was dried over anhydrous $Na_2SO_4$, filtered, and concentrated to obtain a yellow liquid. The crude product was directly used in the next step, with a yield of 100%.

Step 10: ethyl (R)-5-(2-(2-(2(cyclopropylamino)ethyl)-5-fluorophenyl)pyrrol-1-yl)pyrazoline[1,5-a]pyrimidine-3-carboxylate

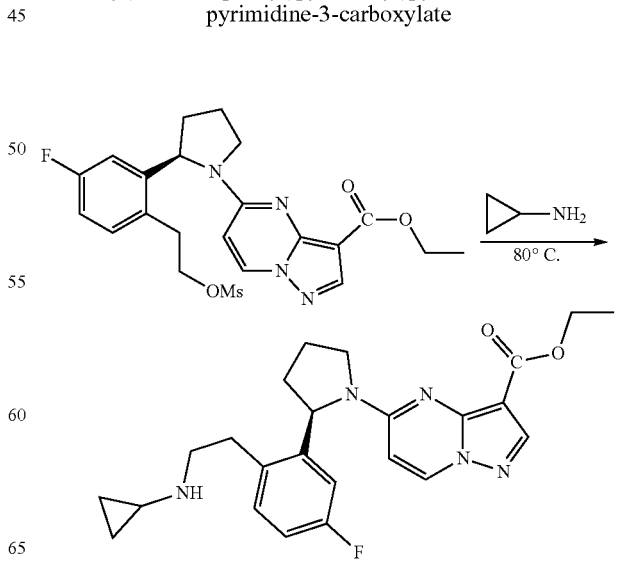

At room temperature, ethyl (R)-5-(2-(5-fluoro-2-(2-methylsulfonyl)ethyl)phenyl)pyrrol-1-yl) pyrazoline[1,5-a]pyrimidine-3-carboxylate (the crude product from the previous step, 5.02 mmol), cyclopropylamine (0.86 g, 15.06 mmol) and DMF (30 mL) were sequentially added into a single-necked flask. Under the protection of N₂, the reaction was carried out at 80° C. for 3 h and stopped. The reaction solution was poured into water, and EA was added for extraction. The EA phase was washed with lN diluted hydrochloric acid. The aqueous phase was added with sodium carbonate to adjust to PH-12. EA was added for extraction. The organic phase was washed with saturated brine, dried over anhydrous Na₂SO₄, filtered, and concentrated to obtain a pale yellow liquid of 1.69 g, with a yield of 77%.

Step 11: Synthesis of ethyl (R)-5-(2-(2-(2-(2-(tert-butylcarbonyl)-1-cyclopropylhydrazino)ethyl)-5-fluorophenyl)pyrrolidin-1-yl)pyrazolo[1,5-a]pyrimidine-3-carboxylate Step 12: Synthesis of (R)-5-(2-(2-(2-(2-(tert-butylcarbonyl)-1-cyclopropylhydrazino)ethyl)-5-fluorophenyl)pyrrolidin-1-yl)pyrazolo[1,5-a]pyrimidine-3-carboxylic acid

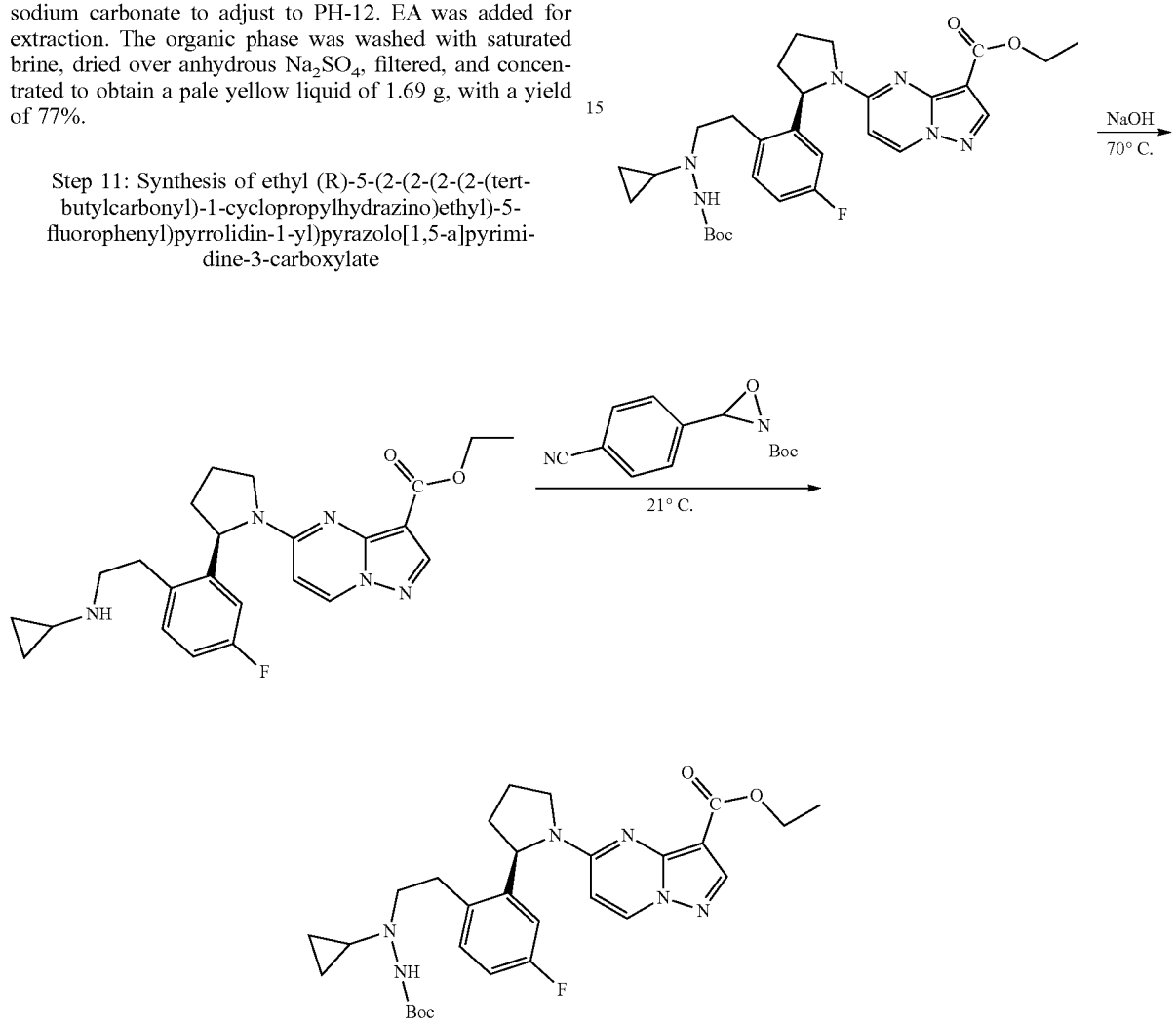

At room temperature, ethyl (R)-5-(2-(2-(2(cyclopropylamino)ethyl)-5-fluorophenyl)pyrrol-1-yl)pyrazoline[1,5-a]pyrimidine-3-carboxylate (1.67 g, 3.82 mmol), N-tert-butoxycarbonyl-3-(4-cyanophenyl) oxaziridine (1.25 g, 4.97 mmol) and DMF (25 mL) were sequentially added into a single-necked flask. The reaction was carried out for 16 h at 21° C. and stopped. EA was added, and the reaction solution was washed with water. The aqueous phase was back extracted with EA. The organic phases were combined, dried over anhydrous Na₂SO₄, filtered, and concentrated. Column chromatography (PE/EA system) was performed to obtain a yellow oily solid of 1.02 g, with a yield of 68%.

-continued

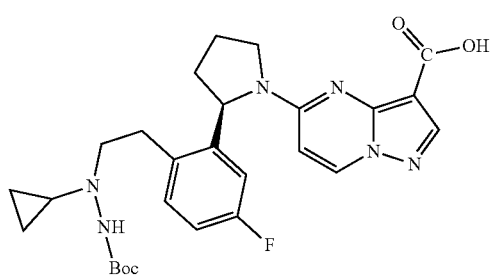

At room temperature, ethyl (R)-5-(2-(2-(2-(2-(tert-butyl-carbonyl)-1-cyclopropylhydrazino)ethyl)-5-fluorophenyl)pyrrolidin-1-yl)pyrazolo[1,5-a]pyrimidine-3-carboxylate (0.70 g, 1.34 mmol) and ethanol (10 mL) were sequentially added into a single-necked flask and stirred to be completely dissolved. Then, a solution of sodium hydroxide (0.32 g, 8.04 mmol) in water (5 mL) was add ed. The temperature was raised to 70° C., and the reaction was carried out for 16 h and stopped. It was cooled to room temperature, concentrated to remove most of ethanol, and adjusted to a pH of 3-4 by adding DCM, $H_2O$ and 1 N HCl, and layers were separated after stirring. The aqueous phase was again extracted with DCM. The organic phases were combined, dried over anhydrous $Mg_2SO_4$, filtered and concentrated to obtain a white solid of 0.63 g, with a yield of 95%.

Step 13: (R)-5-(2-(2-(2-(1-cyclopropylhydrazino)ethyl)-5-fluorophenyl)pyrrolidin-1-yl)pyrazolo[1,5-a]pyrimidine-3-carboxylic acid

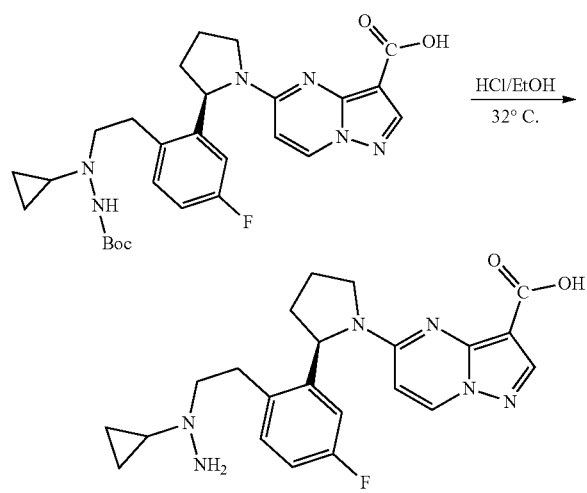

At room temperature, (R)-5-(2-(2-(2-(2-(tert-butylcarbonyl)-1-cyclopropylhydrazino)ethyl)-5-fluorophenyl)pyrrolidin-1-yl)pyrazolo[1,5-a]pyrimidine-3-carboxylic acid (0.63 g, 1.20 mmol) and a solution of HCl in ethanol (10 mL) were added to a single-necked flask, and stirred to be completely dissolved. The reaction was carried out at 32° C. for 1 h and stopped. The reaction system was concentrated to dryness under reduced pressure to obtain a pale yellow solid of 0.60 g, with a yield of 100%.

Step 14: (R,$^{13}$E,$^{14}$E)-6-cyclopropyl-3$^5$-fluoro-6,7-diaza-1(5,3)-pyrazoline[1,5-a]pyrimidine-3 (3,2)-phenyl-2(1,2)-pyrrolidine cyclotridecane-8-one At room temperature, TBTU (0.68 g, 2.12 mmol), DMAP (0.034 g, 0.30 mmol), DMF (6 mL), and DCM (30 mL) were sequentially added to a four-necked flask, evacuated, and replaced with $N_2$. Under the protection of $N_2$, DIEA (1.09 g, 8.46 mmol) was added. (R)-5-(2-(2-(2-(1-cyclopropylhydrazino)ethyl)-5-fluorophenyl)pyrrolidin-1-yl)pyrazolo[1,5-a]pyrimidine-3-carboxylic acid (0.60 g, 1.41 mmol) was dissolved with a mixed solution of DMF (6 mL) and DCM (6 mL) to form a clear solution. The clear solution was divided into five equal parts. One aliquot of the above-mentioned solution was added at 32° C. every 1 h. After the completion of the addition, the reaction was carried out at 32° C. for 1 h and stopped. The reaction system was concentrated to dryness under reduced pressure, and purified by column chromatography (DCM/$CH_3OH$ system) to obtain an off-white solid of 0.22 g, with a yield of 42%. $^1H$ NMR (400 MHz, Chloroform-d) 9.85 (br, 1H), 8.30 (d, J=9.3 Hz, 2l1), 7.20 (m, 1H), 6.90 (t, J=8.0 Hz, 1H), 6.78 (d, J=10.2 Hz, 1H), 6.33 (d, J=7.7 Hz, 11H), 5.67 (t, J=6.6 Hz, 1H), 3.99 (dt, J=14.0, 7.9 Hz, 2H), 3.90-3.72 (m, 1H), 3.65-3.50 (m, 2H), 2.94-2.88 (m, 111), 2.67-2.50 (m, 2H), 2.50-2.33 (m, 1H), 2.21 (dt, J=13.3, 7.0 Hz, 1H), 1.93 (dt, J=12.7, 6.5 Hz, 1H), 1.14 (m, 1H), 0.90 (d, J=10.2 Hz, 1H), 0.54 (m, 2H). MS (ESI) m/z: 407 [M+H]$^+$.

Example 11

Inhibitory Activity Test for Trk Kinases

In this experiment, the γ-$^{33}$P-ATP isotope test was used to test the inhibition effect of a compound on kinases TrkA, TrkB and TrkC, and the half maximal inhibitory concentration $IC_{50}$ of the inhibitory activity of the compound on the enzymes was obtained. The Trk inhibitor LOXO-101 reported in the literature was used as a positive control, and LOXO-101 was purchased from Shanghai Sinochemtech Co., Ltd., under lot number: SCT0142170801.

1. Basic Reaction Buffer 20 mM Hepes (pH 7.5), 10 mM $MgCl_2$, 1 mM EGTA, 0.02% Brij35, 0.02 mg/ml BSA, 0.1 mM $Na_3VO_4$, 2 mM DTT, 1% DMSO.

2. Formulation of Compounds

A compound was dissolved in 100% DMSO to a particular concentration, and then the resulting solution was gradient-diluted by an automatic loading device to different concentrations of the test samples (DMSO dissolving solutions).

3. Reaction Procedure 3.1. The reaction substrate was diluted using the base reaction buffer;

3.2. The kinase was added into the substrate solution and mixed gently and uniformly;

3.3. The compounds of different concentrations diluted in 100% DMSO were added into the kinase solution using an automatic loading system, and incubated for 20 min at room temperature;

3.4. $^{33}$P-ATP (10 μM, 10 μCi/μl) was added at room temperature to initiate the kinase reaction, and the reaction was carried out for 2 h.

4. Detection

The reaction solution was subjected to an ion exchange filtration system to remove unreacted ATP and the generated ADP ions during the reaction. Then, the radiometric quantity of $^{33}$P isotope in the substrate was detected.

5. Data Processing

The kinase activity in the system with the addition of the inhibitors of different concentrations was calculated from the radiometric quantity, to obtain the inhibitory effect of the compounds with different concentrations on the kinase activity. Fitting was performed using graphpad prism to obtain $IC_{50}$ values of the compounds for inhibition.

The biochemical activity of the compounds of the present invention was determined by the above experiment, and the measured $IC_{50}$ values are shown in table 1:

TABLE 1

Test results of inhibitory activity for Trk kinases

| Compound | Kinase IC$_{50}$ (nM) | | |
|---|---|---|---|
| | TrkA | TrkB | TrkC |
| Example 1 | 4.23 | 0.57 | 0.25 |
| Example 2 | 3.81 | — | — |
| Example 3a | 2.27 | 1.58 | 0.46 |
| Example 3b | 2.16 | 1.13 | 0.38 |
| Example 4 | 12.6 | — | — |
| Example 5 | 7.92 | — | — |
| Example 6 | 2.09 | 0.83 | 0.29 |
| Example 7a | 3.20 | 4.04 | 0.58 |
| Example 7b | 2.62 | 0.71 | 0.19 |
| Example 8a | 4.01 | 6.19 | 0.76 |
| Example 8b | 1.85 | 1.35 | 0.34 |
| Example 9 | 2.36 | 2.16 | 0.32 |
| LOXO-101 | 5.58 | 1.10 | 0.67 |

Note:
"—" in the table indicates not tested.

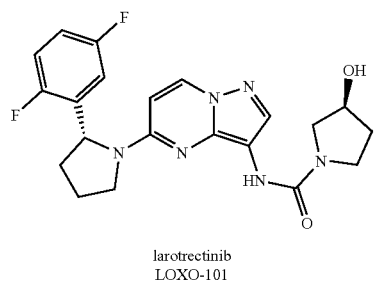 [SMILES: O=C(Nc1cnn2ccc(N3CCC[C@@H]3c3cc(F)ccc3F)nc12)N1CC[C@H](O)C1]

larotrectinib
LOXO-101

Conclusion: The compounds of the present invention have better inhibitory activity for Trk kinases than the positive control.

Example 12

Growth Inhibition Test for Tel-NTRK1-BaF3 and BaF3-LMNA-NTRK1 Cells

In this experiment, the CellTiter-Glo cell proliferation fluorescence assay was used to test the growth inhibitory effect of a compound on tel-NTRK1-BaF3 and BaF3-LMNA-NTRK1 transgenic cells, and the half maximal growth inhibitory concentration GI$_{50}$ of the compound on the cells was obtained. Trk inhibitor LOXO-101 reported in the literature was used as a positive control, and LOXO-101 was purchased from HaoyuanChemexpress Co., Ltd.

1. Experimental Instruments and Consumables
   I) PreceDo target equivalent gene stable cell line library;
   II) CellTiter-Glo cell proliferation fluorescence assay reagent (Promega, USA);
   III) Special 96-well plate for drug screening (Corning, Rochester, N.Y.);
   IV) Compounds for testing.

2. Preparation of Compound Plates

A compound to be tested was dissolved in DMSO to formulate 10 mM of a mother solution. The mother solution was 3× diluted to 10 mM, 3.333 mM, 1.111 mM, 0.370 mM, 0.123 mM, 0.041 mM, 0.014 mM, 0.005 mM, and 0.002 mM. The prepared solutions were each stored in a 0.5 ml sterilized dorft tube (Corning, USA). In addition, an equal volume of DMSO solvent was used as a blank control. With 10 concentration gradients, the plate was stored in vacuum at −20° C.

3. Cell Culture Conditions

The tel-NTRK1-BaF3 and BaF3-LMNA-NTRK1 cell lines were cultured with RPMI 1640 (Corning, N.Y., USA)+ 10% fetal bovine serum (Gibico, Invitrogen, USA). After the cells were thawed, they were cultured for two generations to be tested.

4. Testing and Data Processing

Logarithmic growth phase cells (2000-2500 cells/well) were inoculated in a 12×8 96-well white opaque cell culture plate (Corning 3570, NY, USA) in a volume of 100 μL per well, and a drug was added to the cell plate (0.1 μL/well) at the final concentration of the compound of 10 μM, 3.3 μM, 1.1 μM, 0.37 μM, 0.12 IM, 0.04 μM, 0.014 IM, 0.005 μM, and 0.002 μM (0.4 uL of the drug solution was added to 400 ul of the cell homogenate, and then mixed uniformly, and the resulting mixture was added at 100 ul per well). The plate was incubated at 37° C. in a 5% CO$_2$ incubator for 72 hours, and then 20 μL CellTiter-Glo cell proliferation fluorescence assay reagent was added. The plate was allowed to stand for 10 min, and read in the Envision Plate-Reader.

5. Experimental Verification

A vehicle group (only DMSO added) was used as a negative control in the plates.

6. Results

A corresponding fluorescence value RLU of each well was obtained by reading in the Envision Plate-reader. Raw data RLU$_{Drug}$ for the compounds to be tested were normalized to the RLU$_{Drug}$ for the DMSO control group:

Cell Viability %=(RLU$_{Drug}$/RLU$_{DMSO}$)*100%

Nonlinear regression curve fitting was performed for the cell inhibition value of a single concentration of the compound to be tested by using Graph Pad Prism version 6.0, to obtain the GI$_{50}$ values.

7. Basic Reaction Buffer 20 mM Hepes (pH 7.5), 10 mM MgCl$_2$, 1 mM EGTA, 0.02% mg/ml BSA, 0.1 mM Na3VO4, 2 mM DTT, 1% DMSO.

The biochemical activity of the compounds of the present invention was determined by the above experiment, and the measured GI$_{50}$ values are shown in table 2:

TABLE 2

Test results of inhibitory activity for TRK fusion cell lines

| Compound | Cell GI$_{50}$ (nM) | |
|---|---|---|
| | BaF3-tel-NTRK1 | BaF3-LMNA-NTRK1 |
| Example 1 | 12.0 | 15.1 |
| Example 2 | 18.0 | — |
| LOXO-101 | 24.6 | 35.7 |

Note:
"—" in the table indicates not tested.

Conclusion: The compounds of the present invention have better growth inhibitory activity for TRK fusion cell lines than the positive control.

Example 13

Testing on Metabolic Stability of Compounds in Human Liver Microsomes

The total volume of an incubation system was 250 μL, and 50 mmol/L PBS buffer (pH=7.4) was used to prepare incubation solutions of liver microsomes from various species with a protein concentration of 0.5 mg/mL. Before the start of the incubation, 2.5 μL of a 100 μmol/L compound to be tested was mixed with 197.5 μL of the above incubation solution, pre-incubated in a 37° C. water bath for 5 min, and then added with a 50 μL reducing coenzyme II solution (5 mmol/L) that was likewise pre-incubated for 5 min to start the reaction (in the reaction system, the protein content of liver microsomes from various species was 0.5 g/L, and the final concentration of the compound to be tested was 1 μmol/L), incubated in a 37° C. water bath with shaking, and taken out at 0, 5, 15, 30, and and 60 min. 600 μL of a methanol solution of mixed positive and negative internal standards with internal standards Terfenadine (positive ion internal standard, 25 ng/mL) and Tolbutamide (negative ion internal standard, 50 ng/mL) was immediately added to terminate the reaction. The incubation solution after termination was shaken for 2 min and centrifuged (4° C., 16000 r/min) for 10 min, and the supernatant was taken for LC-MS/MS detection to quantitatively analyze the remaining amount of the parent drug. (DMSO<0.1%).

The concentration of the compound at 0 min incubation was regarded as 100%, and the concentrations at other incubation time points were converted into the remaining percentages. The natural logarithm of the remaining percentage at each time point was linearly regressed against the incubation time, and the slope k was calculated. According to the formula $T_{1/2}=-0.693/k$, the in vitro half-life was calculated. Clearance in liver microsomes (CLint (μL/min/mg protein)=Ln (2)*1000/$T_{1/2}$ (min)/Protein Conc(mg/ml)).

Test data of metabolic stability of the compounds of the present invention in human liver microsomes are listed in detail in table 3:

TABLE 3

Test results of metabolic stability in human liver microsomes
Results of metabolic stability of tested substances in human liver microsomes

| Tested substance No. | Remaining % (60 min) | $T_{1/2}$ (min) | Clint (μL/min/ mg protein) | Negative control Remaining % (60 min) |
|---|---|---|---|---|
| Example 1 | 52.26 | 66.6 | 20.8 | 98.1 |
| Example 4 | 88.39 | 217.0 | 6.40 | 108.0 |
| LOXO-101 | 47.78 | 59.2 | 23.4 | 95.9 |
| LOXO-195 | 6.70 | 15.3 | 90.6 | 102 |

Note:
Trk inhibitor, LOXO-195 was prepared with reference to the method of patent WO2011146336.

Conclusion: Compared with the control compound, the compounds of the present invention have better metabolic stability in human liver microsomes and better druggability than the positive control drug.

The invention claimed is:

1. A compound represented by formula (I), stereoisomer thereof, or pharmaceutically acceptable salt thereof:

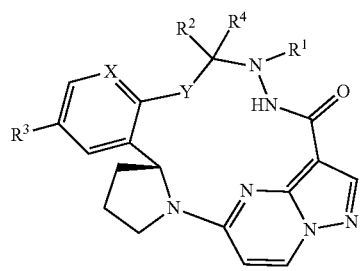

(I)

wherein $R^1$ is selected from H, $C_1$-$C_8$ alkyl, $C_3$-$C_8$ cycloalkyl, $C_2$-$C_8$ alkenyl, $C_2$-$C_8$ alkynyl, —$COR^5$, —$SO_2R^5$, and —$SOR^5$, and optionally further substituted with one or more substituents selected from deuterium, halogen, hydroxyl, cyano, nitro, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxy, and a 4-10 membered heterocyclic group;

$R^2$ and $R^4$ are each independently selected from H, $C_1$-$C_8$ alkyl, $C_3$-$C_8$ cycloalkyl, $C_2$-$C_8$ alkenyl, and $C_2$-$C_8$ alkynyl, and optionally further substituted with one or more substituents selected from deuterium, halogen, hydroxyl, cyano, nitro, —$NR^6R^8$, —$NR^6COR^5$, —$COR^5$, —$SO_2R^5$, —$SOR^5$, $C_1$-$C_8$ alkyl, $C_3$-$C_8$ cycloalkyl, $C_1$-$C_8$ alkoxy, and a 4-10 membered heterocyclic group;

$R^5$ and $R^7$ are each independently selected from H, $C_1$-$C_8$ alkyl, $C_3$-$C_8$ cycloalkyl, and —$NR^8$;

$R^6$ and $R^8$ are each independently selected from H, $C_1$-$C_8$ alkyl, and $C_3$-$C_8$ cycloalkyl;

Y is —$(CH_2)_n$— or —$O(CH_2)_n$—;

n is 0, 1, 2 or 3;

alternatively, any two of $R^1$, $R^2$, and $R^4$ independently form a $C_3$-$C_8$ cycloalkyl group or a 4-10 membered heterocyclic group;

$R^3$ is selected from H, deuterium, halogen, cyano, nitro, $C_1$-$C_8$ alkyl, $C_3$-$C_8$ cycloalkyl, and $C_1$-$C_8$ alkoxy; and X is CH or N.

2. The compound of general formula (I), stereoisomer thereof, or pharmaceutically accepted salt thereof according to claim 1, which is a compound of general formula (II), stereoisomer thereof, or pharmaceutically acceptable salt thereof:

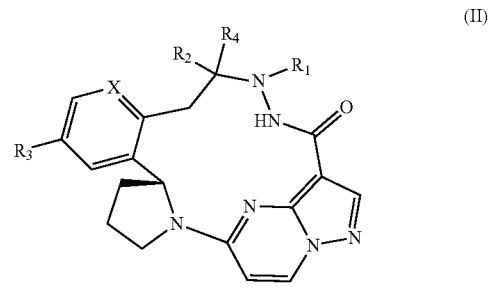

(II)

wherein $R^1$ is selected from H, $C_1$-$C_8$ alkyl, $C_3$-$C_8$ cycloalkyl, $C_2$-$C_8$ alkenyl, $C_2$-$C_8$ alkynyl, —$COR^5$, —$SO_2R^5$, and —$SOR^5$, and optionally further substituted with one or more substituents selected from deuterium, halogen, hydroxyl, cyano, nitro, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxy, and a 4-10 membered heterocyclic group;

$R^2$ and $R^4$ are each independently selected from H, $C_1$-$C_8$ alkyl, $C_3$-$C_8$ cycloalkyl, $C_2$-$C_8$ alkenyl, and $C_2$-$C_8$ alkynyl, and optionally further substituted with one or more substituents selected from deuterium, halogen, hydroxyl, cyano, nitro, —$NR^6R^8$, —$NR^6COR^5$, —$COR^5$, —$SO_2R^5$, —$SOR^5$, $C_1$-$C_8$ alkyl, $C_3$-$C_8$ cycloalkyl, $C_1$-$C_8$ alkoxy, and a 4-10 membered heterocyclic group;

$R^5$ and $R^7$ are each independently selected from H, $C_1$-$C_8$ alkyl, $C_3$-$C_8$ cycloalkyl, and —$NR^8$;

$R^6$ and $R^8$ are each independently selected from H, $C_1$-$C_8$ alkyl, and $C_3$-$C_8$ cycloalkyl;

alternatively, any two of $R^1$, $R^2$, and $R^4$ independently form a $C_3$-$C_8$ cycloalkyl group or a 4-10 membered heterocyclic group;

$R^3$ is selected from H, deuterium, halogen, cyano, nitro, $C_1$-$C_8$ alkyl, $C_3$-$C_8$ cycloalkyl, and $C_1$-$C_8$ alkoxy; and X is CH or N.

3. The compound according to claim 2, wherein:

$R^1$ is selected from H, $C_1$-$C_8$ alkyl, $C_3$-$C_8$ cycloalkyl, $C_2$-$C_8$ alkenyl, and $C_2$-$C_8$ alkynyl, and optionally further substituted with one or more substituents selected from deuterium, halogen, hydroxyl, cyano, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxy, and a 4-10 membered heterocyclic group;

$R^2$ and $R^4$ are each independently selected from H, $C_1$-$C_8$ alkyl, $C_3$-$C_8$ cycloalkyl, $C_2$-$C_8$ alkenyl, and $C_2$-$C_8$ alkynyl, and optionally further substituted with one or more substituents selected from deuterium, halogen, hydroxyl, cyano, —$NR^6R^8$, —$NR^6COR^5$, —$COR^5$, —$SO_2R^5$, —$SOR^5$, $C_1$-$C_8$ alkyl, $C_3$-$C_8$ cycloalkyl, $C_1$-$C_8$ alkoxy, and a 4-10 membered heterocyclic group;

$R^5$ and $R^7$ are each independently selected from H, $C_1$-$C_8$ alkyl, $C_3$-$C_8$ cycloalkyl, and —$NR^8$;

$R^6$ and $R^8$ are each independently selected from H, $C_1$-$C_8$ alkyl, and $C_3$-$C_8$ cycloalkyl;

alternatively, any two of $R^1$, $R^2$, and $R^4$ independently form a $C_3$-$C_8$ cycloalkyl group, and a 4-10 membered heterocyclic group;

$R^3$ is halogen; and

X is CH or N.

4. The compound according to claim 3, wherein:

$R^1$ is selected from H, $C_1$-$C_8$ alkyl, and $C_3$-$C_8$ cycloalkyl, and optionally further substituted with one or more selected from deuterium, halogen, hydroxyl, cyano, —$NR^6R^8$, —$NR^6COR^7$, —$COR^7$, —$SO_2R^7$, —$SOR^7$, $C_1$-$C_8$ alkyl, $C_3$-$C_8$ cycloalkyl, $C_1$-$C_8$ alkoxy, and a 4-10 membered heterocyclic group;

$R^2$ and $R^4$ are each independently selected from H, $C_1$-$C_8$ alkyl, and $C_3$-$C_8$ cycloalkyl, and optionally further substituted with one or more substituents selected from deuterium, halogen, hydroxyl, cyano, —$NR^6R^8$, —$NR^6COR^5$, —$COR^5$, —$SO_2R^5$, —$SOR^5$, $C_1$-$C_8$ alkyl, $C_3$-$C_8$ cycloalkyl, $C_1$-$C_8$ alkoxy, and a 4-10 membered heterocyclic group;

$R^5$ and $R^7$ are each independently selected from H, $C_1$-$C_8$ alkyl, $C_3$-$C_8$ cycloalkyl, or —$NR^8$;

$R^6$ and $R^8$ are each independently selected from H, $C_1$-$C_8$ alkyl, or $C_3$-$C_8$ cycloalkyl;

Alternatively, any two of $R^1$, $R^2$, and $R^4$ independently form a $C_3$-$C_8$ cycloalkyl group or a 4-10 membered heterocyclic group;

$R^3$ is halogen; and

X is CH or N.

5. The compound according to claim 4, wherein:

$R^1$ is selected from H, $C_1$-$C_8$ alkyl, and $C_3$-$C_8$ cycloalkyl, and optionally further substituted with one or more substituents selected from deuterium, halogen, hydroxyl, cyano, —$SO_2R^7$, $C_1$-$C_4$ alkyl, $C_3$-$C_6$ cycloalkyl, and $C_1$-$C_4$ alkoxy;

$R^7$ is selected from H, $C_1$-$C_8$ alkyl, and $C_3$-$C_8$ cycloalkyl;

$R^2$ and $R^4$ are each independently selected from H, $C_1$-$C_8$ alkyl, and $C_3$-$C_8$ cycloalkyl, and optionally further substituted with one or more substituents selected from deuterium, halogen, hydroxyl, cyano, $C_1$-$C_4$ alkyl, $C_3$-$C_6$ cycloalkyl, and $C_1$-$C_4$ alkoxy;

alternatively, any two of $R^1$, $R^2$, and $R^4$ independently form a $C_3$-$C_8$ cycloalkyl group or a 4-10 membered heterocyclic group;

$R^3$ is halogen; and

X is selected from CH or N.

6. The compound according to claim 5, wherein:

$R^1$ is selected from H, $C_1$-$C_8$ alkyl, and $C_3$-$C_8$ cycloalkyl, and optionally further substituted with one or more substituents selected from deuterium, hydroxyl, halogen, —$SO_2R^7$, and $C_1$-$C_4$ alkoxy;

$R^7$ is H or $C_1$-$C_8$ alkyl;

$R^2$ and $R^4$ are each independently selected from H, $C_1$-$C_8$ alkyl, and $C_3$-$C_8$ cycloalkyl;

alternatively, any two of $R^1$, $R^2$, and $R^4$ independently form a 4-10 membered heterocyclic group;

$R^3$ is fluorine or chlorine; and

X is CH or N.

7. The compound according to claim 6, wherein:

$R^1$ is selected from H, methyl, ethyl, n-propyl, isopropyl, n-butyl, isobutyl, tert-butyl, cyclopropyl, cyclobutyl, cyclopentyl, and cyclohexyl, and optionally further substituted with one or more substituents selected from deuterium, hydroxyl, F, Cl, —$SO_2CH_3$, and methoxy;

$R^2$ and $R^4$ are each independently selected from H, methyl, ethyl, n-propyl, isopropyl, n-butyl, isobutyl, tert-butyl, cyclopropyl, cyclobutyl, cyclopentyl, and cyclohexyl;

alternatively, any two of $R^1$, $R^2$, and $R^4$ independently form a morpholinyl;

$R^3$ is fluorine or chlorine; and

X is CH or N.

8. A compound, stereoisomer thereof or pharmaceutically acceptable salt thereof, wherein the compound has a structural formula selected from the following:

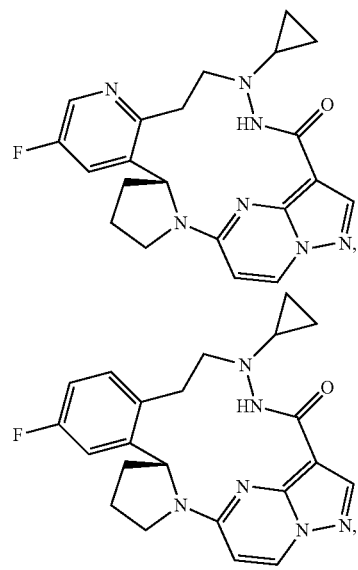

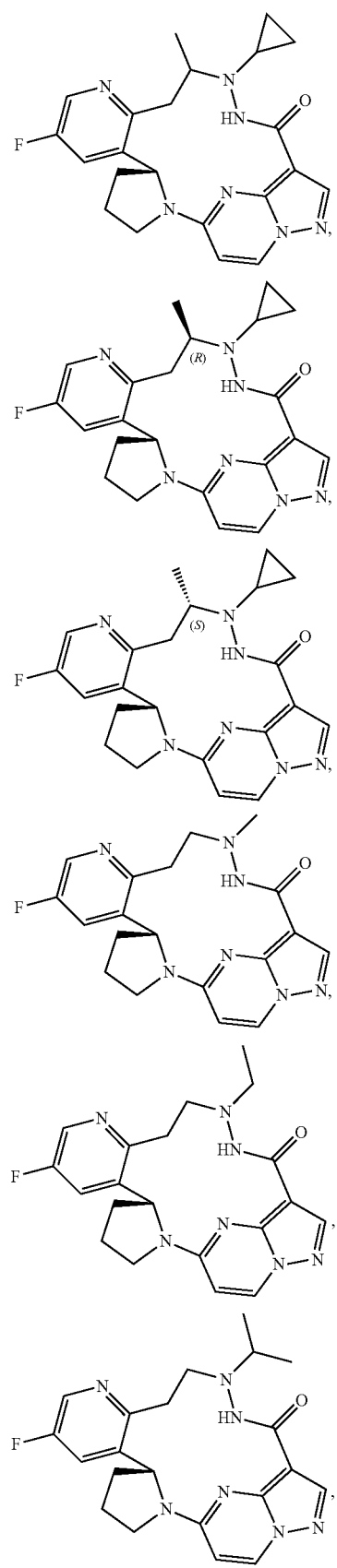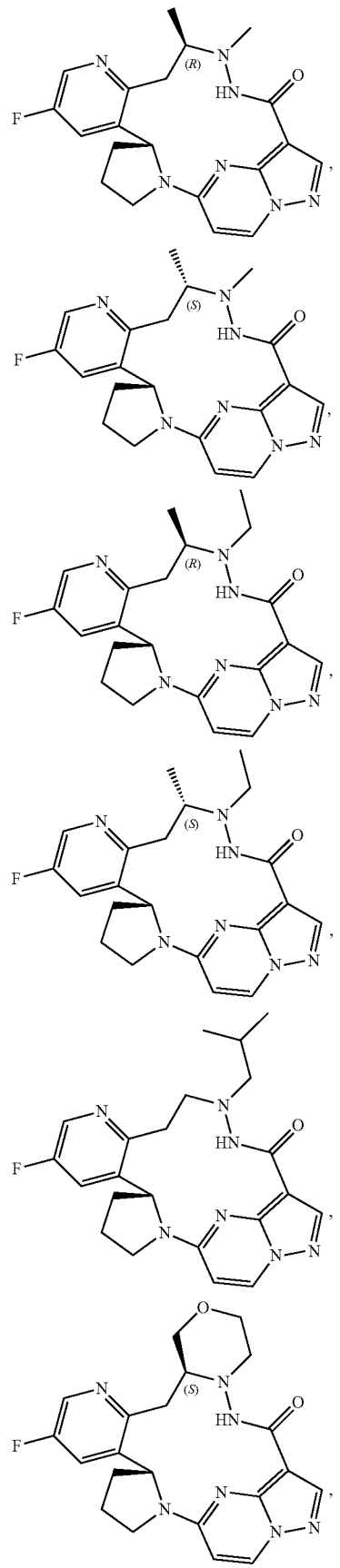

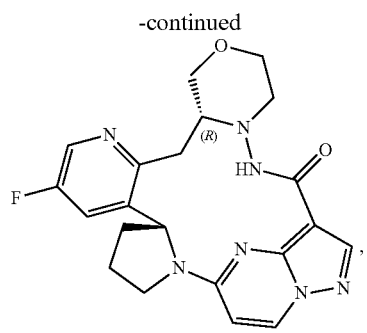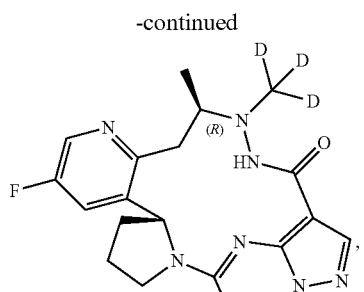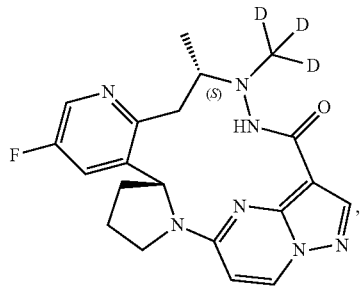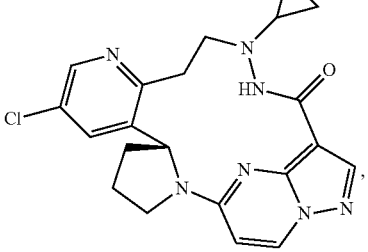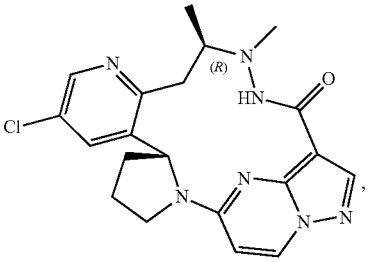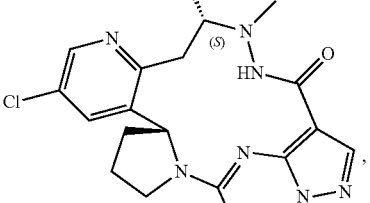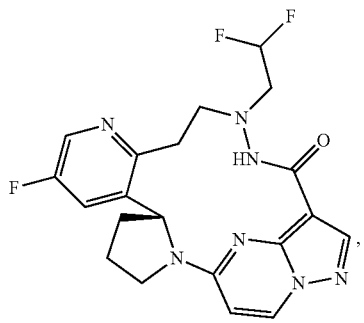

-continued
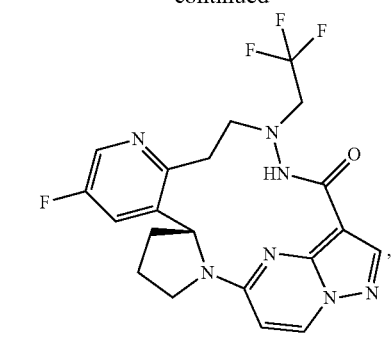
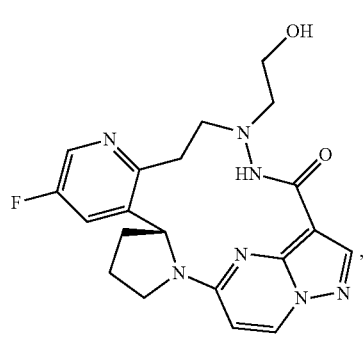
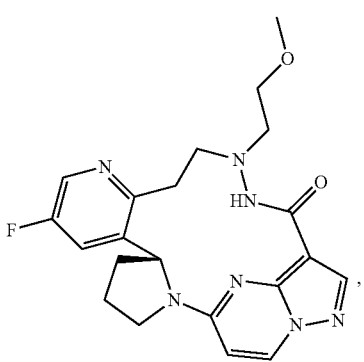
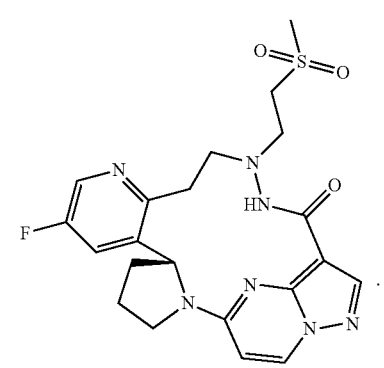
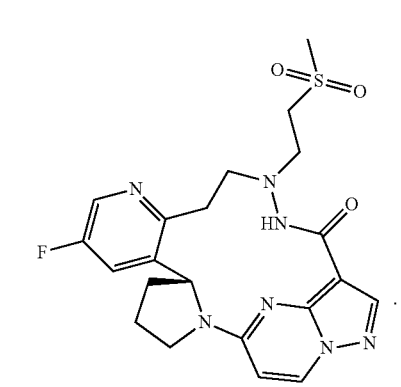
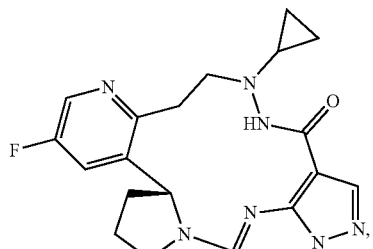
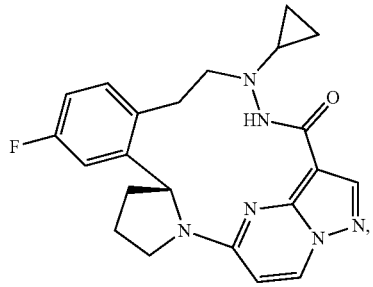
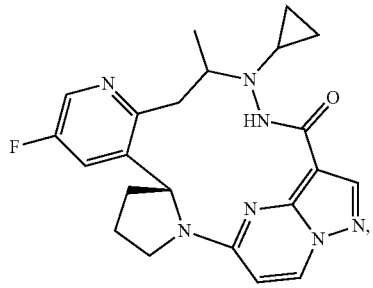
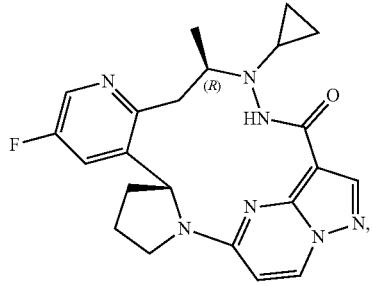
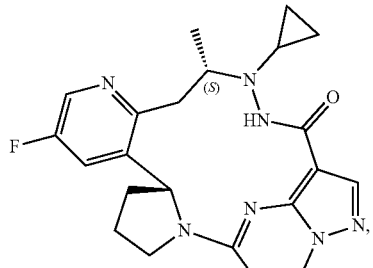
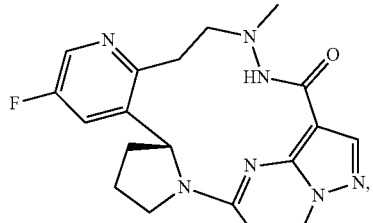
9. A compound, stereoisomer thereof or pharmaceutically acceptable salt thereof, wherein the compound has a structural formula selected from the following:

61
-continued

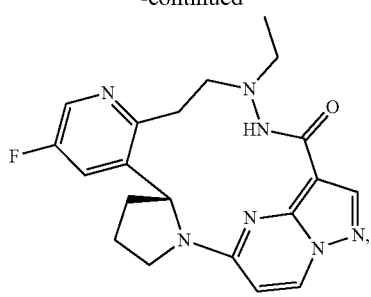

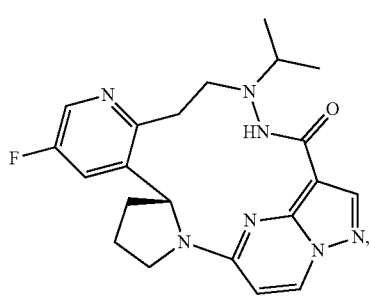

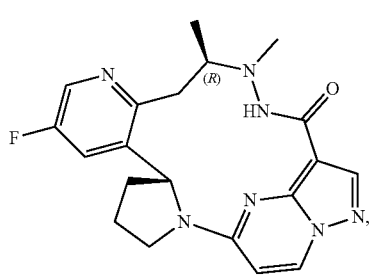

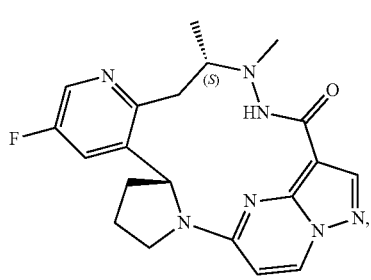

62
-continued

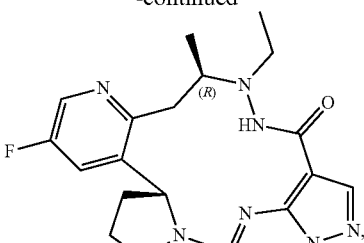

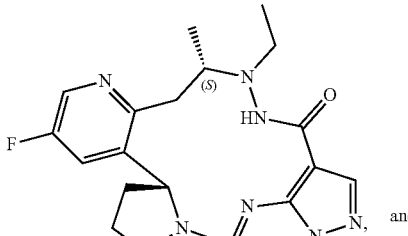

and

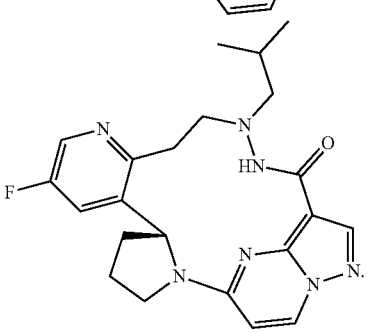

10. A pharmaceutical composition comprising the compound, stereoisomer thereof, or pharmaceutically acceptable salt thereof according to claim 1, and a pharmaceutically acceptable carrier.

11. The pharmaceutical composition according to claim 10, wherein the pharmaceutical composition is a form of capsule, powder, tablet, granule, pill, injection, syrup, oral liquid, inhalant, ointment, suppository, or patch.

12. A method for inhibiting tropomyosin receptor kinase activity diseases, comprising administering to a subject in need thereof an effective amount of the compound, stereoisomer thereof, or pharmaceutically acceptable salt thereof according to claim 1.

13. The method according to claim 12, wherein the tropomyosin receptor kinase is TrkA, TrkB, or TrkC.

* * * * *